(12) United States Patent
Arai et al.

(10) Patent No.: US 11,357,443 B2
(45) Date of Patent: Jun. 14, 2022

(54) DETERMINATION RESULT OUTPUT DEVICE, DETERMINATION RESULT PROVISION DEVICE, AND DETERMINATION RESULT OUTPUT SYSTEM

(71) Applicants: DAIKIN INDUSTRIES, LTD., Osaka (JP); TOKYO INSTITUTE OF TECHNOLOGY, Tokyo (JP)

(72) Inventors: Junichiro Arai, Osaka (JP); Yasunori Kotani, Tokyo (JP); Taro Tomatsu, Tokyo (JP); Yoshimi Ohgami, Tokyo (JP)

(73) Assignees: Daikin Industries, Ltd., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 800 days.

(21) Appl. No.: 16/080,284

(22) PCT Filed: Feb. 28, 2017

(86) PCT No.: PCT/JP2017/007991
§ 371 (c)(1),
(2) Date: Aug. 27, 2018

(87) PCT Pub. No.: WO2017/150576
PCT Pub. Date: Sep. 8, 2017

(65) Prior Publication Data
US 2019/0069832 A1    Mar. 7, 2019

(30) Foreign Application Priority Data

Feb. 29, 2016   (JP) .............................. JP2016-038483

(51) Int. Cl.
*A61B 5/00* (2006.01)
*A61B 5/01* (2006.01)
(Continued)

(52) U.S. Cl.
CPC .......... *A61B 5/4064* (2013.01); *A61B 5/0064* (2013.01); *A61B 5/0075* (2013.01);
(Continued)

(58) Field of Classification Search
None
See application file for complete search history.

(56) References Cited

U.S. PATENT DOCUMENTS 6,092,058 A * 7/2000 Smyth ..................... G06F 3/013
706/10
2009/0080730 A1* 3/2009 Pavlidis ............. G06K 9/00268
382/128

(Continued)

FOREIGN PATENT DOCUMENTS

JP    2007-202619 A    8/2007
JP    2011-150408 A    8/2011
(Continued)

OTHER PUBLICATIONS

Khan et al., "Classifying pretended and evoked facial expressions of positive and negative affective states using infrared measurement of skin temperature". ACM, 2009, vol. 6, Iss 1. (Year: 2009).*
(Continued)

*Primary Examiner* — Yi-Shan Yang
(74) *Attorney, Agent, or Firm* — Global IP Counselors, LLP

(57) ABSTRACT

A determination result output device and a determination result output system output a determination result indicating various states of a subject, and a determination result provision device provides a determination result. A determination result output system includes a determination result output device that outputs a determination result indicating the state of a subject, and a determination result provision device that provides the determination result. When acquir-
(Continued)

ing facial-surface change information related to a target purpose from the determination result output device, the determination result provision device generates determination information from facial-surface change information, determines a determination result including a state level of the subject, and sends the determination result to the determination result output device.

10 Claims, 30 Drawing Sheets

(51) Int. Cl.
 *A61B 5/16* (2006.01)
 *A61B 5/026* (2006.01)
(52) U.S. Cl.
 CPC ............ *A61B 5/0077* (2013.01); *A61B 5/015* (2013.01); *A61B 5/0261* (2013.01); *A61B 5/165* (2013.01); *A61B 5/168* (2013.01); *A61B 5/7246* (2013.01); *A61B 5/7264* (2013.01); *A61B 5/743* (2013.01); *A61B 5/01* (2013.01); *A61B 5/16* (2013.01); *A61B 5/162* (2013.01)

(56) References Cited

U.S. PATENT DOCUMENTS

2014/0347265 A1* 11/2014 Aimone ................ H04W 4/029
 345/156
2017/0281070 A1* 10/2017 Arai ........................ A61B 5/165

FOREIGN PATENT DOCUMENTS

| JP | 2012-34839 A | 2/2012 |
| JP | 2013-176406 A | 9/2013 |
| WO | 2014/138925 A1 | 9/2014 |

OTHER PUBLICATIONS

Nanh et al., "Classifying affective states using thermal infrared imaging of the human face". IEEE Transactions on Biomedical Engineering, vol. 57, No. 4, 2010. (Year: 2010).*
International Preliminary Report of corresponding PCT Application No. PCT/JP2017/007991 dated Sep. 13, 2018.
European Search Report of corresponding EP Application No. 17 76 0040.0 dated Jan. 30, 2020.
International Search Report of corresponding PCT Application No. PCT/JP2017/007991 dated May 9, 2017.

* cited by examiner

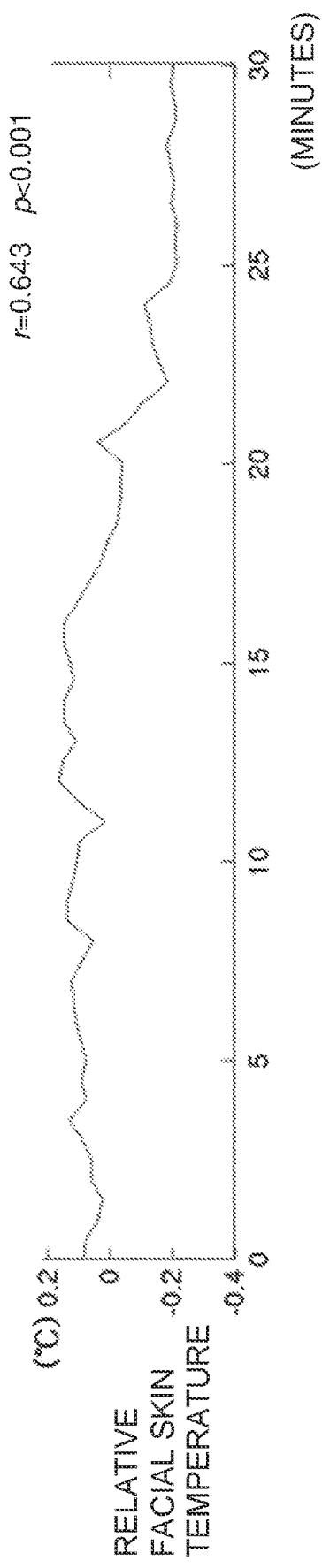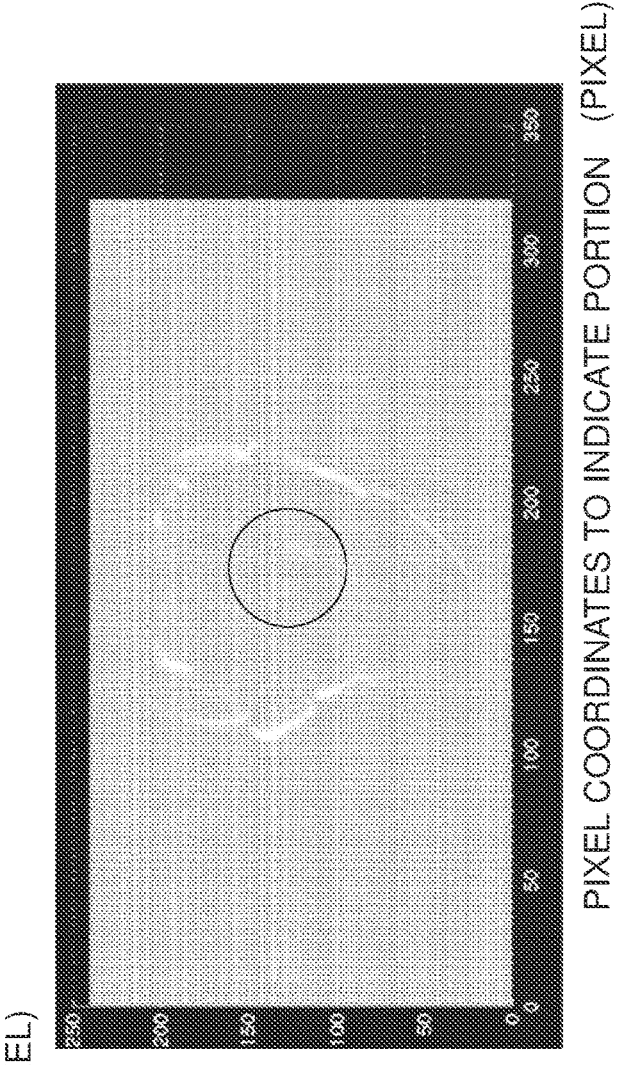

DETERMINATION RESULT OUTPUT DEVICE, DETERMINATION RESULT PROVISION DEVICE, AND DETERMINATION RESULT OUTPUT SYSTEM

CROSS-REFERENCE TO RELATED APPLICATIONS

This U.S. National stage application claims priority under 35 U.S.C. § 119(a) to Japanese Patent Application No. 2016-038483, filed in Japan on Feb. 29, 2016, the entire contents of which are hereby incorporated herein by reference.

TECHNICAL FIELD

The present invention relates to a determination result output device, a determination result provision device, and a determination result output system.

BACKGROUND ART

In recent years, estimation of the human brain activity has been attempted using data detected by electroencephalography (EEG), magnetic resonance imaging (fMRI: functional Magnetic Resonance Imaging), and near infrared spectroscopy (NIRS) as disclosed in Japanese Laid-open Patent Publication No. 2013-176406. Furthermore, applications, such as determination of the physical condition and the mental state of a human, have been researched based on the estimated brain activity.

SUMMARY

However, the electroencephalography and the near infrared spectroscopy require preprocessing, such as forcing a subject to attach electrodes thereon. The magnetic resonance imaging method requires measurement in a predetermined MRI room. In short, these methods have drawbacks of a complicated operation at the preparation stage, and a limited condition for measurement. All of these methods require enormous costs. Consequently, these methods may make it difficult to determine the physical condition and mental state of the subject or the like.

It is an object of the present invention to provide a device and system which can easily determine the physical condition and mental state of a subject. Specifically, it is an object of the present invention to provide a determination result output device and a determination result output system which achieve outputting of determination results indicating various states of the subject, and also to provide a determination result provision device which achieves provision of the determination result.

A determination result output device according to a first aspect of the present invention includes a target purpose selection unit, a brain-function activation information provision unit or a brain-function activation information detection unit, a facial-surface change information acquisition unit, and a determination result output unit. The target purpose selection unit selects one of a plurality of determination purposes as a target purpose. The brain-function activation information provision unit provides brain-function activation information corresponding to the target purpose. The brain-function activation information detection unit detects brain-function activation information corresponding to the target purpose. The facial-surface change information acquisition unit acquires facial-surface change information indicative of a time-series change in a facial surface data on a subject when the brain-function activation information is provided, or when the brain-function activation information is detected. The determination result output unit outputs a determination result indicative of a state of the subject based on the brain-function activation information corresponding to the target purpose and the facial-surface change information.

The determination result output device according to the first aspect determines the state of the subject based on the facial-surface change information on the subject and the brain-function activation information corresponding to the target purpose when the brain-function activation information is provided, or when the brain-function activation information is detected, thereby making it possible to determine various states of the subject with a simple configuration. Therefore, this can provide the device capable of easily determining the physical condition and mental state of the subject.

A determination result output device according to a second aspect of the present invention is the determination result output device of the first aspect that further includes a determination information generating unit, a correlation value calculation unit, and a determination result decision unit. The determination information generating unit generates determination information from the facial-surface change information. The correlation value calculation unit calculates a correlation value between brain-function activation information corresponding to the target purpose and the determination information. The determination result decision unit decides a determination result indicative of a state of the subject based on the correlation value.

The determination result output device according to the second aspect decides the determination result indicative of the state of the subject based on the correlation value between the brain-function activation information corresponding to the target purpose and the determination information, thereby making it possible to determine various states of the subject with a simple configuration.

A determination result output device according to a third aspect of the present invention is the determination result output device according to the second aspect wherein the determination information generating unit extracts a determination component related to the brain-function activation information corresponding to the target purpose by conducting singular value decomposition, principal component analysis, or independent component analysis on the facial-surface change information, and generates the determination information from the determination component.

The determination result output device according to the third aspect extracts the determination component related to the brain-function activation information corresponding to the selected target purpose from the facial-surface change information by the singular value decomposition, the principal component analysis, or the independent component analysis. Thus, the determination result output device can estimate the presence or absence of the brain activity of the subject without using any electrode or the like that requires preprocessing before attachment. In addition, the determination result indicative of various states of the subject according to the target purpose can be output based on the determination component corresponding to the brain function of the subject. A determination result output device according to a fourth aspect of the present invention is the determination result output device according to the third aspect that further includes a reference information storage unit. The reference information storage unit stores, as reference information in relation to a state level, an amount of change from a reference correlation value of a reference determination component of facial-surface change information with respect to brain-function activation information for each of the plurality of determination purposes. In addition, the determination result decision unit determines the state level of the subject based on the correlation value and the reference correlation value.

The determination result output device according to the fourth aspect can output the determination result indicative of various states of the subject corresponding to the target purpose by using the reference correlation value previously set.

A determination result provision device according to a fifth aspect of the present invention acquires a correlation value of determination information with respect to brain-function activation information related to a target purpose, from a determination result output device, and provides a determination result for the target purpose to the determination result output device. The determination result provision device includes a reference information storage unit, a determination result decision unit, and a determination result sending unit. The reference information storage unit stores an amount of change from a reference correlation value with respect to the brain-function activation information for each of the plurality of determination purposes, as reference information in relation to a state level. The determination result decision unit decides a determination result including a state level of the subject based on the reference information and a correlation value of determination information with respect to brain-function activation information related to a target purpose when acquiring the correlation value from the determination result output device. The determination result sending unit sends the determination result to the determination result output device.

The determination result provision device according to the fifth aspect can provide the determination result indicative of various states of the subject according to the target purpose by using the reference correlation value previously set.

A determination result output device according to a sixth aspect of the present invention sends a correlation value between brain-function activation information for a target purpose and determination information, to a determination result provision device and acquires a determination result for the target purpose from the determination result provision device. The determination result output device includes a target purpose selection unit, a brain-function activation information provision unit or a brain-function activation information detection unit, a facial-surface change information acquisition unit, a determination information generating unit, a correlation value calculation unit, a correlation value sending unit, a determination result acquisition unit, and a determination result output unit. The target purpose selection unit selects one of a plurality of determination purposes as a target purpose. The brain-function activation information provision unit provides brain-function activation information corresponding to the target purpose. The brain-function activation information detection unit detects brain-function activation information corresponding to the target purpose. The facial-surface change information acquisition unit acquires facial-surface change information indicative of a time-series change in facial surface data on the subject. The determination information generating unit generates determination information from the facial-surface change information. The correlation value calculation unit calculates a correlation value between the brain-function activation information and the determination information. The correlation value sending unit sends the correlation value in relation to the target purpose to the determination result provision device. The determination result acquisition unit acquires a determination result from the determination result provision device in response to sending of the correlation value and the target purpose. The determination result output unit outputs the determination result.

The determination result output device according to the sixth aspect decides the determination result indicative of the state of the subject based on the correlation value between the brain-function activation information corresponding to the target purpose and the determination information, thereby making it possible to determine various states of the subject with a simple configuration.

A determination result output device according to a seventh aspect of the present invention is the determination result output device according to the sixth aspect wherein the determination information generating unit extracts a determination component related to brain-function activation information corresponding to the target purpose by singular value decomposition, principal component analysis, or independent component analysis, and generates the determination information from the determination component.

The determination result output device according to the seventh aspect extracts the determination component related to the brain-function activation information corresponding to the selected target purpose from the facial-surface change information by the singular value decomposition, the principal component analysis, or the independent component analysis. Thus, the determination result output device can estimate the presence or absence of the brain activity of the subject without using any electrode or the like that requires preprocessing before attachment. In addition, the determination result indicative of various states of the subject corresponding to the target purpose can be output based on the component corresponding to the brain function of the subject. A determination result output system according to an eighth aspect of the present invention includes a determination result output device that outputs a determination result indicative of a state of a subject; and a determination information provision device that provides the determination result. The determination result output device includes: a target purpose selection unit that selects one of a plurality of determination purposes as a target purpose; a brain-function activation information provision unit that provides brain-function activation information corresponding to the target purpose, or a brain-function activation information detection unit that detects brain-function activation information corresponding to the target purpose; a facial-surface change information acquisition unit that acquires facial-surface change information indicative of a time-series change in facial surface data on the subject; a determination information generating unit that generates determination information from the facial-surface change information; a correlation value calculation unit that calculates a correlation value between the brain-function activation information and the determination information; a correlation value sending unit that sends the correlation value in relation to the target purpose to the determination result provision device; a determination result acquisition unit that acquires a determination result from the determination result provision device in response to sending of the correlation value and the target purpose; and a determination result output unit that outputs the determination result. The determination result provision device includes: a reference information storage unit that stores an amount of change from a reference correlation value with respect to brain-function activation information for each of the plurality of determination purposes, as reference information in relation to a state level; a determination result decision unit that decides a determination result including a state level of the subject based on the reference information and a correlation value related to the target purpose when acquiring the correlation value from the determination result output device; and a determination result sending unit that sends the determination result to the determination result output device.

The determination result output system according to the eighth aspect decides the determination result indicative of the state of the subject based on the correlation value between the brain-function activation information corresponding to the target purpose and the determination information, thereby making it possible to determine various states of the subject with a simple configuration.

A determination result output system according to a ninth aspect of the present invention is the determination result output system according to the eighth aspect wherein the determination information generating unit extracts a determination component related to brain-function activation information corresponding to the target purpose by conducting singular value decomposition, principal component analysis, or independent component analysis on the facial-surface change information, and generates the determination information from the determination component.

The determination result output system according to the ninth aspect extracts the determination component related to the brain-function activation information corresponding to the selected target purpose from the facial-surface change information by the singular value decomposition, the principal component analysis, or the independent component analysis. Thus, the determination result output system can estimate the presence or absence of the brain activity of the subject without using any electrode or the like that requires preprocessing before attachment. Furthermore, the determination result output system can output the determination result indicative of various states of the subject according to the target purpose based on the determination component corresponding to the brain function of the subject.

A determination result provision device according to a tenth aspect of the present invention acquires facial-surface change information for a target purpose from a determination result output device and provides a determination result for the target purpose to the determination result output device. The determination result provision device includes a reference information storage unit, a determination information generating unit, a correlation value calculation unit, a determination result decision unit, and a determination result sending unit. The reference information storage unit stores an amount of change from a reference correlation value with respect to brain-function activation information for each of the plurality of determination purposes, as reference information in relation to a state level. The determination information generating unit generates determination information from the facial-surface change information when acquiring the facial-surface change information related to the target purpose from the determination result output device. The correlation value calculation unit calculates a correlation value between the brain-function activation information and the determination information. The determination result decision unit decides a determination result including a state level of the subject based on the correlation value and the reference information. The determination result sending unit sends the determination result to the determination result output device.

The determination result provision device according to the tenth aspect decides the determination result indicative of the state of the subject based on the correlation value between the brain-function activation information corresponding to the target purpose and the determination information, thereby making it possible to determine various states of the subject with a simple configuration.

A determination result provision device according to an eleventh aspect of the present invention is the determination result provision device according to the tenth aspect wherein the determination information generating unit extracts a determination component related to brain-function activation information corresponding to the target purpose by conducting singular value decomposition, principal component analysis, or independent component analysis on the facial-surface change information, and generates the determination information from the determination component.

The determination result provision device according to the eleventh aspect extracts the determination component related to the brain-function activation information corresponding to the selected target purpose from the facial-surface change information by the singular value decomposition, the principal component analysis, or the independent component analysis. Thus, the determination result output device can estimate the presence or absence of the brain activity of the subject without using any electrodes or the like that require preprocessing before attachment. Furthermore, the determination result provision device can provide the determination result indicative of various states of the subject according to the target purpose based on the determination component corresponding to the brain function of the subject.

A determination result output device according to a twelfth aspect of the present invention sends facial-surface change information related to a target purpose, to a determination result provision device and to acquire a determination result for the target purpose from the determination result provision device. The determination result output device includes a target purpose selection unit, a brain-function activation information provision unit or a brain-function activation information detection unit, a facial-surface change information acquisition unit, a facial-surface change information sending unit, a determination result acquisition unit, and a determination result output unit. The target purpose selection unit selects one of a plurality of determination purposes as a target purpose. The brain-function activation information provision unit provides brain-function activation information corresponding to the target purpose. The brain-function activation information detection unit detects brain-function activation information corresponding to the target purpose. The facial-surface change information acquisition unit acquires facial-surface change information indicative of a time-series change in facial surface data on the subject. The facial-surface change information sending unit sends the facial-surface change information to the determination result provision device in relation to the target purpose. The determination result acquisition unit acquires a determination result from the determination result provision device in response to sending of the facial-surface change information and the target purpose. The determination result output unit outputs the determination result.

The determination result output device according to the twelfth aspect can select one of the plurality of determination purposes as the target purpose to output the determination result corresponding to the target purpose.

A determination result output system according to a thirteenth aspect of the present invention includes: a determination result output device that outputs a determination result indicative of a state of a subject; and a determination information provision device that provides the determination result. The determination result output device includes: a target purpose selection unit that selects one of a plurality of determination purposes as a target purpose; a brain-function activation information provision unit that provides brain-function activation information corresponding to the target purpose, or a brain-function activation information detection unit that detects brain-function activation information corresponding to the target purpose, a facial-surface change information acquisition unit that acquires facial-surface change information indicative of a time-series change in facial surface data on the subject; a facial-surface change information sending unit that sends the facial-surface change information to the determination result provision device in relation to the target purpose; a determination result acquisition unit that acquires a determination result from the determination result provision device in response to sending of the facial-surface change information and the target purpose; and a determination result output unit that outputs the determination result. The determination result provision device includes: a reference information storage unit that stores an amount of change from a reference correlation value with respect to brain-function activation information for each of the plurality of determination purposes, as reference information in relation to a state level; a determination information generating unit that generates determination information from the facial-surface change information when acquiring the facial-surface change information related to the target purpose from the determination result output device; and a correlation value calculation unit that calculates a correlation value between the brain-function activation information and the determination information; a determination result decision unit that decides a determination result including a state level of the subject based on the correlation value and the reference information; and a determination result sending unit that sends the determination result to the determination result output device.

The determination result output device according to the thirteenth aspect decides the determination result indicative of the state of the subject based on the correlation value between the brain-function activation information corresponding to the target purpose and the determination information, thereby making it possible to determine various states of the subject with a simple configuration.

A determination result output system according to a fourteenth aspect of the present invention is the determination result output system according to the thirteenth aspect, wherein the determination information generating unit extracts a determination component related to brain-function activation information corresponding to the target purpose by conducting singular value decomposition, principal component analysis, or independent component analysis on the facial-surface change information, and generates the determination information from the determination component.

The determination result output system according to the fourteenth aspect extracts the determination component related to the brain-function activation information corresponding to the selected target purpose from the facial-surface change information by the singular value decomposition, the principal component analysis, or the independent component analysis. Thus, the determination result output system can estimate the presence or absence of the brain activity of the subject without using any electrodes or the like that require preprocessing before attachment. In addition, the determination result indicative of various states of the subject corresponding to the target purpose can be output based on the determination component corresponding to the brain function of the subject.

With the determination result output device according to each of the first to fourth aspects, the determination results indicative of various states of the subject depending on the target purpose can be output.

With the determination result provision device according to each of the fifth and sixth aspects, the determination results indicative of various states of the subject depending on the target purpose can be provided.

With the determination result output device according to the seventh aspect, the determination results indicative of various states of the subject depending on the target purpose can be output.

With the determination result output system according to each of the eighth and ninth aspects, the determination results indicative of various states of the subject depending on the target purpose can be output.

With the determination result provision device according to each of the tenth and eleventh aspects, the determination results indicative of various states of the subject depending on the target purpose can be provided.

With the determination result output device according to the twelfth aspect, the determination results for the target purpose can be output.

With the determination result output system according to each of the thirteenth and fourteenth aspects, the determination results indicative of various states of the subject depending on the target purpose can be output.

BRIEF DESCRIPTION OF THE DRAWINGS

FIGS. 2A and 2B are diagrams showing part of the analysis result of facial skin temperature data;

DESCRIPTION OF EMBODIMENTS

Figures 1A, 1B:
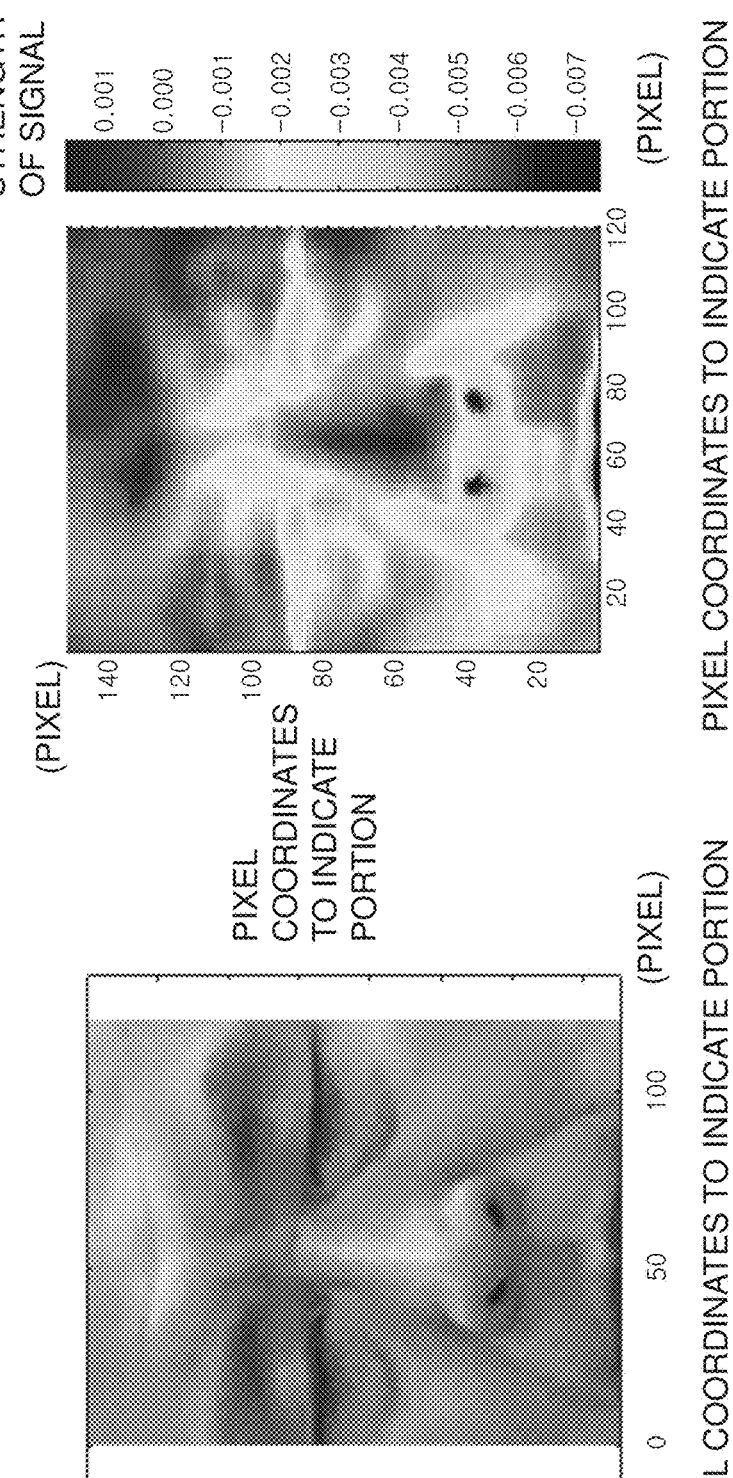
FIGS. 1A and 1B are diagrams showing an example of photographed image data and the analysis result of this data.

Prior to describing embodiments of the present invention, first, a description will be given on the findings conducted by the inventors, which have become an important basis in making the present invention.

(1) Main Points of Findings Conducted by Inventors

Human brain activities are known to reflect human intellectual activities (cognitive activity and the like) and emotional activities (pleasure/discomfort activities, and the like). Attempts to estimate the human brain activity have been conventionally made, but in this case, data detected by any of the electroencephalography, magnetic resonance imaging, and near infrared spectroscopy is often utilized.

Here, in a detection method, for example, brain wave electrodes need to be attached onto a test subject in the case of employing the electroencephalography. When the brain wave electrodes are attached onto the test subject, the resistance between the skin and the electrodes should be reduced. Due to this, additional operations, such as abrading the skin and applying a paste to the electrodes, are required. In addition, in the case of employing the magnetic resonance imaging method, the measurement conditions are limited. For example, the measurement of the brain waves cannot be performed in a place other than an MRI room, and metal is not permitted to be brought into a measurement room. Furthermore, in the case of employing the near infrared spectroscopy method, probes need to be attached onto a test subject. However, the test subject may feel pain when wearing the probes for a long time, or the brain waves cannot be accurately detected depending on the contact state between the hair of the test subject and the probes. As such, when a conventional detection method is employed to measure the human brain activity, a heavy burden is imposed on the test subject. For example, preprocessing is required when the test subject wears the brain wave electrodes, the probes, or the like, or the measurement conditions are limited.

Therefore, there is a need to develop a means for enabling easy estimation of the human brain activity while reducing the burden on the test subject.

The inventors have conceived that the human brain activity can be estimated based on the human's facial skin temperature, or the blood circulation state of the facial surface, which is considered to be proportional to the facial skin temperature. The human's facial skin temperature can be measured by using a measurement device, such as thermography, and the blood circulation state of the facial surface, that is, the facial blood circulation amount can be estimated from RGB data of a photographed image on the facial surface acquired using an imaging device. As such, the facial skin temperature or the photographed image on the facial surface can be acquired without attaching any sensor that requires preprocessing before attachment, such as brain wave electrodes or probes.

On the other hand, the human's facial skin temperature is known to change under the influence of various factors, such as the outside air temperature and/or the activity of autonomic nerves. Due to this, in case that the brain activity is estimated based on the facial skin temperature or the facial blood circulation amount, which is considered to be proportional to the facial skin temperature, it is thought to be very difficult to determine whether the acquired data reflects only the brain activity.

As a result of intensive research, the inventors have found that time-series facial skin temperature data, which includes temperature data acquired by detecting facial skin temperatures and positional data (coordinate data) on a detected part, or time-series facial blood-circulation-amount data, which is calculated based on the RGB data obtained from the time-series photographed image data on the facial surface, is decomposed into a plurality of components by the singular value decomposition method, principal component analysis method, or independent component analysis method, and then the decomposed components are analyzed, which can identify the component indicative of the changes in the facial skin temperature or changes in the facial blood circulation amount that reflect the brain activity. Eventually, the inventors have estimated and analyzed the brain activity of the subject and hence reached the present invention capable of visualizing the physiological state of the subject based on the estimated brain activity.

(2) Acquiring Method of Various Data Regarding Facial Surface and Analyzing Method of Acquired Various Data (2-1) Acquiring Method of Facial Skin Temperature Data and Analyzing Method of Facial Skin Temperature Data Next, a description will be given on the acquiring method of the facial skin temperature data, used by the inventors to obtain the above findings, as well as the analyzing method of the facial skin temperature data.

In the present test, facial skin temperature data was acquired from six test subjects. Specifically, each test subject was seated on a chair placed in an artificial weather room maintained at room temperature of 25° C., and facial skin temperature data was acquired from the entire facial surface of the subject by using an infrared thermography device. The infrared thermography device is a device which detects infrared radiant energy emitted from an object with an infrared camera, then converts the detected infrared radiant energy into a temperature of a surface of the object (here, a temperature in units of Celsius), and thereby can display and store the temperature distribution of the converted temperatures as the facial skin temperature data (for example, image data representing the temperature distribution). Note that in the present test, an R300 manufactured by NEC Avio Infrared Technologies Co., Ltd. was used as an infrared thermography device. The infrared camera was placed in front of the test subject and at a distance of 1.5 m from the test subject. Subsequently, acquiring the facial skin temperature data was continued for 30 minutes.

In the present test, a brain function activation task was given to the test subject, while the facial skin temperature data was being acquired. Thus, the facial skin temperature data during a brain non-activation time and the facial skin temperature data during a brain activation time were acquired. The brain function activation tasks include psychological operations done by a test subject based on a picture displayed on a display device or the like, such as calculation, recognition of numerical values, shape, and color, and memorization of marks, characters, and languages. In the present test, "mental arithmetic of multiplication" was adopted as the brain function activation task, which forces the test subject to do operations, such as calculating numerical characters displayed on a display device in longhand and inputting answers on a keyboard. Note that in the present test, the brain function activation task was continuously given to the test subjects for ten minutes after five minutes have elapsed since the start of acquiring the facial skin temperature data.

In the analysis of the facial skin temperature data, the singular value decomposition was performed on the acquired facial skin temperature data by using the SVD (Singular Value Decomposition) of MATLAB (registered trademark) as an analysis tool. In the singular value decomposition, the target was defined as all the facial skin temperature data acquired in time series (data for 30 minutes), the factor was defined as time data acquired every 30 seconds (60 time points for 30 minutes), and the measure was defined as the facial skin temperature data (240×320 pixels) in that time period (30 seconds). By the singular value decomposition, the facial skin temperature data X was decomposed into a plurality of components, and then a time distribution V and a space distribution U of each of the components and a singular value S indicative of the size of each component were calculated.

Note that the relationship between these can be given by the formula below:

$$X=(U*S)*V'  \quad\quad [\text{Formula 1}]$$

where V' is a matrix configured by interchanging columns and rows of V.

Then, the time distribution V and the space distribution U of each component determined by the singular value decomposition were plotted in graphs to generate a component waveform diagram and a temperature distribution diagram of each component.

Further, the thus-formed component waveform diagram and temperature distribution diagram of each component were analyzed to identify a component which exhibited a change in the skin temperature that reflected the brain activity.

Regarding the component waveform diagram of each component, analysis was conducted on the presence or absence of the correlation between the amplitude of the component waveform and each of the brain non-activation time and the brain activation time. Specifically, it was evaluated whether or not there was a correlation between the amplitude shown in the component waveform diagram of each component and the brain non-activation period/activation period. In the present test, during the period of time when the facial skin temperature data was being acquired, the brain non-activation time was defined as a period of time with no brain function activation task given to the test subject, and specifically, a period of five minutes from the start of data acquisition and a period of 15 minutes from when 15 minutes had elapsed since the start of data acquisition to the end of data acquisition, whereas the brain activation time was defined as a period of time with the brain function activation task given to the test subject, and specifically, a period of ten minutes from the time when five minutes had elapsed since the start of data acquisition to the time when ten minutes had elapsed since then. Regarding the component waveform diagram of each component, analysis was conducted on the presence or absence of the correlation between the amplitude of the component waveform and each of the brain non-activation time and the brain activation time. It is noted that the presence or absence of the correlation was determined by using a statistical correlation analysis; the correlation was determined to be present if a significance level ($\alpha$) was 0.05 or less.

Regarding the temperature distribution diagram of each component, analysis was conducted on the presence or absence of a temperature change at a predetermined part of the facial surface. Here, the brain has a mechanism called "Selective Brain Cooling System", which cools the brain independently of body temperature. The selective brain cooling system is known to discharge heat generated by the brain activity through the forehead and the paranasal sinus peripheral region (including the glabella and the surroundings of the nose). In the present test, it was evaluated whether or not there is a temperature change in the paranasal sinus peripheral region and the forehead on the temperature distribution diagram of each component. The presence or absence of a temperature change in the paranasal sinus peripheral region and the forehead in the temperature distribution diagram was determined by visual inspection of the presence or absence of the temperature change, or based on whether or not the temperature in the paranasal sinus peripheral region and the forehead differs by 1 standard deviation (SD) or more from the mean temperature of the entire measured data.

It is noted that the polarity (plus or minus) of the facial skin temperature data X is determined depending on the relationship among the values of the space distribution U, the singular value S, and the time distribution V, and hence the polarity appears to be inversed in the component waveform diagram and the temperature distribution diagram of each component in some cases. Thus, with regard to the evaluation of the component waveform diagram and the temperature distribution diagram, the polarity was not set as an evaluation target.

Here, as mentioned above, the infrared thermography device converts infrared radiant energy detected from a part of an object into temperatures and then utilizes the temperature distribution of those temperatures as the facial skin temperature data. When the facial skin temperature of a human is acquired as the target using the infrared thermography device, temperature changes (so-called noises) that are not related to various brain activities, such as facial movement and/or autonomic nerve activity, might also be acquired as the facial skin temperature data (see FIG. 1A). For this reason, in order to detect such a temperature change not related to the brain activity, relative facial skin temperature data was created so as to set an average value of all temperature data included in the facial skin temperature data captured every 30 seconds to "0". Then, the created facial skin temperature data was also subjected to the singular value decomposition using the SVD of MATLAB (registered trademark) as an analysis tool, thereby creating a component waveform diagram and a temperature distribution diagram of each component corresponding to a singular value S. Referring to this, analysis was conducted to identify components exhibiting the changes in the skin temperature that reflected the brain activities.

Hereinafter, for convenience of the description, the facial skin temperature data acquired in the infrared thermography device will be referred to as the "facial skin temperature data corresponding to the temperature conversion data". Meanwhile, the relative facial skin temperature data created by setting an average value of all temperature data included in the facial skin temperature data corresponding to the temperature conversion data every predetermined time (in the present test, every 30 seconds) to "0" will be referred to as the "facial skin temperature data corresponding to the relative temperature conversion data".

With regard to one of six test subjects, in addition to detecting the facial skin temperature by the infrared thermography device, electrodes were connected and attached on the scalp of the test subject to measure his or her brain waves, thereby evaluating the correlation between the amplitude of each component shown in the component waveform diagram and the amplitude of β waves (brain waves at frequencies of 14 to 30 Hz), which are known to have a waveform appearing in an awake or stressed human. In the electroencephalography, electrodes were placed at six parts (F3, F4, C3, C4, Cz, Pz) based on the International 10-20 method.

On the other hand, it can be considered that the head of the test subject moves up and down while the test subject is given a brain function activation task. In such a case, the position of the test subject's facial surface changes with respect to the infrared camera. A control test was conducted on one test subject to verify whether or not this change in the facial position influences changes in the skin temperature. In the control test for verifying the influence of the test subject's movement in acquiring the facial skin temperature data, the infrared thermography device is used as with the above-mentioned test to thereby acquire the facial skin temperature data regarding the test subject. In addition, the test subject was forced to do an operation of pressing a keyboard at random timings, while the brain function activation task was not given applied to the test subject (i.e., during the brain non-activation time). Also, with regard to the facial skin temperature data corresponding to the temperature conversion data obtained in this control experiment and the facial skin temperature data corresponding to the relative temperature conversion data, the singular value decomposition was conducted using the SVD of MATLAB (registered trademark) as the analysis tool, thereby generating a component waveform diagram and a temperature distribution diagram of each component corresponding to a singular value S. In this way, the analysis was conducted to identify components exhibiting the changes in the skin temperature that reflected the brain activities.

(2-2) Acquiring Method of Photographed Image Data on the Facial Surface and Analyzing Method of Photographed Image Data on the Facial Surface FIG. 1A is a diagram showing an example of photographed image data acquired from the paranasal sinus peripheral region on the facial surface of the test subject, photographed by an imaging device. FIG. 1B is a diagram showing an example of a blood circulation amount distribution diagram (image map).

Next, a description will be given on the acquiring method of photographed image data on the facial surface as well as the analyzing method of photographed image data on the facial surface, which were used by the inventors to obtain the above-mentioned findings.

In the present test, the photographed image data were acquired from the faces of six test subjects. Specifically, each test subject was seated on a chair placed in an artificial weather room maintained at room temperature of 25° C., and then the photographed image data on the paranasal sinus peripheral region at the entire facial surface of each test subject was acquired in time series by using an imaging device capable of acquiring images in time series.

Furthermore, based on the above-mentioned selective brain cooling mechanism, the changes in the facial blood circulation amount, which is considered to be proportional to the facial skin temperature related to the brain activity, are thought to appear around the forehead and/or paranasal sinuses. Through this, the inventors have conceived that recognizing the changes in the facial blood circulation amount around at least one of the forehead and/or the paranasal sinuses can estimate the brain activity with high accuracy. To this end, the present test acquired the photographed image data on the paranasal sinus peripheral region at the facial surface of the test subject in time series.

In the present test, color moving image data was acquired as time-series photographed image data by using an imaging device mounted on the side of a liquid crystal display of iPad Air (registered trademark), manufactured by Apple Inc., as the imaging device. The imaging device was placed in front of the test subject and at a distance of 1.0 m from the test subject. Then, the moving image data on the facial surface of the test subject was acquired by continuously capturing the photographed image data for 30 minutes along the time axis in a capturing cycle of 30 frames/sec using the imaging device.

In the present test, a brain function activation task was given to the test subject, while the moving image data on the facial surface was being acquired. In this way, the moving image data on the facial surface during the brain non-activation time and during the brain activation time were acquired. In the present test, like the above-mentioned test, "mental arithmetic of multiplication" was adopted as the brain function activation task, which forces the test subject to do operations, such as calculating numerical characters displayed on a display device in longhand and inputting answers on a keyboard. Note that in the present test, the brain function activation task was given to the test subject for ten minutes after five minutes have elapsed since the start of acquiring the moving image data on the facial surface.

In the analysis of the moving image data on the facial surface, blood-circulation-amount data was calculated based on the RGB data acquired from the moving image data on the photographed facial surface, and then the calculated time-series blood-circulation-amount data was subjected to singular value decomposition by using the SVD of MATLAB (registered trademark) as an analysis tool. Here, an erythema index "a*" that correlates with skin redness and hemoglobin amount computed from the RGB data on the image was determined as the blood-circulation-amount data in accordance with the CIE-L*a*b* color coordinate system. In the singular value decomposition, the target was defined as the blood-circulation-amount data (here, erythema index) determined based on the RGB data acquired from all the moving image data (data acquired for 30 minutes) in time series, the factor was defined as time data acquired every 30 seconds (60 time points for 30 minutes), and the measure was defined as the erythema index computed from the RGB data in that time period (every 30 seconds) (erythema index obtained by taking frame data for one second every 30 seconds and computing from an average of RGB values obtained from the frame data; 240×320 pixels). By the singular value decomposition, the time-series blood-circulation-amount data based on the RGB data acquired from the moving image data on the facial surface was decomposed into a plurality of components, and then a time distribution V and a space distribution U of each component and a singular value S indicative of the size of each component were calculated. Note that these relationships can be given by the same formula as the above-mentioned formula (Formula 1).

Then, the time distribution V and the space distribution U of each component determined by the singular value decomposition were plotted in graphs to generate a component waveform diagram and a blood circulation amount distribution diagram of each component.

Further, the thus-generated component waveform diagram and blood circulation amount distribution diagram of each component were analyzed to identify a component which exhibited a change in the facial blood circulation amount that reflected the brain activity, i.e., an RGB change on the facial surface.

Regarding the component waveform diagram of each component, analysis was conducted on the presence or absence of the correlation between the amplitude of the component waveform and each of the brain non-activation time and the brain activation time. Specifically, it was evaluated whether or not there was a correlation between the amplitude of the component shown in the component waveform diagram of each component and the brain non-activation period/activation period. In the present test, for a period of time during which the photographed image data on the facial surface was being acquired, the brain non-activation time was defined as a period of time with no brain function activation task given to the test subject, and specifically, a period of five minutes from the start of data acquisition and a period of 15 minutes from when 15 minutes had elapsed since the start of data acquisition to the end of data acquisition, whereas the brain activation time was defined as a period of time with the brain function activation task given to the test subjects, and specifically, a period often minutes from the time when five minutes had elapsed since the start of data acquisition to the time when ten minutes had elapsed since then. Regarding the component waveform diagram of each component, evaluation was conducted on the presence or absence of the correlation between the amplitude of each component shown in the component waveform diagram and each of the brain non-activation time and the brain activation time. It is noted that the presence or absence of the correlation was determined by using statistical correlation analysis, the correlation was determined to be present if a significance level ($\alpha$) was 0.01 or less.

Regarding the blood circulation amount distribution diagram of each component, analysis was conducted on the presence or absence of a change in the blood circulation amount at a predetermined part of the facial surface. The blood circulation amount distribution diagram was generated by arranging the space distributions U calculated every pixel, at the position of each pixel. In the blood circulation amount distribution diagram of each component created in this way, it was evaluated whether or not there was any change in the blood circulation amount at the paranasal sinus peripheral region and/or the forehead. Note that the presence or absence of a change in the blood circulation amount at the paranasal sinus peripheral region and/or the forehead in the blood circulation amount diagram was determined with reference to visual inspection of the presence or absence of the change in the blood circulation amount, or whether the values of the blood circulation amount at the paranasal sinus peripheral region and the forehead shown in FIG. 1B were not "0.000".

It is noted that the polarity (plus or minus) of the blood-circulation-amount data X is determined depending on the relationship among the values of the space distribution U, the singular value S, and the time distribution V, and hence the polarity appears to be inversed in the component waveform diagram and the blood circulation amount distribution diagram of each component in some cases. Thus, with regard to the evaluation of the component waveform diagram and the blood circulation amount distribution diagram, the polarity was not set as an evaluation target.

Further, to verify the correlation between the facial skin temperature and the facial blood circulation amount, while the photographed image data on the facial surface was acquired from the six test subjects in time series, the facial skin temperature data was also acquired in time series by the infrared thermography device. Then, the acquired facial skin temperature data was also subjected to the singular value decomposition by using the SVD of MATLAB (registered trademark) as the analysis tool. The component waveform diagram for each component corresponding to the singular value S was generated. Based on this diagram, analysis was conducted on the presence or absence of the correlation between the amplitude of the component waveform and each of the brain non-activation time and the brain activation time. In the present test, the same device as that used in the above-mentioned test was used as an infrared thermography device. The infrared camera was placed in front of the test subject and at a distance of 1.5 m from the test subject.

In a case where the photographed image data on a facial surface is acquired by using the imaging device, if sunlight or the like hits the face during photographing, the light is reflected by the face. The reflected light occasionally enters a lens of the imaging device. As a result, the photographed image data on the photographed facial surface would have the reflected light recorded therein. Here, in the RGB data acquired from the photographed image data, a change in brightness based on the facial blood circulation amount is smaller than a change in brightness based on the reflected light. Because of this, if a blood circulation amount calculated based on the RGB data acquired from the photographed image data with the reflected light recorded therein is analyzed, it is considered that an RGB change (which is so-called noise) on the facial surface, which is unrelated to the brain activity, could be mixed in the RGB data. For this reason, in order to prevent mixing of such an RGB change on the facial surface not related to the brain activity, relative blood-circulation-amount data was created from the relative RGB data in which an average value of all RGB data acquired every 30 seconds is set to "0". Then, the created blood-circulation-amount data was subjected to the singular value decomposition using the SVD of MATLAB (registered trademark) as the analysis tool, thereby generating a component waveform diagram and a blood circulation amount distribution diagram of each component corresponding to a singular value S. In this way, analysis was conducted to identify components exhibiting the RGB changes on the facial surface that reflected the brain activities.

Hereinafter, for convenience of the description, the relative blood-circulation-amount data based on the relative RGB data created so as to set an average value of all RGB data created every predetermined time (in the present test, every 30 seconds) to "0" will be referred to as the "relative-conversion blood-circulation-amount data". Meanwhile, the blood-circulation-amount data based on the RGB data before conversion to the relative RGB data will be simply referred to as the "blood-circulation-amount data".

While the time-series photographed image data on the facial surfaces of six test subjects were being acquired by the imaging device, their brain waves were measured by connecting electrodes on the scalp of each test subject, thereby evaluating the correlation between the amplitude of each component shown in the component waveform diagram and the amplitude of β waves (brain waves at frequencies of 13 to 30 Hz), known to have a waveform appearing while the brain is active, such as the state of being awake or the like. In the electroencephalography, electrodes were placed at 19 parts on the scalp (Fp1, Fp2, F3, F4, C3, C4, P3, P4, O1, O2, F7, F8, T3, T4, T5, T6, Fz, Cz, and Pz) based on the International 10-20 method.

Furthermore, it can be considered that the head of the test subject moves up and down while the test subject is given a brain function activation task. In such a case, the position of the test subject's facial surface changes with respect to the imaging device. A control test was conducted on one test subject to verify whether or not this change in the facial position influences RGB changes on the facial surface. In the control test, the time-series photographed image data on the test subject's facial surface was acquired using the imaging device in the same manner as the above-mentioned test. In addition, the test subject was forced to do an operation of pressing a keyboard at random timings, while the brain function activation task was not given (i.e., during the brain non-activation time). Then, the singular value decomposition was also conducted on the time-series blood-circulation-amount data based on the RGB data acquired from the time-series photographed image data on the facial surface, photographed in the control test, by using the SVD of MATLAB (registered trademark) as the analysis tool. Subsequently, the component waveform diagram for each component corresponding to the singular value S was generated. Based on this diagram, analysis was conducted on the presence or absence of the correlation between the amplitude of the component waveform and each of the brain non-activation time and the brain activation time. In addition, analysis was conducted on the presence or absence of the correlation between the amplitude of each component waveform and an actual movement of the facial surface. An actual movement of the facial surface was evaluated by acquiring two-dimensional coordinates of one part on the face from the photographed image data, and calculating each movement distance of the facial surface every 30 seconds during photographing with reference to photographed image data of the start of the control experiment. Furthermore, analysis was also conducted on the presence or absence of the correlation between the amplitude of each component waveform and the number of inputs into the keyboard during the photographing. The number of inputs into the keyboard during the photographing was evaluated by calculating a simple moving average every 30 seconds in the time-series photographed image data.

(3) Analysis Result (3-1) Analysis Results of Facial Skin Temperature Data

Figure 3A:
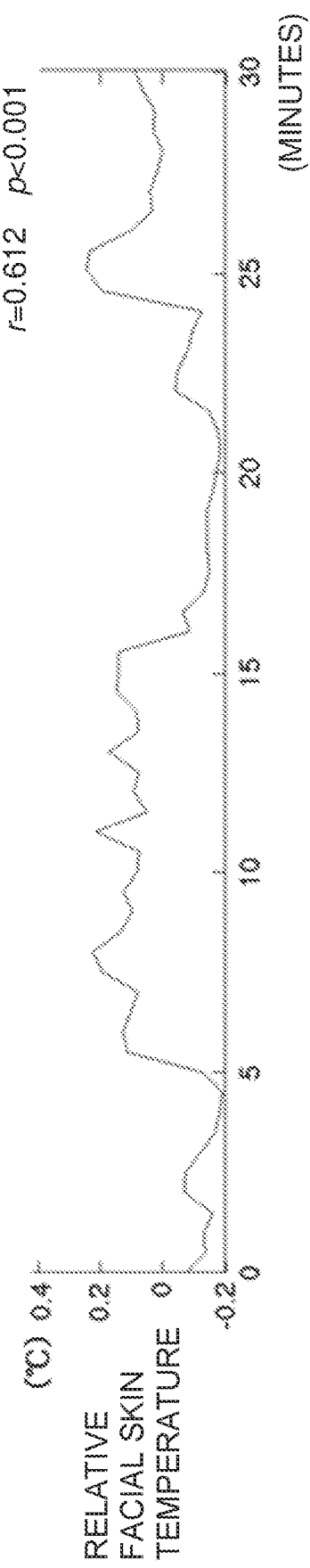
FIGS. 3A and 3B are diagrams showing part of the analysis result of the facial skin temperature data.
Figure 3B:
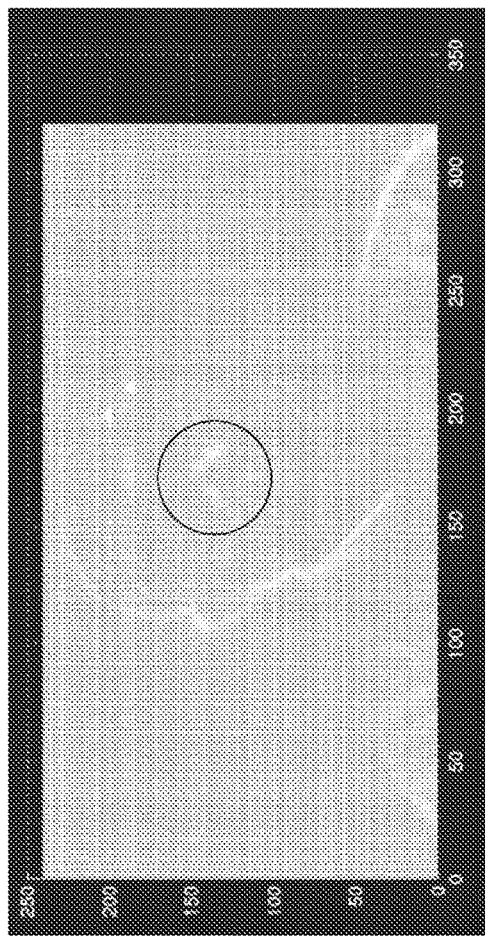
Figure 4:
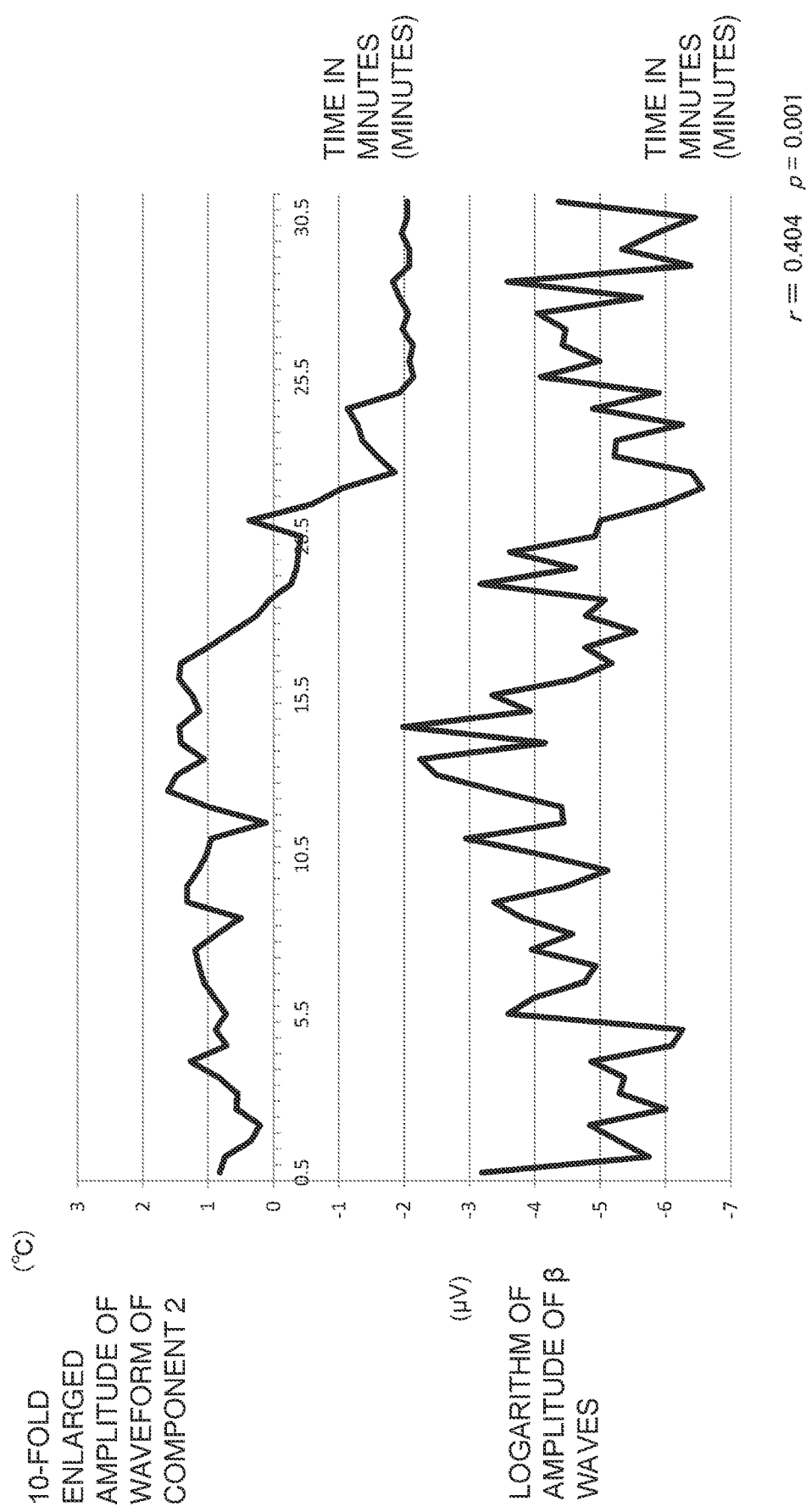
FIG. 4 is a diagram showing an amplitude of a component waveform of a component 2 and an amplitude of a $\beta$ wave among measured brain waves.
Figure 5:
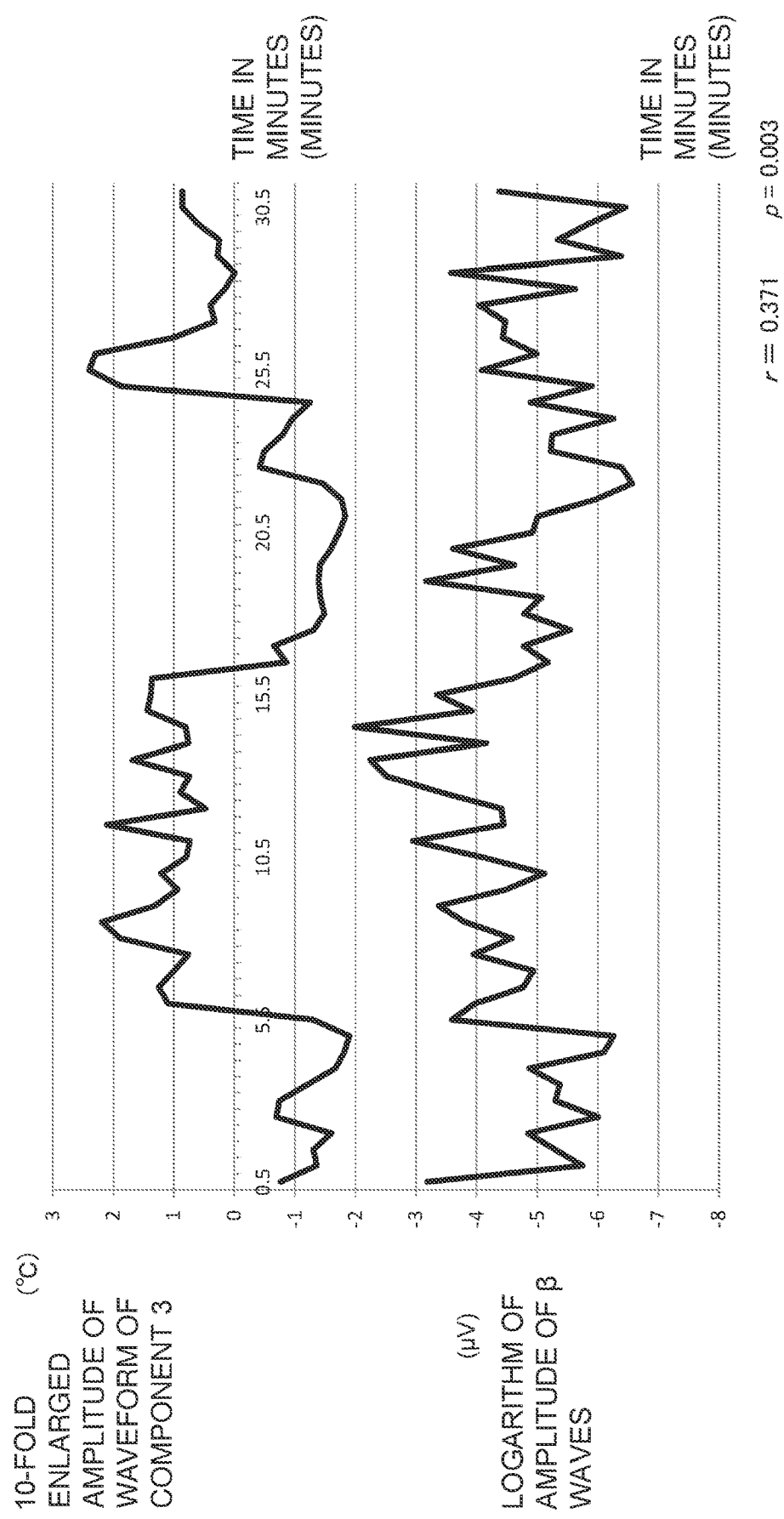
FIG. 5 is a diagram showing an amplitude of a component waveform of a component 3 and an amplitude of a $\beta$ wave among measured brain waves.
Figure 6A:
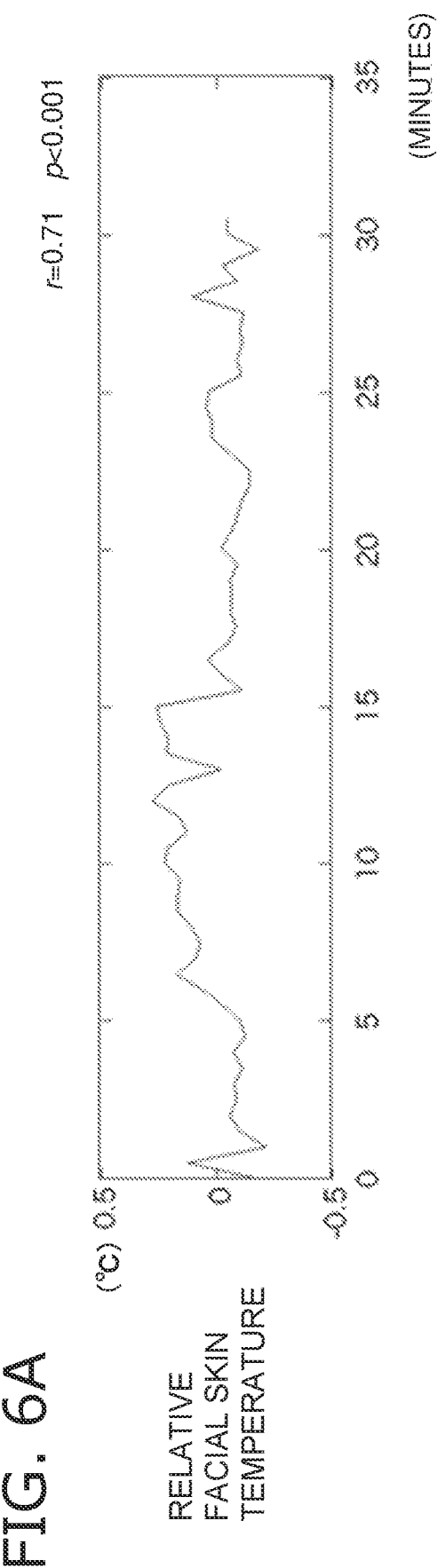
FIGS. 6A and 6B are diagrams showing part of the analysis result of the facial skin temperature data acquired in a control experiment.
Figure 6B:
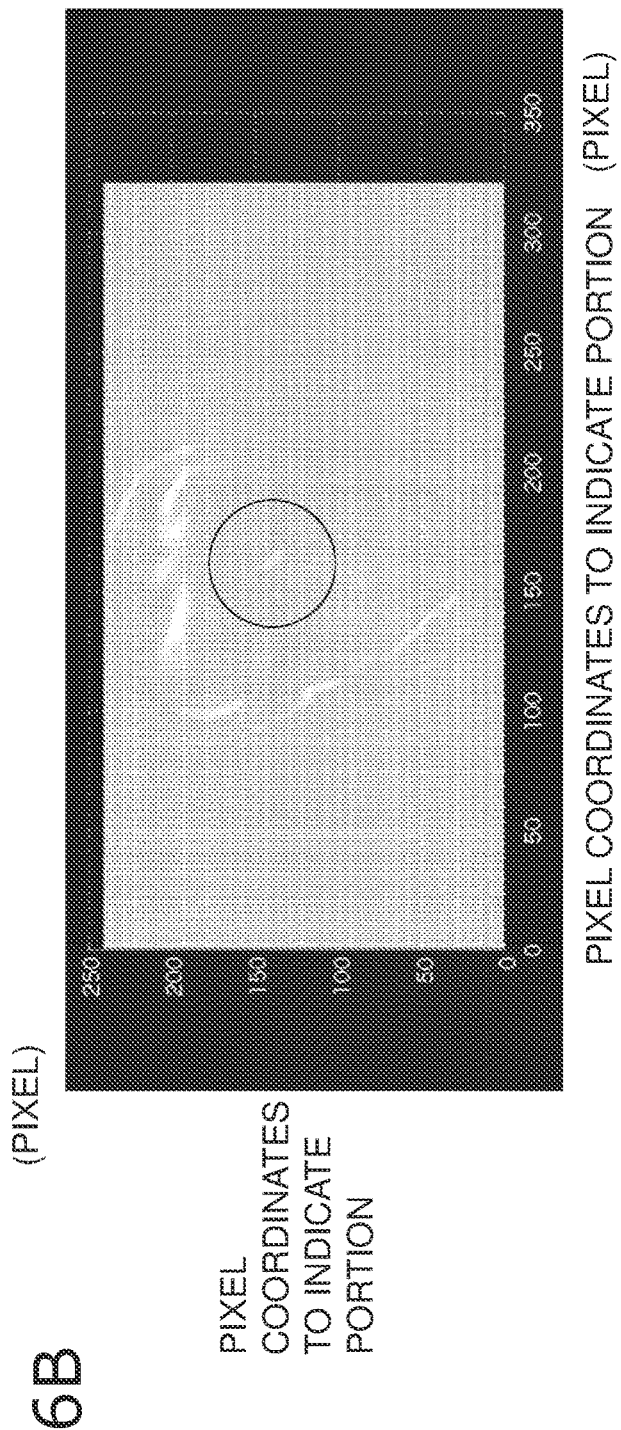

FIGS. 2A and 2B are diagrams showing parts of the analysis results of facial skin temperature data corresponding to temperature conversion data. FIG. 2A shows a component waveform diagram of a component 2 of a test subject 1. FIG. 2B shows a temperature distribution diagram of the component 2 of the test subject 1. FIG. 3A shows a component waveform diagram of a component 3 of the test subject 1. FIG. shows a temperature distribution diagram of the component 3 of the test subject 1. FIGS. 4 and 5 are diagrams showing the relationships between the amplitudes of the component waveforms and brain waves. FIG. 4 is a diagram showing the amplitude of a component waveform of the component 2 exhibited by the test subject 1 and the amplitude of β waves among measured brain waves. FIG. 5 is a diagram showing the amplitude of a component waveform exhibited by the component 3 of the test subject 1 and the amplitude of β waves of the measured brain waves. FIGS. 6A and 6B are diagrams showing parts of the analysis results of the facial skin temperature data acquired in a control experiment. FIG. 6A shows a component waveform diagram of the component 3. FIG. 6B shows a temperature distribution diagram of the component 3.

Table 1 shows analysis results of facial skin temperature data corresponding to each test subject.

From the results obtained by the analysis of the above-mentioned facial skin temperature data, a significant correlation was confirmed between the human brain activity and the component 2 and/or the component 3 among a plurality of components obtained by decomposing the time-series facial skin temperature data through the singular value decomposition.

TABLE 1

| | Correlation with data based on the absolute temperature conversion data | | Correlation with data based on relative temperature conversion data | |
|---|---|---|---|---|
| Test subject | Component waveform | Temperature distribution | Component waveform | Temperature distribution |
| Test subject 1 | Component 2 | Component 2 | Component 2 | Component 2 |
| | Component 3 | Component 3 | Component 3 | Component 3 |
| Test subject 2 | Component 3 | Component 3 | Component 3 | Component 3 |
| Test subject 3 | Component 1 | Component 2 | Component 2 | Component 2 |
| | Component 2 | Component 3 | Component 3 | Component 3 |
| | Component 3 | | | |
| Test subject 4 | Component 2 | Component 2 | Component 2 | Component 2 |
| | Component 3 | Component 3 | Component 3 | Component 3 |
| Test subject 5 | Component 2 | Component 2 | Component 2 | Component 2 |
| | Component 3 | Component 3 | Component 3 | Component 3 |
| Test subject 6 | Component 2 | Component 2 | Component 2 | Component 2 |
| | Component 5 | Component 5 | Component 5 | Component 5 |

As shown in FIGS. 4 and 5, from the results of the brain wave analysis, a significant correlation was confirmed between the amplitude of each of the component waveforms of the component 2 and the component 3 and the amplitude of the 03 waves of the brain waves.

In the control experiment, there was still a significant correlation between the component 3 and the human brain activity even in a state where the test subject was moving while the facial skin temperature data was being acquired (see FIG. 6). From this fact, it was confirmed that the component 3 among the plurality of components was not influenced by the movement of the test subject when the facial skin temperature data was acquired.

According to these results, the inventors have obtained the following findings.

The time-series facial skin temperature data acquired from the test subject was decomposed into a plurality of components by the singular value decomposition, and then each of the decomposed components was analyzed. As a result of this analysis, the component 3 among the plurality of components was confirmed to be a component related to the brain activity. That is, it has been found that the time-series facial skin temperature data is decomposed into a plurality of components by the singular value decomposition, subsequently a component having a correlation with the activation/non-activation of the brain is extracted from the plurality of decomposed components, and then the extracted component is analyzed using the selective brain cooling system, so that the component indicative of the change in the skin temperature which reflects the brain activity can be identified from the plurality of components. Accordingly, the inventors have obtained the finding that the brain activity can be estimated based on the human's facial skin temperature.

(3-2) Analysis Results of Photographed Image Data on the Facial Surface

Figure 7:
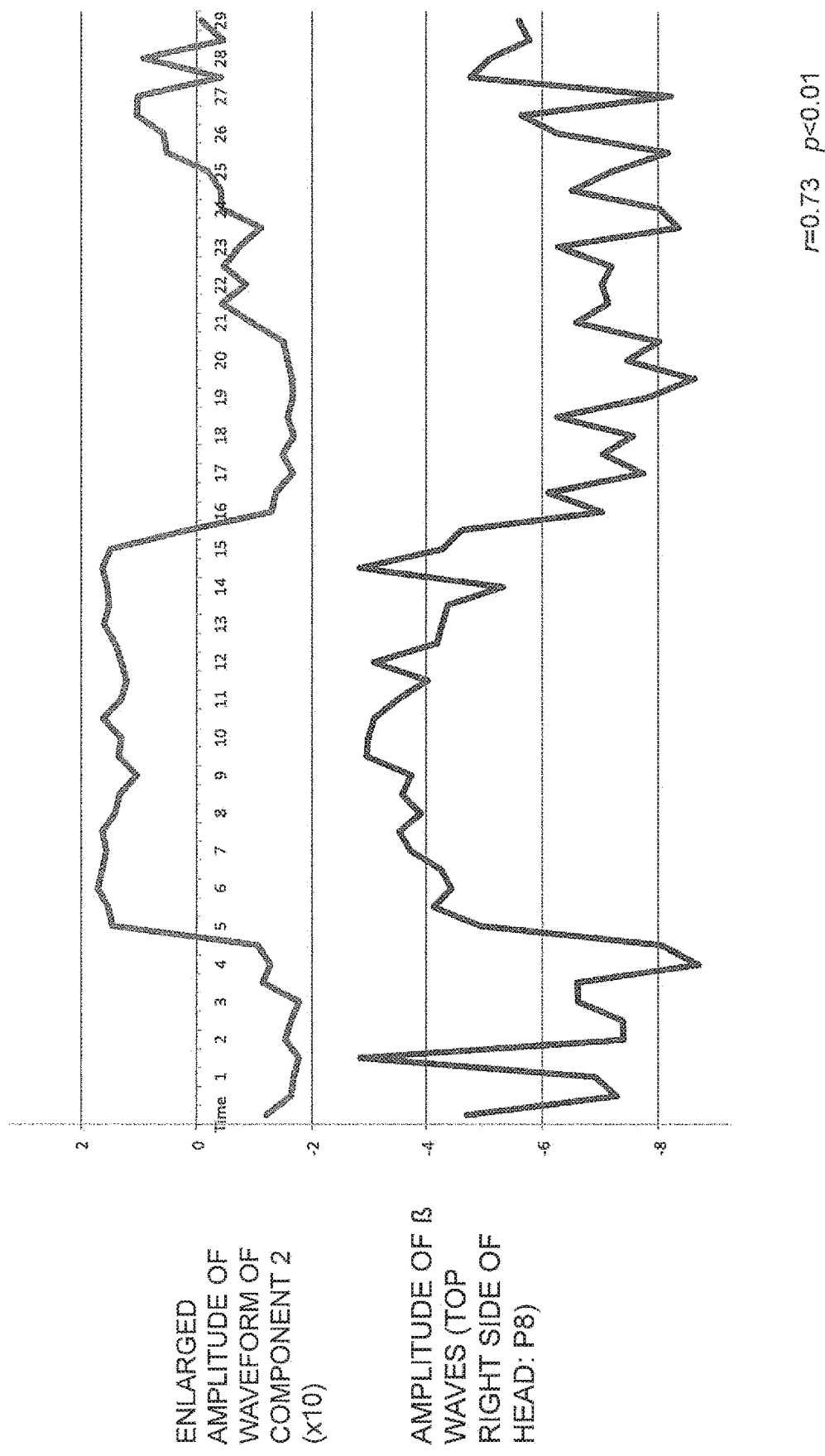
FIG. 7 is a diagram showing part of the analysis result of a component waveform based on the photographed image data on a facial surface.
Figure 8:
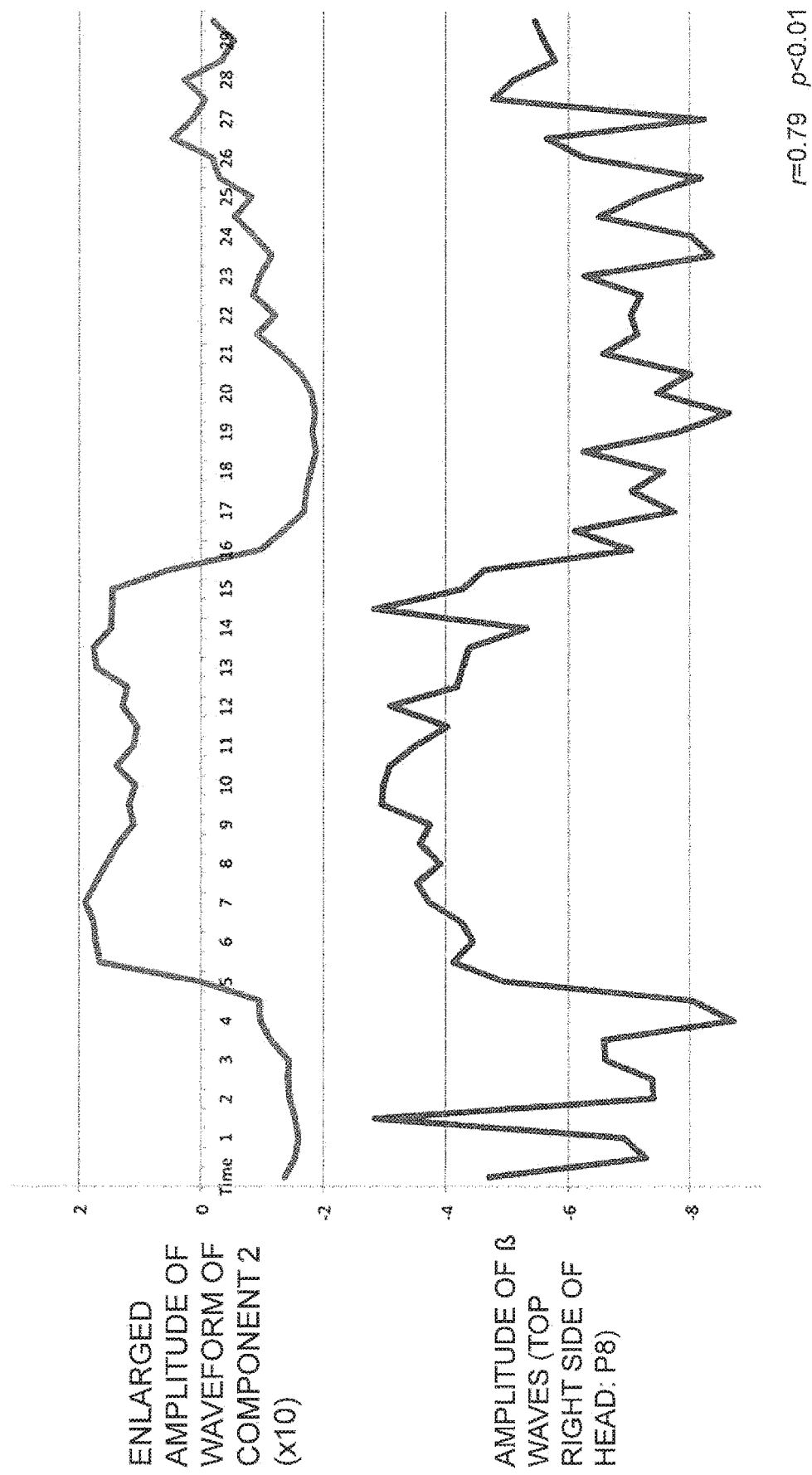
FIG. 8 is a diagram showing part of the analysis result of a component waveform based on the facial skin temperature data.
Figure 9:
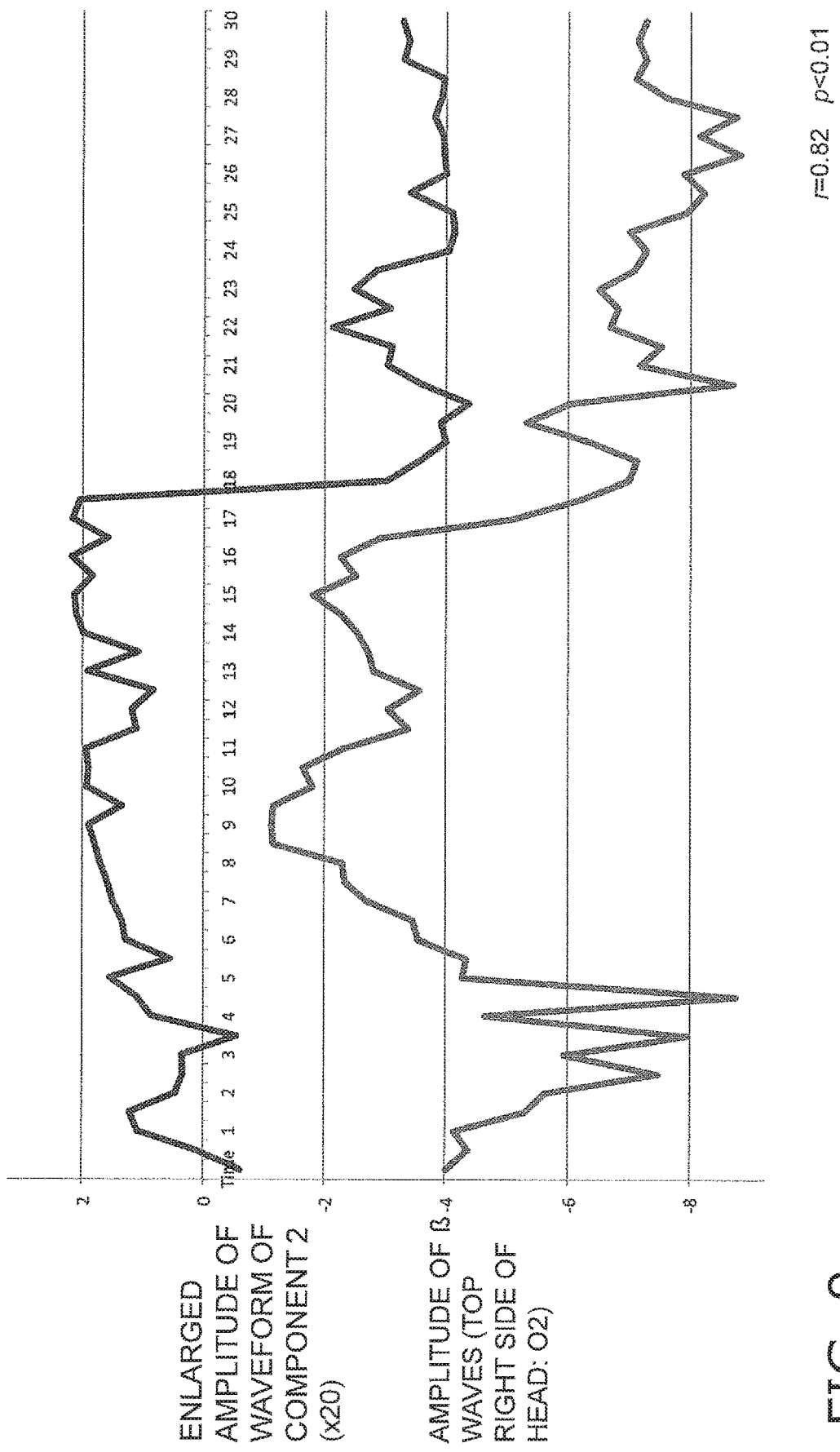
FIG. 9 is a diagram showing part of the analysis result of a component waveform based on the photographed image data on a facial surface.
Figure 10:
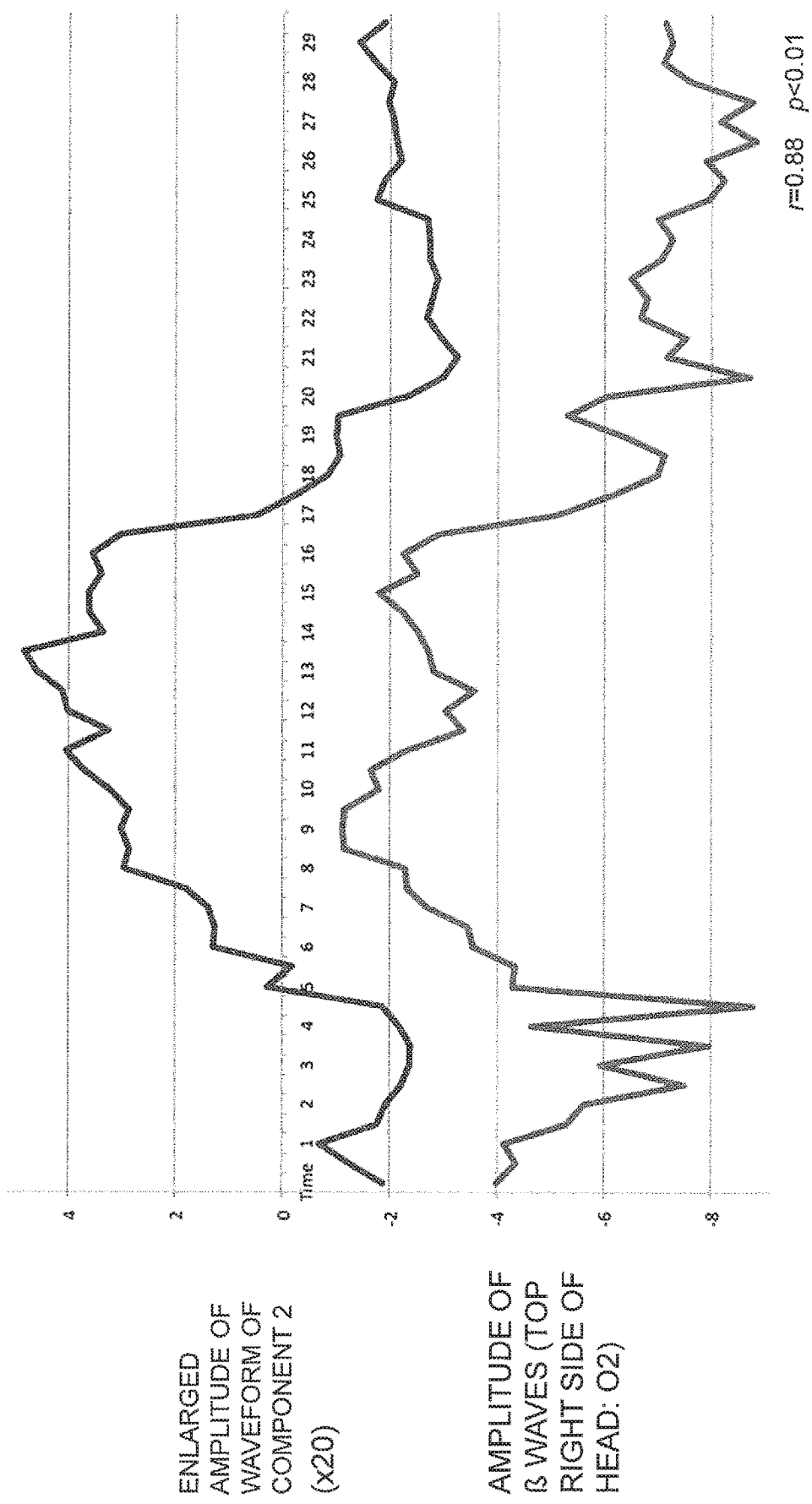
FIG. 10 is a diagram showing part of the analysis result of a component waveform based on the facial skin temperature data.
Figure 11:
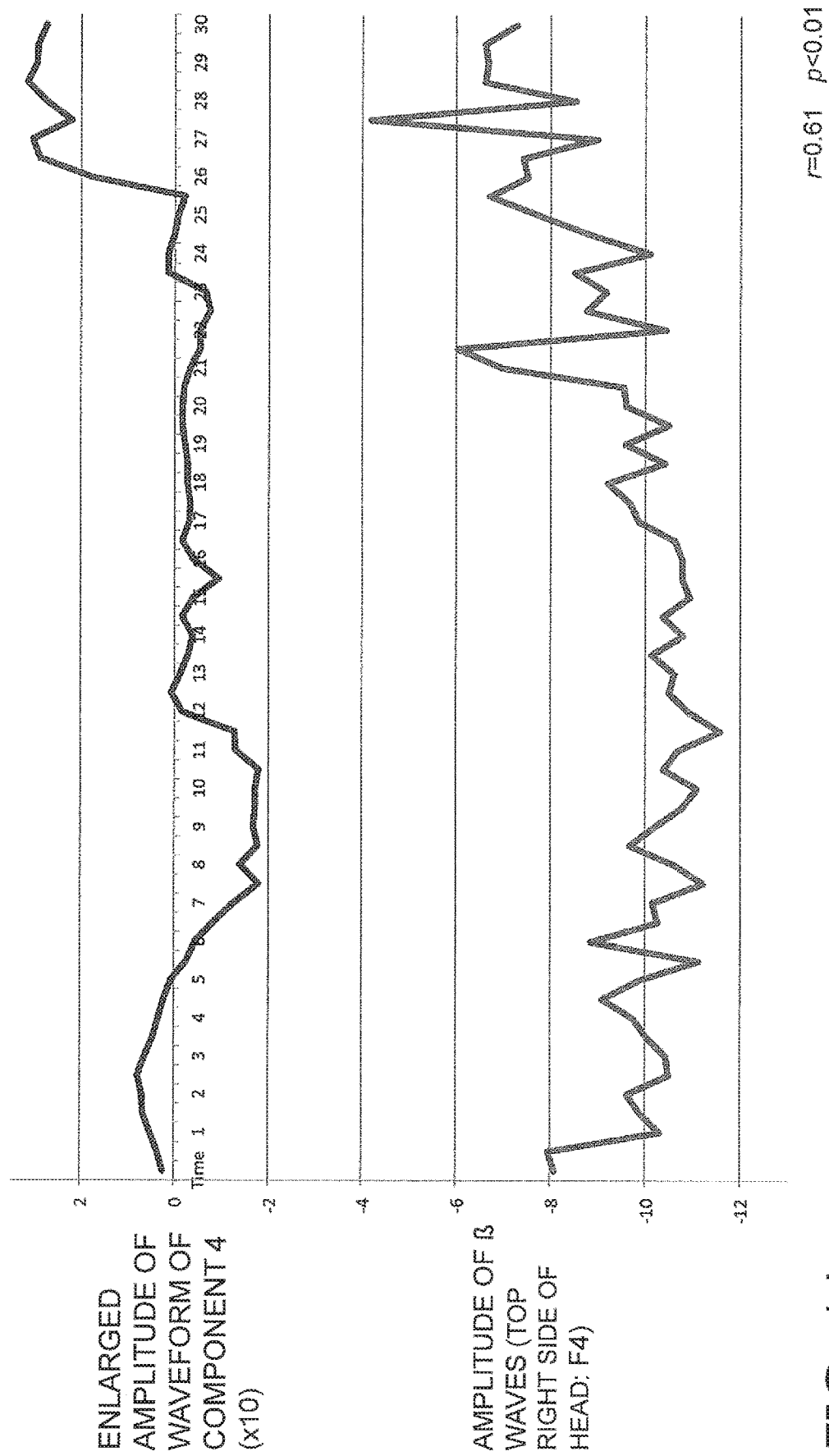
FIG. 11 is a diagram showing part of the analysis result of a component waveform based on the photographed image data on a facial surface.
Figure 12:
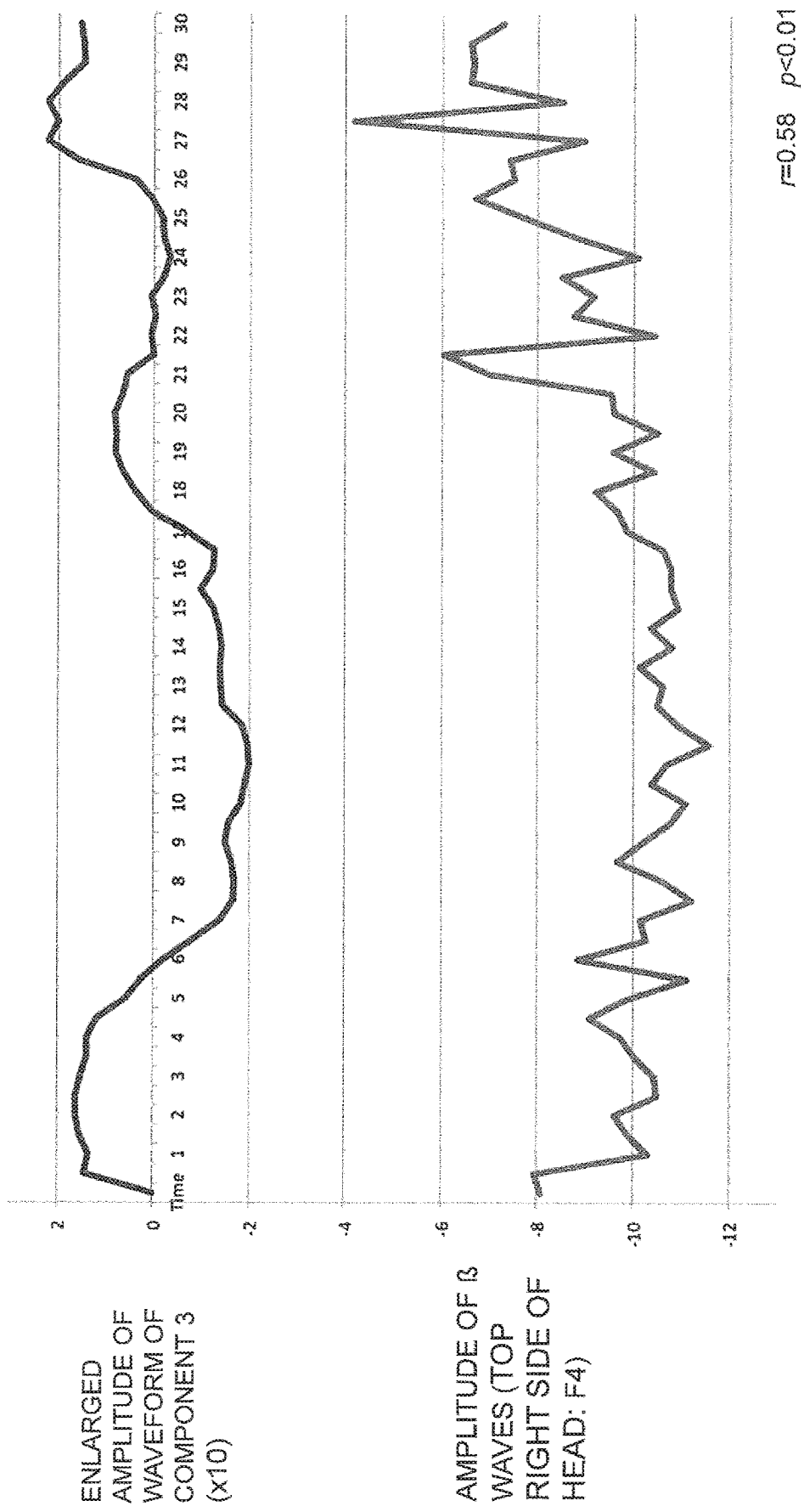
FIG. 12 is a diagram showing part of the analysis result of a component waveform based on the facial skin temperature data.
Figure 13:
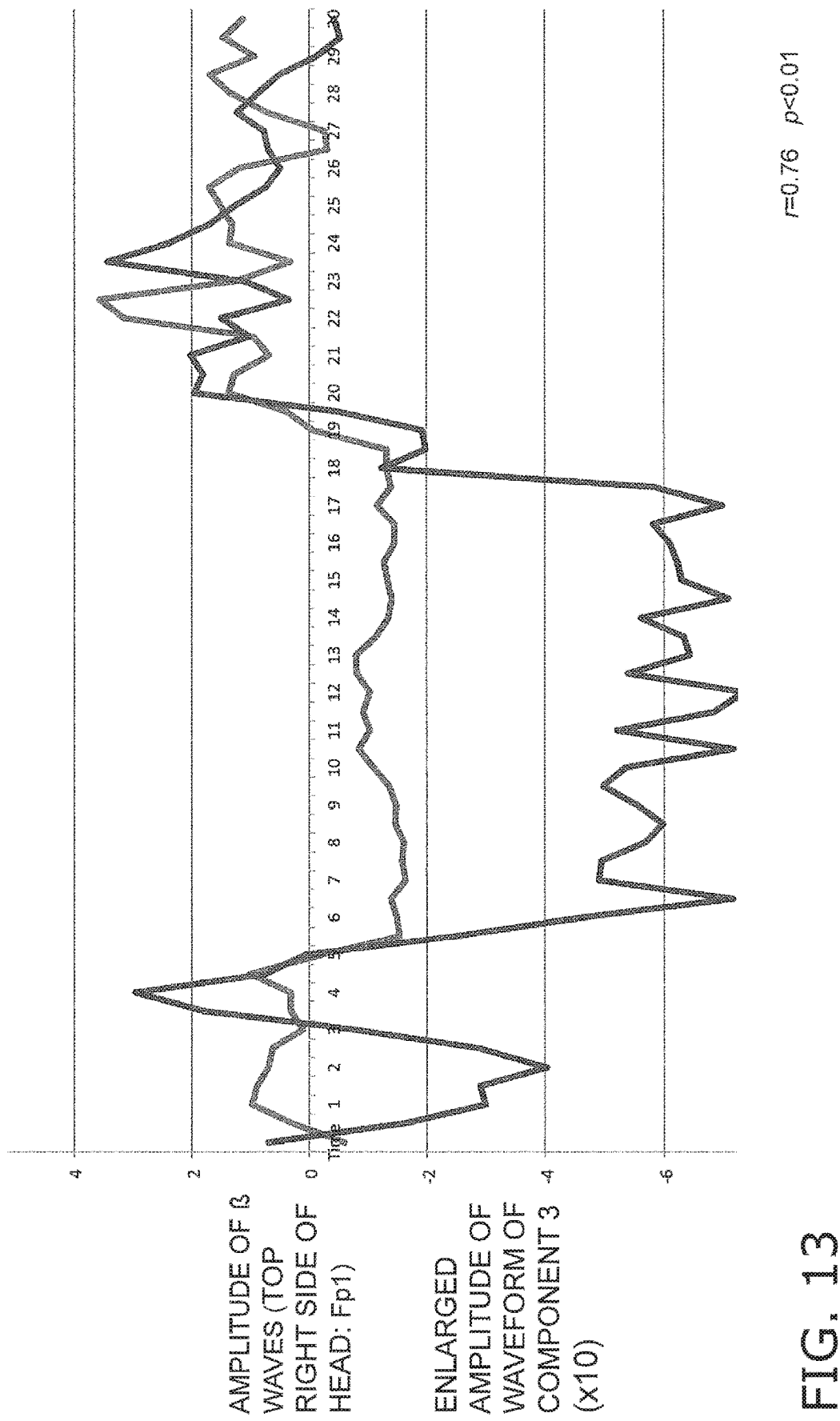
FIG. 13 is a diagram showing part of the analysis result of a component waveform based on the photographed image data on a facial surface.
Figure 14:
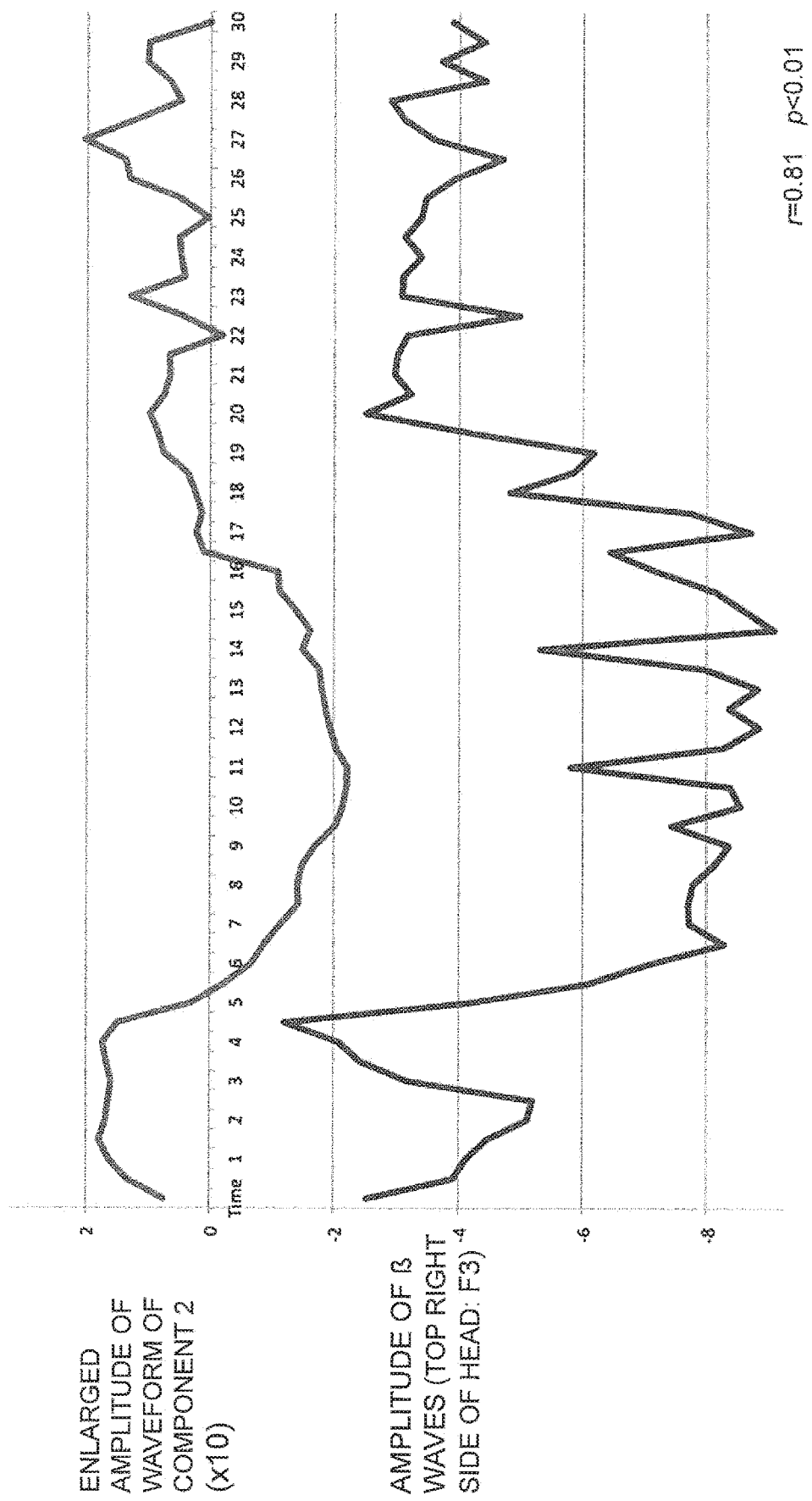
FIG. 14 is a diagram showing part of the analysis result of a component waveform based on the facial skin temperature data.
Figure 15:
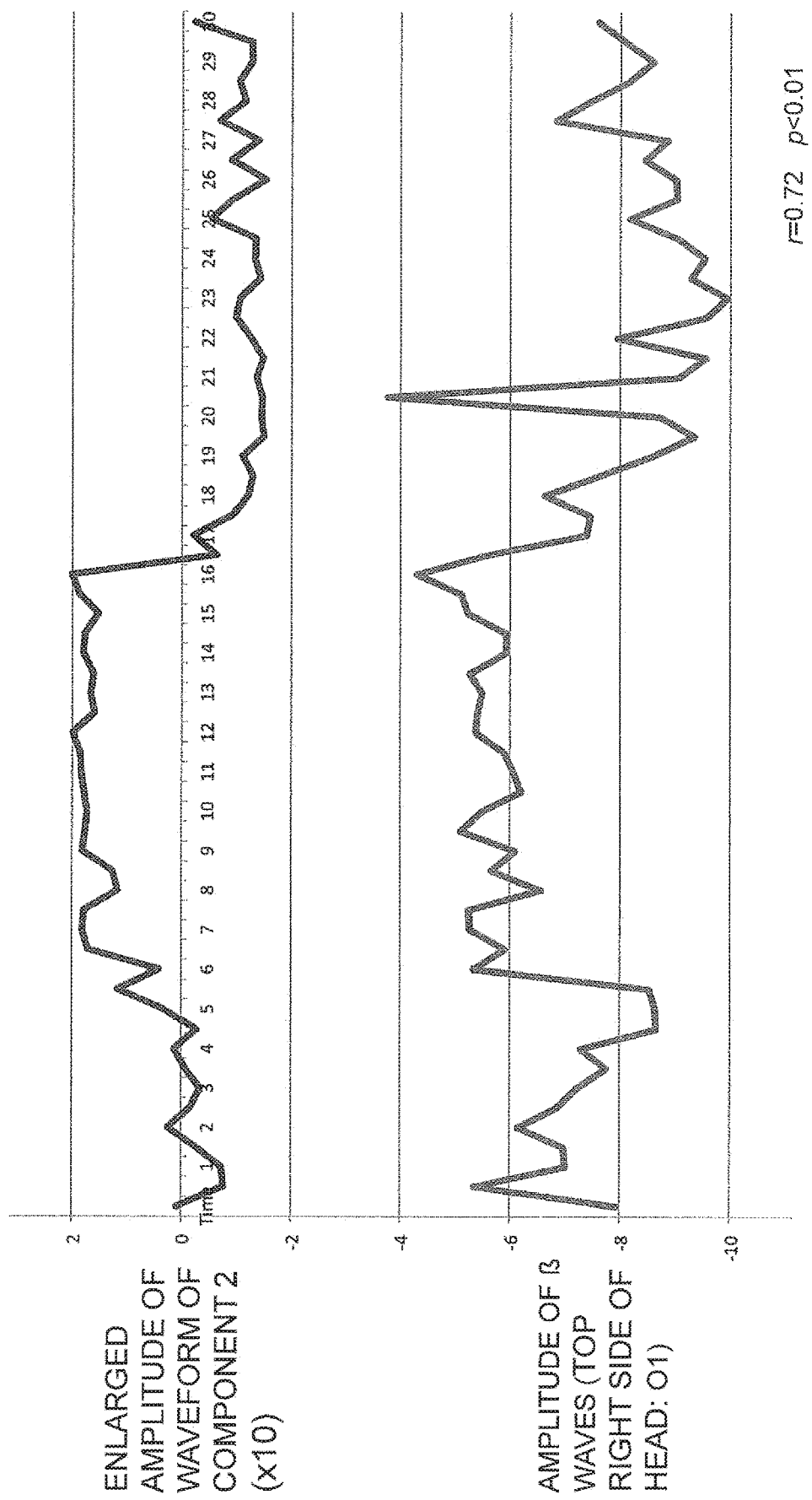
FIG. 15 is a diagram showing part of the analysis result of a component waveform based on the photographed image data on a facial surface.
Figure 16:
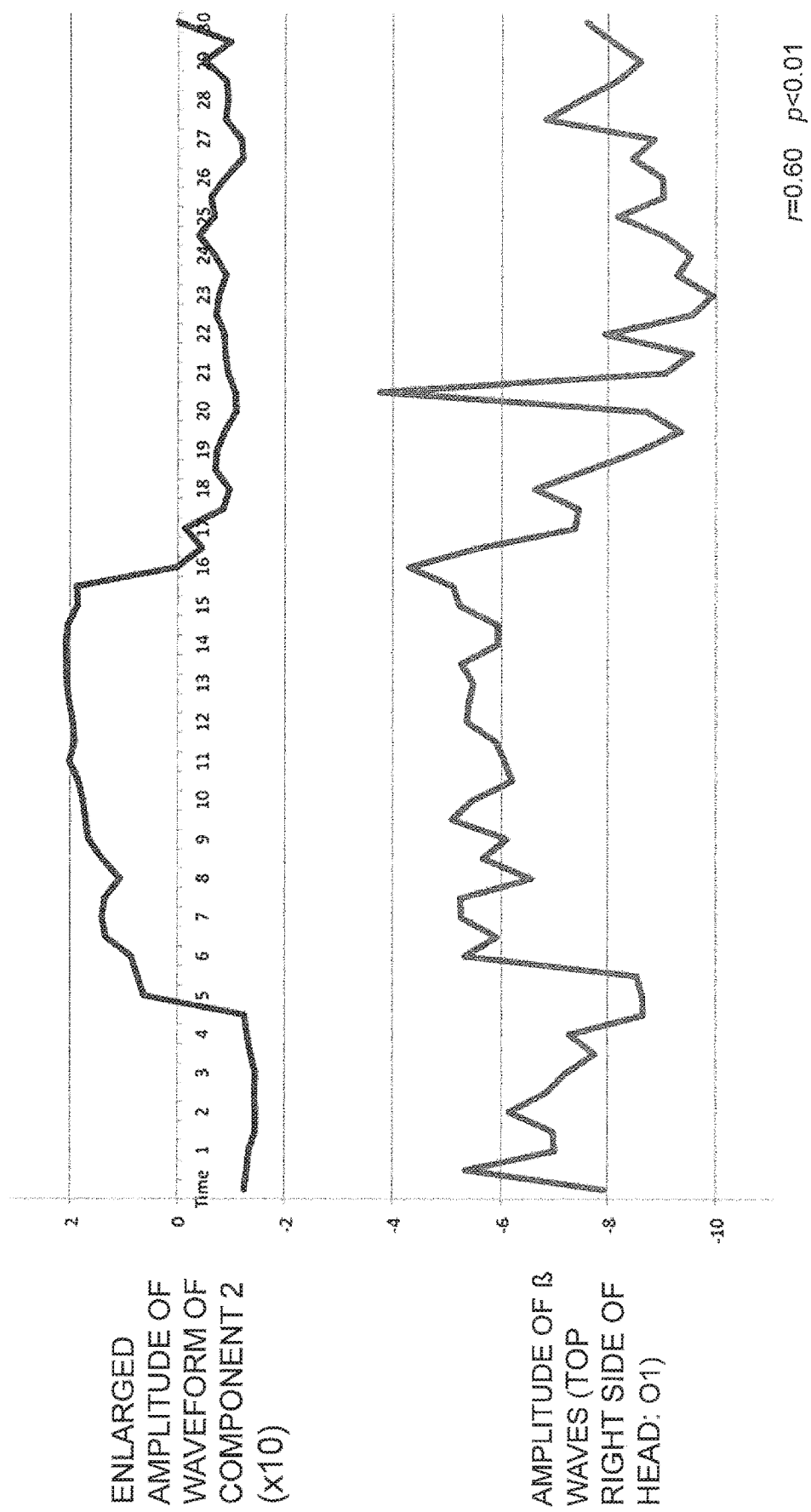
FIG. 16 is a diagram showing part of the analysis result of a component waveform based on the facial skin temperature data.
Figure 17:
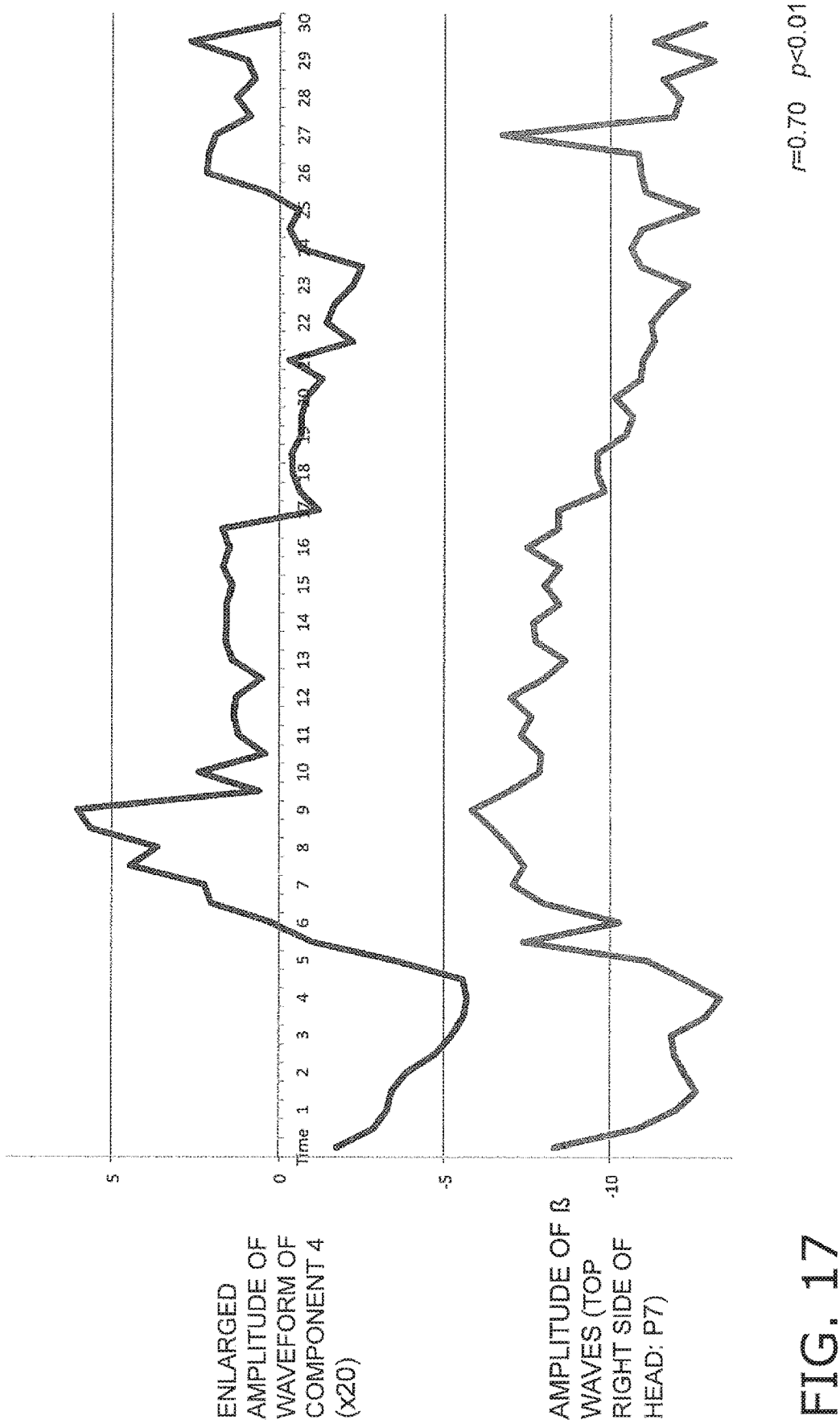
FIG. 17 is a diagram showing part of the analysis result of a component waveform based on the photographed image data on a facial surface.
Figure 18:
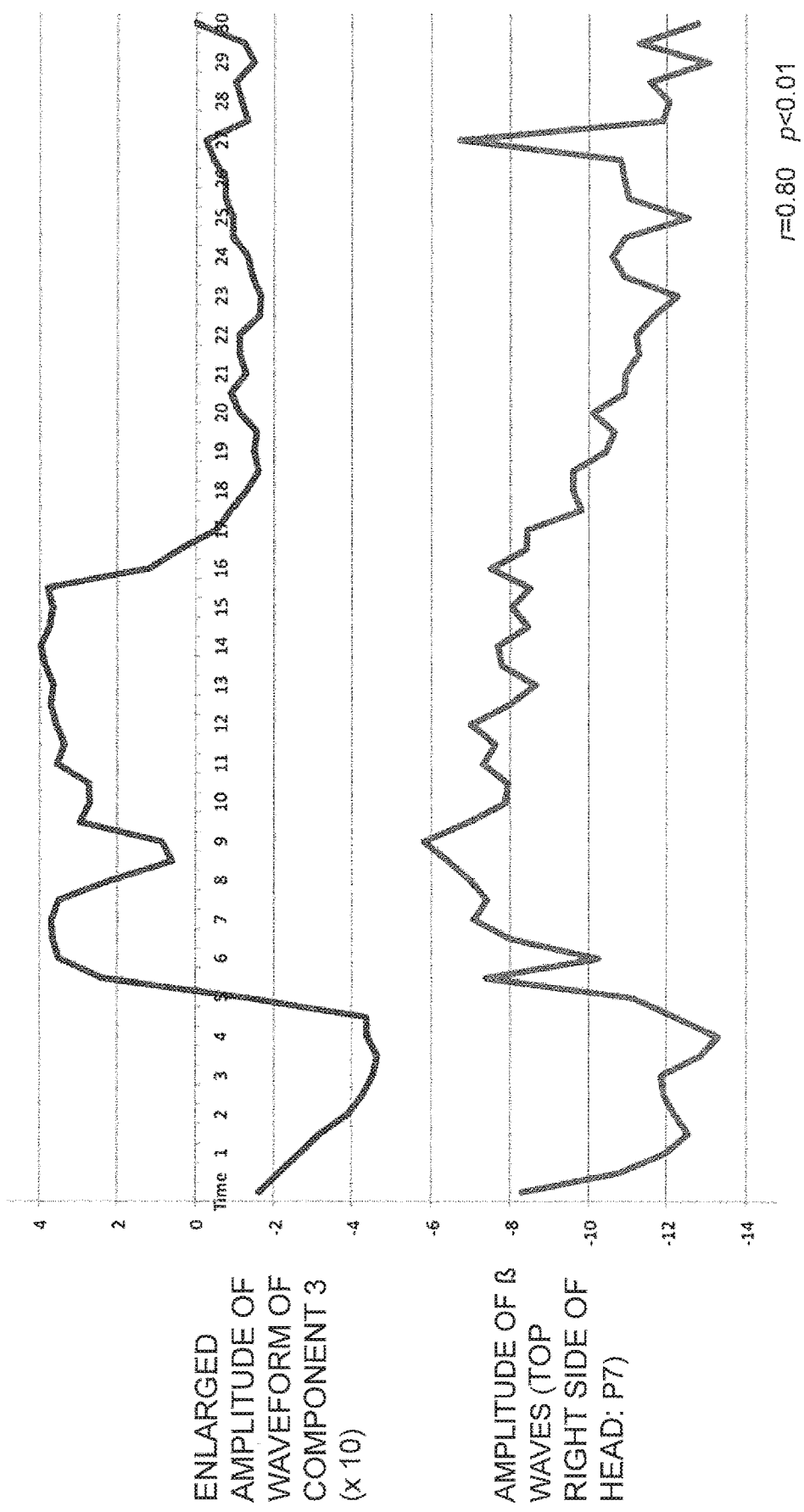
FIG. 18 is a diagram showing part of the analysis result of a component waveform based on the facial skin temperature data.

FIGS. 7 to 18 are diagrams showing parts of the analysis results of component waveform diagrams based on the photographed image data on the facial surface (blood-circulation-amount data) or the facial skin temperature data. FIG. 7 is a diagram showing the amplitude of a component waveform exhibited by the component 2 based on a photographed image data on the test subject 1 and the amplitude of β waves of the measured brain waves of the test subject 1. FIG. 8 is a diagram showing the amplitude of a component waveform exhibited by the component 2 based on the facial skin temperature data of the test subject 1 and the amplitude of β waves of the measured brain waves of the test subject 1. FIG. 9 is a diagram showing the amplitude of a component waveform exhibited by the component 2 based on a photographed image data on the test subject 2 and the amplitude of β waves of the measured brain waves of the test subject 2. FIG. 10 is a diagram showing the amplitude of a component waveform exhibited by the component 2 based on the facial skin temperature data of the test subject 2 and the amplitude of β waves of the measured brain waves of the test subject 2. FIG. 11 is a diagram showing the amplitude of a component waveform exhibited by the component 4 based on a photographed image data on the test subject 3 and the amplitude of β waves of the measured brain waves of the test subject 3. FIG. 12 is a diagram showing the amplitude of a component waveform exhibited by the component 3 based on the facial skin temperature data of the test subject 3 and the amplitude of β waves of the measured brain waves of the test subject 3. FIG. 13 is a diagram showing the amplitude of a component waveform exhibited by the component 3 based on a photographed image data on a test subject 4 and the amplitude of β waves among the measured brain waves of the test subject 4. FIG. 14 is a diagram showing the amplitude of a component waveform exhibited by the component 2 based on a facial skin temperature data on the test subject 4 and the amplitude of β waves of the measured brain waves of the test subject 4. FIG. 15 is a diagram showing the amplitude of a component waveform exhibited by the component 2 based on a photographed image data on a test subject 5 and the amplitude of β waves of the measured brain waves of the test subject 5. FIG. 16 is a diagram showing the amplitude of a component waveform exhibited by the component 2 based on the facial skin temperature data of the test subject 5 and the amplitude of β waves of the measured brain waves of the test subject 5. FIG. 17 is a diagram showing the amplitude of a component waveform exhibited by the component 4 based on a photographed image data on a test subject 6 and the amplitude of β waves of the measured brain waves of the test subject 6. FIG. 18 is a diagram showing the amplitude of a component waveform exhibited by the component 3 based on the facial skin temperature data of the test subject 6 and the amplitude of β waves of the measured brain waves of the test subject 6.

As shown in FIGS. 7 to 18, from the analysis results of each component waveform and the brain waves, the correlation was confirmed to be between the facial skin temperature and the facial blood circulation amount. Also in the analysis based on either of the facial skin temperature data and the facial blood-circulation-amount data, a significant correlation was confirmed between the amplitude of each component waveform and the amplitude of β waves of the brain waves measured by the electrodes attached onto the head top or occipital region.

Table 2 below shows the analysis results of the photographed image data on the facial surface of each test subject.

TABLE 2

| Test subject | Correlation with the blood-circulation-amount data | | Correlation with relative conversion blood-circulation-amount data | |
|---|---|---|---|---|
| | Component waveform | Blood circulation distribution | Component waveform | Blood circulation distribution |
| Test subject 1 | Component 2 | 0.72 | Component 1 | 0.59 |
| | | | Component 2 | 0.85 |
| Test subject 2 | Component 1 | 0.82 | Component 1 | 0.62 |
| | Component 2 | 0.82 | Component 2 | 0.60 |
| Test subject 3 | Component 2 | 0.33 | Component 2 | 0.45 |
| | Component 3 | 0.31 | Component 3 | 0.56 |
| | | | Component 4 | 0.56 |
| Test subject 4 | Component 1 | 0.57 | Component 1 | 0.66 |
| | Component 3 | 0.71 | Component 3 | 0.65 |
| Test subject 5 | Component 1 | 0.56 | Component 1 | 0.51 |
| | Component 2 | 0.72 | Component 2 | 0.83 |
| Test subject 6 | Component 2 | 0.38 | Component 2 | 0.45 |
| | Component 4 | 0.68 | Component 3 | 0.51 |
| | | | Component 5 | 0.36 |

As shown in Table 2, from the results obtained by the analysis of the above-mentioned photographed image data, significant correlations were confirmed between the human brain activity and the components 1, 2, 3, 4, and 5 among a plurality of components obtained by decomposing the time-series blood-circulation-amount data based on the photographed image data on the facial surface by singular value decomposition. Here, the components identified as having the significant correlation with the human brain activity include, in addition to a component having the significant correlation therewith in terms of both the blood-circulation-amount data and the relative conversion blood-circulation-amount data, a component having the significant correlation therewith in terms of the relative conversion blood-circulation-amount data but not the blood-circulation-amount data.

Furthermore, Table 3 below shows the results of the control experiment.

TABLE 3

| | |
|---|---|
| Component having correlation with rest/activation of the brain | Component 1 |
| | Component 2 |
| Component having correlation with a moving distance of the facial surface | Component 1 |
| | Component 3 |
| | Component 4 |
| Component having correlation with the number of inputs into a keyboard | Component 8 |

As shown in Table 3, in the control experiment, when the test subject moved while acquiring a photographed image data on the facial surface, the component 2 was one of the components that had a significant correlation between the amplitude of its component waveform and each of the brain activation time and the brain non-activation time. However, the component 2 was not confirmed to have a significant correlation with each of the movement distance and the number of inputs into the keyboard. From this fact, it has been that among the components obtained by conducting the singular value decomposition on the blood-circulation-amount data based on the RGB data acquired from the photographed image data on the facial surface, the component having a significant correlation with the brain activity is hardly influenced by the movement of the test subject even if the test subject moves in acquiring the time-series photographed image data on the facial surface, as compared with the influence of the brain activity on the component (influence by the activation or non-activation of the brain).

From these results, the inventors have obtained the following findings.

The blood-circulation-amount data acquired from the facial RGB data based on the time-series photographed image data on the facial surface, acquired from the test subject, was decomposed into a plurality of components by the singular value decomposition, and then each of the decomposed components was analyzed. As a result of this analysis, the components 1, 2, 3, 4, and 5 among the plurality of components were confirmed to be related to the brain activity. That is, it has been found that the blood-circulation-amount data acquired from the facial RGB data based on the time-series photographed image data on the facial surface is decomposed into a plurality of components by the singular value decomposition, subsequently a component having a correlation with the activation/non-activation of the brain is extracted from the plurality of decomposed components, and then the extracted component is analyzed, so that the component indicative of the RGB change on the facial surface which reflects the brain activity can be identified from the plurality of components. Accordingly, the inventors have obtained the finding that the brain activity can be estimated based on the time-series photographed image data on the human's facial surface.

(4) Brain Activity Visualization Device

Next, a description will be given on brain activity visualization devices 10 and 110 according to an embodiment of the present invention that has completed by the inventors based on the findings described above. Note that the brain activity visualization device according to the present invention is not limited to the following embodiments, and various modifications and changes can be made to the embodiments without departing from the scope and spirit of the present invention.

Brain activity visualization devices 10 and 110 according to an embodiment of the present invention include a brain activity estimation means 30 for estimating the brain activity based on the facial skin temperature data and/or a brain activity estimation means 130 for estimating the brain activity based on the photographed image data on the facial surface. Hereinafter, first, the respective brain activity estimation means 30 and 130 will be described before explaining the brain activity visualization devices 10 and 110 according to the embodiment of the present invention.

Figure 19:
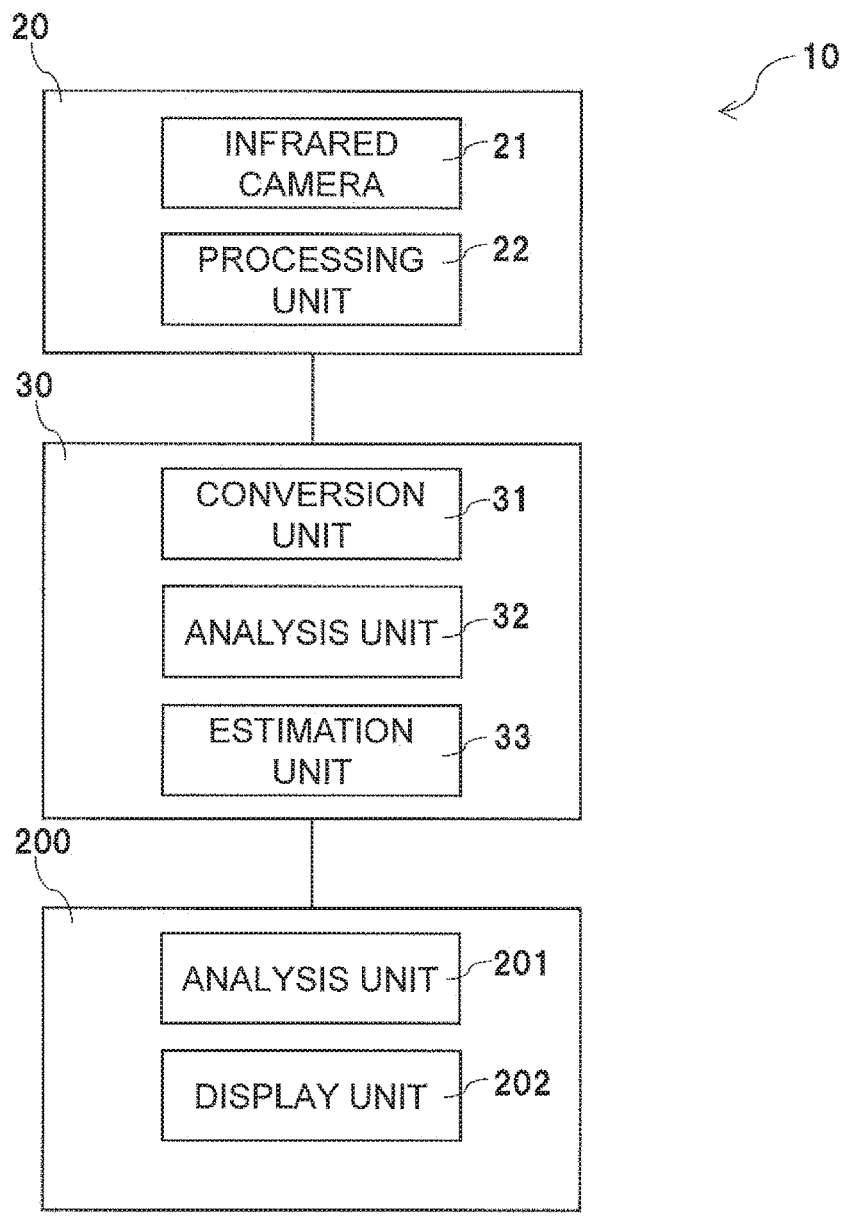
FIG. 19 is an exemplary diagram of a brain activity visualization device according to an embodiment of the present invention.
Figure 20:
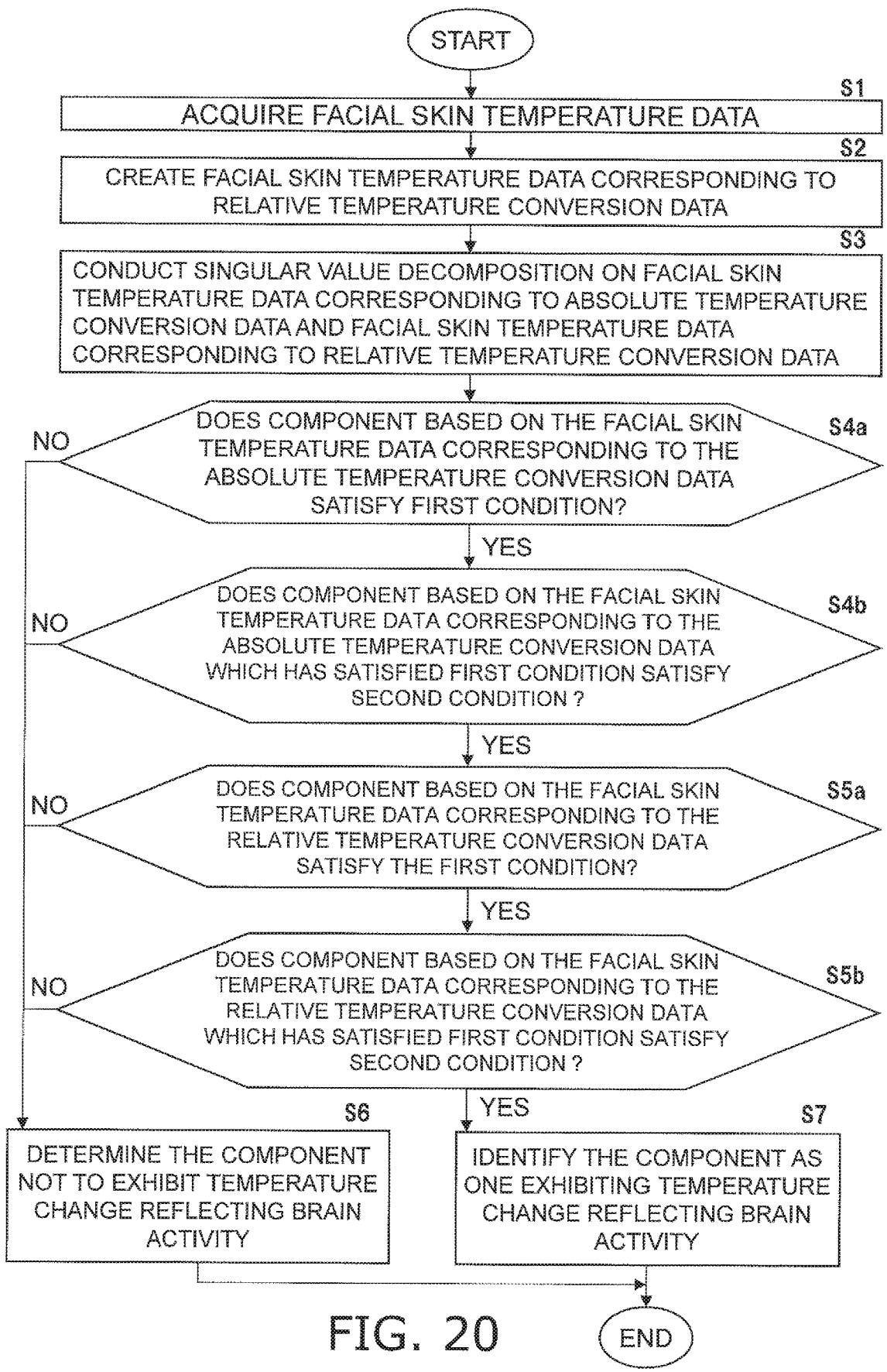
FIG. 20 is a flowchart showing a flow of processing performed in identifying a component indicative of a change in the skin temperature reflecting a brain function in the brain activity visualization device.

(4-1) Brain Activity Estimation Means 30 for Estimating the Brain Activity Based on the Facial Skin Temperature Data FIG. 19 is an exemplary diagram of a brain activity visualization device 10 according to an embodiment of the present invention. FIG. 20 is a flowchart showing the flow of processing performed in the case of identifying a component indicative of a change in the skin temperature that reflects the brain function in the brain activity visualization device 10.

The brain activity estimation means 30 included in the brain activity visualization device 10 estimates the brain activity of an individual (test subject) from the facial skin temperature of the individual. As shown in FIG. 19, the brain activity visualization device 10 includes facial skin temperature acquisition means 20, the brain activity estimation means 30, and state visualization means 200.

The facial skin temperature acquisition means 20 detects the skin temperature of at least a part of the facial surface of the individual, and acquires facial skin temperature data including the detected temperature data and position data regarding a detected part in time series (step S1). Here, the facial skin temperature acquisition means 20 is an infrared thermography device, and includes an infrared camera 21 and a processing unit 22, as shown in FIG. 19. The infrared camera 21 is for detecting infrared radiant energy emitted from the face of the individual. Here, it is assumed that the infrared camera 21 detects infrared radiant energy from the entire face of the individual. The processing unit 22 converts the infrared radiant energy detected by the infrared camera 21 into a corresponding temperature to create temperature data. Then, the processing unit 22 creates a temperature distribution diagram of the facial skin temperatures on the entire facial surface by assigning the parts at which the infrared radiant energy is detected to position data (coordinate data). Ultimately, the processing unit 22 processes the created temperature distribution diagram into facial skin temperature data corresponding to the temperature conversion data. The facial skin temperature data corresponding to the temperature conversion data is stored in a storage unit (not shown) included in the processing unit 22.

Here, the processing unit 22 creates the temperature distribution diagram of the facial skin temperatures across the entire facial surface, but is not limited thereto. Alternatively, the temperature distribution diagram of the temperature of the facial skin including at least the paranasal sinus peripheral region and/or forehead may be created, and this diagram may be handled as the facial skin temperature data corresponding to the temperature conversion data.

Here, while the facial skin temperature data corresponding to the temperature conversion data is being acquired by the facial skin temperature acquisition means 20, the brain function activation task is given to the individual for a certain period of time. That is, the facial skin temperature data corresponding to the temperature conversion data acquired by the facial skin temperature acquisition means 20 includes the data generated for a time period during which the brain function activation task is given to the individual. Note that the brain function activation task given to the individual is not particularly limited as long as it is estimated to bring the brain into the activated state. For example, the brain function activation task may be configured to have its contents determined as appropriate in accordance with the purpose of use of the brain activity visualization device 10.

The brain activity estimation means 30 estimates the human brain activity based on the facial skin temperature data corresponding to the temperature conversion data acquired by the facial skin temperature acquisition means 20. Specifically, as shown in FIG. 19, the brain activity estimation means 30 includes a conversion unit 31, an analysis unit 32, and an estimation unit 33.

The conversion unit 31 converts the temperature data included in the facial skin temperature data corresponding to the temperature conversion data, into relative temperature data, and generates facial skin temperature data based on the converted relative temperature data, that is, facial skin temperature data corresponding to the relative temperature conversion data (step S2). Specifically, the conversion unit 31 sets an average value of the temperature data included in the facial skin temperature data corresponding to the temperature conversion data every predetermined time (for example, 30 seconds) as a reference value, and then converts the temperature data into the relative temperature data. The conversion unit 31 generates the facial skin temperature data corresponding to the relative temperature data by using the converted relative temperature data and the position data.

The analysis unit 32 decomposes each of the facial skin temperature data corresponding to the time-series temperature conversion data and the facial skin temperature data corresponding to the relative temperature conversion data, into a plurality of components by the singular value decomposition, principal component analysis, or independent component analysis (step S3). Here, the analysis unit 32 conducts the singular value decomposition on the acquired facial skin temperature data corresponding to the temperature conversion data as well as the converted facial skin temperature data corresponding to the relative temperature conversion data, by using the SVD of MATLAB (registered trademark) as the analysis tool. In the singular value decomposition, for the facial skin temperature data corresponding to the temperature conversion data acquired in time series as well as the facial skin temperature data corresponding to the relative temperature conversion data, the factor was defined as time data acquired every predetermined time period (for example, 30 seconds), and the measure was defined as the facial skin temperature data corresponding to the temperature conversion data in that time period and the facial skin temperature data corresponding to the relative temperature conversion data. By the singular value decomposition, each of the facial skin temperature data corresponding to the temperature conversion data and the facial skin temperature data corresponding to the relative temperature conversion data was decomposed into a plurality of components, and then a time distribution and a space distribution of each component and a singular value indicative of the size of each component were calculated.

Further, the analysis unit 32 determines whether or not each component satisfies a first condition and a second condition in order to identify the component indicative of the change in the skin temperature that reflects the brain activity, from the plurality of components decomposed by the singular value decomposition (step S4a, step S4b, step S5a, and step S5b). Here, first, the analysis unit 32 determines whether the first condition is satisfied by each of the components based on the facial skin temperature data corresponding to the temperature conversion data (step S4a). Then, it is determined whether the second condition is satisfied by the component based on the facial skin temperature data corresponding to the temperature conversion data which has been determined to satisfy the first condition in step S4a (step S4b). Subsequently, it is determined whether or not the first condition is satisfied by only a component(s) that is identical to a component(s) determined to satisfy both the first and second conditions in steps S4a and S4b, among respective components based on the facial skin temperature data corresponding to the relative temperature conversion data (step S5a). Then, it is determined whether the second condition is satisfied by the component based on the facial skin temperature data corresponding to the relative temperature conversion data and which has been determined to satisfy the first condition in step S5a (step S5b). Note that the order of the determination conducted by the analysis unit 32 is not limited thereto. Alternatively, for example, it is determined whether or not each component based on the facial skin temperature data corresponding to the temperature conversion data as well as each component based on the facial skin temperature data corresponding to the relative temperature conversion data satisfy the first condition and the second condition respectively, and finally the components whose determination results are identical to each other may be extracted.

The first condition is that the amplitude of the component waveform of a component obtained by the singular value decomposition has a correlation with changes of the brain in the non-activation time and the activation time. The analysis unit 32 extracts the component satisfying the first condition as a determination component from the plurality of components. Here, while the facial skin temperature data corresponding to the temperature conversion data is being acquired, the brain function activation task is given to the individual for a certain time period. The analysis unit 32 defines a time period during which the brain function activation task is not given to the individual as the brain non-activation time, and also defines a time period during which the brain function activation task is given to the individual as the brain activation time. Then, the analysis unit 32 compares the component waveform of each component with each of the brain non-activation time and the brain activation time. The analysis unit 32 evaluates whether or not there is a correlation between the component waveform of each component and each of the brain non-activation time and the brain activation time, using the comparison analysis results based on the component waveform data. Then, the analysis unit 32 extracts the component which has been evaluated to have a correlation, from the plurality of components as a determination component satisfying the first condition. Meanwhile, the analysis unit 32 evaluates that a component(s) among the plurality of components does not have any correlation. Then, the analysis unit 32 determines the evaluated component not to exhibit the temperature change reflecting the human brain activity while not satisfying the first condition (step S6).

Here, the brain function activation task is given to the individual for a certain period of time in acquiring the facial skin temperature data corresponding to the temperature conversion data. Based on this result, the analysis unit 32 extracts a determination component. However, the contents of the first condition, i.e., the extraction means of the determination component in the analysis unit 32 are not limited thereto. For example, when a component that exhibits the component waveform having a correlation with the brain non-activation time and the brain activation time is specified from among the plurality of components by conducting experiments or the like in advance, the analysis unit 32 extracts the specified component from the plurality of components as the determination component. In addition, when a human's movement known to be related to the activation/non-activation of the brain, such as eye movement or blink, is detected on the present brain activity visualization device, the analysis unit 32 may compare, analyze, and evaluate the detection result and the component waveform of each component, thereby extracting the determination component from the plurality of components. Note that the criterion for the analysis unit 32 to determine whether the first condition is satisfied or not is decided as appropriate by simulation, experiments, desk calculation, or the like in accordance with the purpose of use of the brain activity visualization device 10 or the like.

The second condition is that regarding the extracted determination component, there is a temperature change in a predetermined part on the human's facial surface. The analysis unit 32 determines a component satisfying the second condition among the determination components as a component having a high possibility of being related to the human brain activity, and extracts this component as a candidate component. That is, the analysis unit 32 determines whether or not the determination component is related to the human brain activity based on the presence or absence of a temperature change in a predetermined part of the human's facial surface. Specifically, the analysis unit 32 determines whether or not a temperature change occurs in the paranasal sinus peripheral region and/or the forehead based on the temperature distribution data regarding the extracted determination component. Then, if the temperature change occurs there, the analysis unit 32 determines that the determination component is a component that satisfies the second condition and which has a high possibility of being related to human brain activity, and extracts this component as a candidate component. On the other hand, when the temperature change does not occur in the paranasal sinus peripheral region and/or the forehead, the analysis unit 32 determines that the determination component does not satisfy the second condition and does not exhibit a change in the skin temperature that reflects the brain activity (step S6). Note that the criterion for the analysis unit 32 to determine whether the second condition is satisfied or not is determined as appropriate by simulation, experiments, desk calculation, or the like in accordance with the purpose of use of the brain activity visualization device 10 or the like.

Then, the analysis unit 32 identifies the component determined to satisfy the second condition in step S5b as a component indicative of the change in the skin temperature reflecting the brain activity (step S7). That is, the component identified as the component reflecting the brain activity and indicating the change in the skin temperature in step S7 achieves the fact that the candidate component extracted by decomposing and analyzing the facial skin temperature data corresponding to the temperature conversion data by singular value decomposition is identical to the candidate component extracted by decomposing and analyzing the facial skin temperature data corresponding to the relative temperature conversion data by the singular value decomposition. It should be noted that the candidate components which are extracted in both analysis steps and are not identical with each other are determined not to indicate the change in the skin temperature reflecting the brain activity in step S6.

The estimation unit 33 estimates the human brain activity based on the component identified by the analysis unit 32 as the component indicative of the change in the skin temperature reflecting the human brain activity. Specifically, the estimation unit 33 estimates an amount of brain activity when the facial skin temperature data is acquired based on the component waveform data regarding the component identified by the analysis unit 32.

(4-1-1) Modified Example 1A

The brain activity estimation means 30 includes the conversion unit 31, and generates the facial skin temperature data corresponding to the relative temperature conversion data by the conversion unit 31. The analysis unit 32 decomposes not only the facial skin temperature data corresponding to the temperature conversion data acquired by the facial skin temperature acquisition means 20, but also the facial skin temperature data corresponding to the relative temperature data based on the temperature data converted to the relative temperature data, into a plurality of components by the singular value decomposition. Then, the analysis unit 32 analyzes these decomposed respective components.

Instead of this, the brain activity estimation means 30 may not include the conversion unit 31. In this case, the elimination of the conversion unit 31 makes it possible to omit the processing of generating the facial skin temperature data corresponding to the relative temperature conversion data or analyzing the data based on the facial skin temperature data corresponding to the relative temperature conversion data.

To identify the component related to the human brain activity with high accuracy, however, it is desirable that the brain activity estimation means 30 includes the conversion unit 31, like the above-mentioned embodiment. Furthermore, the analysis unit 32 decomposes the facial skin temperature data corresponding to the temperature conversion data acquired by the facial skin temperature acquisition means 20 and also decomposes the facial skin temperature data corresponding to the relative temperature data based on the temperature data converted to the relative temperature data, into a plurality of components by the singular value decomposition. In addition, the analysis unit 32 analyzes these decomposed components.

(4-1-2) Modified Example 1B

The facial skin temperature acquisition means 20 is an infrared thermography device capable of acquiring the temperature data in a non-contact state with an object.

However, the facial skin temperature acquisition means is not limited to the infrared thermography device as long as this means can detect the skin temperature of at least a part of the individual's facial surface and can acquire the facial skin temperature data including the detected temperature data and the position data on the detected part in time series.

For example, the facial skin temperature acquisition means may be a device including a temperature sensor. Specifically, a temperature sensor may be attached to a predetermined part of an individual's facial surface, and time-series facial skin temperature data may be acquired based on temperature data detected by the temperature sensor and position data of the part where the temperature sensor is attached. In this way, the temperature sensor does not require a preprocessing before attachment, unlike brain wave electrodes or the like, even when the facial skin temperature data is acquired with the temperature sensor being in contact with a target individual. Thus, the temperature sensor can easily acquire the data, as compared with conventional detection methods, such as an electroencephalography method, a magnetic resonance imaging method, and a near infrared spectroscopy method. Consequently, the human brain activity can be easily estimated.

Figure 21:
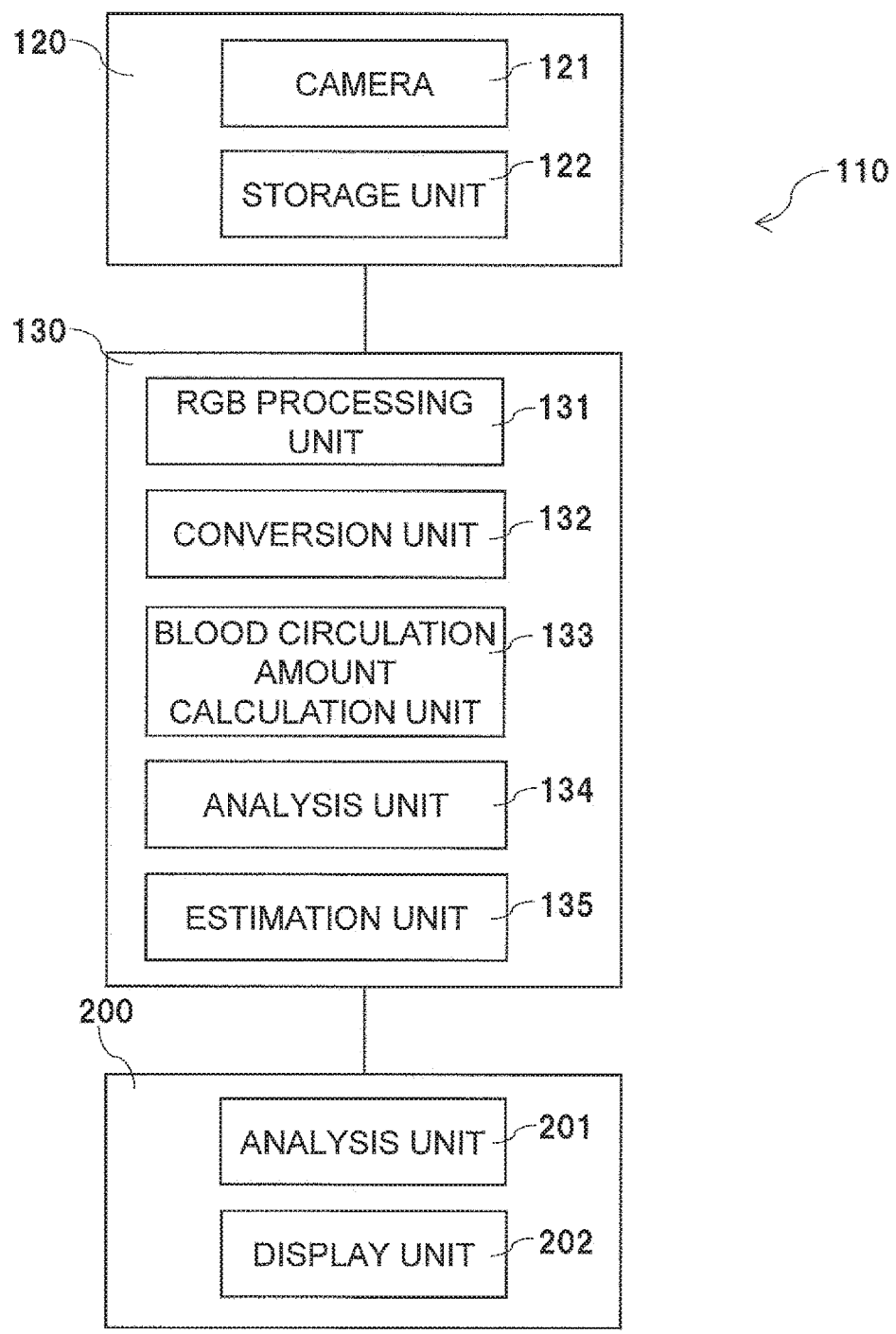
FIG. 21 is an exemplary diagram of a brain activity visualization device according to an embodiment of the present invention.
Figure 22:
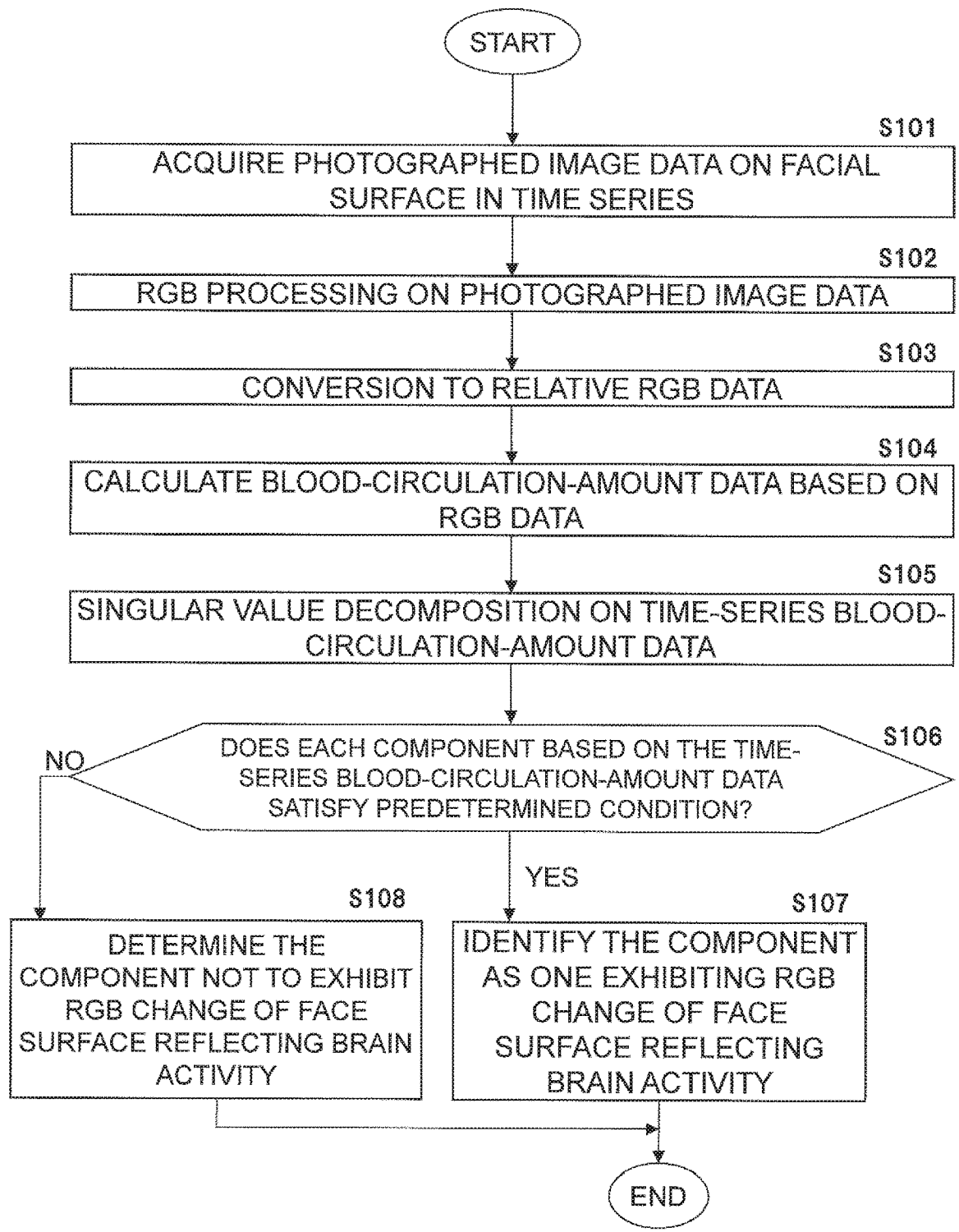
FIG. 22 is a flowchart showing an example of the flow of processing performed in identifying a component indicative of an RGB change on a facial surface reflecting a brain function in the brain activity visualization device.

(4-2) Brain Activity Estimation Means 130 for Estimating the Brain Activity Based on the Photographed Image Data on the Facial Surface FIG. 21 is an exemplary diagram of the brain activity visualization device 110 according to an embodiment of the present invention. FIG. 22 is a flowchart showing an example of the flow of processing performed when a component indicative of an RGB change on a facial surface reflecting a brain function is identified in the brain activity visualization device 110.

The brain activity estimation means 130 included in the brain activity visualization device 110 is a device for estimating the brain activity of an individual (test subject) from the photographed image data on the individual's facial surface. As shown in FIG. 21, the brain activity visualization device 110 includes image data acquisition means 120, the brain activity estimation means 130, and state visualization means 200.

The image data acquisition means 120 acquires the photographed image data on at least a part of the individual's facial surface in time series (step S101). The image data acquisition means 120 is not particularly limited as long as it has at least an imaging device. The image data acquisition means 120 can be, for example, a portable terminal incorporated therein an imaging device, such as a smartphone or a tablet (for example, iPad: registered trademark). Here, as shown in FIG. 21, the image data acquisition means 120 includes a camera 121 as an imaging device and a storage unit 122. The camera 121 is to acquire photographed image data on an individual's facial surface in time series. Here, the camera 121 photographs a moving image of the entire facial surface of an individual, and acquires photographed moving image data. The storage unit 122 stores therein the time-series photographed image data photographed by the imaging device. Here, the storage unit 122 stores therein the moving image data acquired by the camera 121.

Although here, the moving image of the entire facial surface is photographed by the camera 121, the moving image is not limited to this range. Alternatively, a moving image including an image of at least the forehead and/or the paranasal sinus peripheral region of the facial surface only needs to be photographed.

Here, while the time-series photographed image data on the facial surface is being acquired by the image data acquisition means 120, the brain function activation task is given to the individual for a certain period of time. That is, the photographed image data acquired by the image data acquisition means 120 inevitably includes data provided for a period of time during which the brain function activation task is given to the individual. Note that the brain function activation task given to the individual is not particularly limited as long as it is estimated to bring the brain into the activated state. For example, the brain function activation task may be configured to have its contents determined as appropriate in accordance with the purpose of use of the brain activity visualization device 110.

The brain activity estimation means 130 estimates the human brain activity based on the time-series photographed image data regarding the facial surface acquired by the image data acquisition means 120. Specifically, as shown in FIG. 21, the brain activity estimation means 130 includes an RGB processing unit 131, a conversion unit 132, a blood circulation amount calculating unit 133, an analysis unit 134, and an estimation unit 135. FIG. 21 shows an embodiment in which the brain activity estimation means 130 is configured as one device that includes the RGB processing unit 131, the conversion unit 132, the blood circulation amount calculating unit 133, the analysis unit 134, and the estimation unit 135. However, the present invention is not limited thereto. Alternatively, a part(s) or each of the RGB processing unit 131, the conversion unit 132, the blood circulation amount calculating unit 133, the analysis unit 134, and the estimation unit 135 may be configured as an independent device. Here, the image data acquisition means 120, the RGB processing unit 131, the conversion unit 132, and the blood circulation amount calculating unit 133 constitute the facial blood circulation amount acquisition means.

The RGB processing unit 131 conducts the RGB processing for decomposing the photographed image data acquired by the image data acquisition means 120, into three color components composed of an R component, a G component, and a B component (step S102). Here, although the RGB processing may be conducted on the photographed image data on the entire facial surface, in order to reduce the amount of computation processing and noise, data on the forehead and/or the paranasal sinus peripheral region is extracted from the photographed image data, and then the RGB processing is conducted only on the extracted data.

The conversion unit 132 converts the RGB data, acquired from the photographed image data by the RGB processing, into relative RGB data (step S103). Specifically, the conversion unit 132 sets an average value of the RGB data obtained from the photographed image data acquired every predetermined time (for example, 30 seconds) as a reference value, and then converts the RGB data to the relative RGB data.

The blood circulation amount calculating unit 133 calculates the time-series facial blood-circulation-amount data based on the RGB data acquired from the photographed image data by the RGB processing (step S104).

The analysis unit 134 decomposes the time-series relative-conversion blood-circulation-amount data into a plurality of components by the singular value decomposition, principal component analysis, or independent component analysis (step S105). Here, the analysis unit 134 conducts the singular value decomposition on the relative-conversion blood-circulation-amount data using the SVD of MATLAB (registered trademark) as the analysis tool. Specifically, in the singular value decomposition, the target is defined as the time-series relative-conversion blood-circulation-amount data, the factor is defined as time data acquired every predetermined time period (for example, 30 seconds), and the measure is defined as the relative-conversion blood-circulation-amount data for each pixel that is computed from the relative RGB data acquired every predetermined time period. By the singular value decomposition, the time-series relative-conversion blood-circulation-amount data is decomposed into a plurality of components, and then a time distribution, a space distribution, and a singular value indicative of the size of each component are calculated.

The analysis unit 134 determines whether or not each component satisfies a predetermined condition in order to identify the component indicative of the RGB change on the facial surface reflecting the brain activity, from among the plurality of components obtained by the singular value decomposition (step S106). Here, the predetermined condition includes, for example, a condition in which the amplitude of the component waveform of the component obtained by the singular value decomposition has a correlation with changes of the brain in the non-activation time and the activation time (hereinafter referred to as the first condition), a condition in which the component obtained by the singular value decomposition has a change in the blood circulation amount at a predetermined part on the human's facial surface (hereinafter referred to as the second condition), and the like. The predetermined condition based on which the determination is made by the analysis unit 134 may include one or a plurality of preset conditions, and here, it is assumed that the first condition is set as the predetermined condition.

The analysis unit 134 extracts components satisfying the predetermined condition as a determination component from the plurality of components. Subsequently, the analysis unit 134 identifies a component(s) satisfying all the conditions included in the predetermined condition among the extracted determination components, as a component(s) indicative of the RGB change on the facial surface reflecting the brain activity (step S107). Meanwhile, the analysis unit 134 determines that a component(s) determined not to satisfy at least one of the conditions included in the predetermined condition among the extracted determination components, is not a component(s) indicating the RGB change on the facial surface reflecting the brain activity (step S108).

Here, as mentioned above, only one condition (the first condition) is set as the predetermined condition. While the time-series photographed image data on the facial surface is being acquired, there is a certain period of time during which the brain function activation task is given to the individual. The analysis unit 134 defines a time period during which the brain function activation task is not given to the individual as the brain non-activation time, and also defines a time period during which the brain function activation task is given to the individual as the brain activation time. Then, the analysis unit 134 compares and analyzes the component waveform of each component with each of the brain non-activation time and the brain activation time. The analysis unit 134 evaluates whether or not there is a correlation between the component waveform of each component and each of the brain non-activation time and the brain activation time, using the comparison analysis result based on the component waveform data. Then, the analysis unit 134 extracts the component(s) evaluated to have a correlation, from the plurality of components as a determination component that satisfies a predetermined condition, and identifies this component as a component exhibiting the RGB change on the facial surface that reflects the brain activity. Meanwhile, the analysis unit 134 determines that the component evaluated to have no correlation among the plurality of components is not a component that exhibits the RGB change on the facial surface reflecting the human brain activity while not satisfying the predetermined condition.

Here, the brain function activation task is given to the individual for a certain period of time in acquiring the time-series photographed image data on the facial surface, and based on this result, the analysis unit 134 extracts the determination component. However, the contents of the first condition, i.e., the extraction means of the determination component in the analysis unit 134 is not limited thereto. For example, when a component that exhibits the component waveform having a correlation with the brain non-activation time and the brain activation time is specified from among the plurality of components by conducting experiments or the like in advance, the analysis unit 134 extracts the specified component from the plurality of components as the determination component. In addition, when a human's movement known to be related to the activation/non-activation of the brain, such as eye movement or blink, is detected on the brain activity visualization device 110, the analysis unit 134 may compare, analyze, and evaluate the detection result and the component waveform of each component, thereby extracting the determination component from the plurality of components. Note that the criterion for the analysis unit 134 to determine whether the first condition is satisfied or not is determined as appropriate by simulation, experiments, desk calculation, or the like in accordance with the purpose of use of the brain activity visualization device 110 or the like.

When the second condition is set as the predetermined condition, the analysis unit 134 extracts the determination component based on the presence or absence of the change in the facial blood circulation amount at a predetermined part on the human's facial surface. Specifically, the analysis unit 134 determines whether or not a change in the blood circulation amount occurs in the paranasal sinus peripheral region and/or the forehead based on the blood circulation amount distribution diagrams corresponding to the plurality of components obtained by the singular value decomposition. Then, if the change in the blood circulation amount occurs for one component, the analysis unit 134 determines that this component satisfies the second condition. On the other hand, when the change in the blood circulation amount does not occur in the paranasal sinus peripheral region and/or the forehead for one component, the analysis unit 134 determines that this component does not satisfy the second condition. Note that the criterion for the analysis unit 134 to determine whether the second condition is satisfied or not is determined as appropriate by simulation, experiments, desk calculation, or the like in accordance with the purpose of use or the like of the brain activity visualization device 110.

Further, when the time-series blood-circulation-amount data based on the RGB data before conversion to the relative RGB data is calculated by the blood circulation amount calculating unit 133, the analysis unit 134 may also determine whether or not the above-mentioned first condition and/or second condition are/is satisfied by the plurality of components obtained by decomposing the blood-circulation-amount data through the singular value decomposition. Then, the analysis unit 134 may extract the determination component from the plurality of components.

The estimation unit 135 estimates the human brain activity based on the component identified by the analysis unit 134 as the component indicative of the RGB change on the facial surface reflecting the human brain activity. Specifically, the estimation unit 135 estimates the amount of brain activity at the time of acquiring the photographed image data on the facial surface based on the component waveform data regarding the component identified by the analysis unit 134.

(4-2-1) Modified Example 2A

As mentioned above, for example, a portable terminal or the like incorporating therein an imaging device, such as a smartphone or a tablet (for example, iPad: registered trademark) can be used as the camera 12. That is, a device for the above-mentioned photographed image data can adopt any device capable of capturing images in the visible light range.

The blood circulation amount calculating unit 133 may calculate the facial blood-circulation-amount data mainly using the R component among the respective pixels included in the RGB data. As long as the blood-circulation-amount data can be calculated based on the RGB data, the blood-circulation-amount data is not necessarily limited to the erythema index.

(4-2-2) Modified Example 2B

The blood circulation amount calculating unit 133 calculates the relative-conversion blood-circulation-amount data based on the relative RGB data obtained by conversion with the conversion unit 132. However, instead of or in addition to this, the blood-circulation-amount data may be calculated based on the RGB data before being converted to the relative RGB data. Here, the components correlated with the brain activity are more likely to appear (with a high verification capability) in the blood-circulation-amount data calculated based on the RGB data before being converted to the relative RGB data. Because of this, for example, the blood-circulation-amount data calculated based on the RGB data before being converted to the relative RGB data may be analyzed prior to the relative-conversion blood-circulation-amount data calculated based on the relative RGB data. Further, for example, first, the blood-circulation-amount data is analyzed to extract a component having a significant correlation with the brain activity. Regarding the relative-conversion blood-circulation-amount data, only a component thereof corresponding to the extracted component of the blood-circulation-amount data is analyzed, so that the computation processing amount can be decreased in total.

(4-2-3) Modified Example 2C

Although it is assumed that the camera 121 is a normal camera of the visible light range, an infrared camera can be used. In this case, an object is irradiated with infrared light, and its reflected wave is photographed by the infrared camera. Thus, the photographed image data including changes of the subject's facial surface or the like can be acquired. The inventors have confirmed that there is a correlation between the blood-circulation-amount data calculated from the photographed image data acquired by reflection of infrared rays and the blood-circulation-amount data calculated mainly using the R component among the respective pixels contained in the RGB data, acquired by photographing with light in the visible light range. Therefore, even the use of such photographed image data acquired from the reflection of the infrared rays enables the estimation of the human brain activity.

(4-2-4) Modified Example 2D

In the description above, the brain activity visualization device 110 includes the image data acquisition means 120 and the brain activity estimation means 130. However, a brain activity visualization device according to the present embodiment is not limited to such a configuration. That is, the brain activity visualization device according to the present embodiment may have any other configuration as long as it includes the blood circulation amount calculating unit 133, the analysis unit 134, and the estimation unit 135. Specifically, the brain activity visualization device according to the present embodiment can have not only a configuration in which the brain activity visualization device itself photographs or captures image data, but also a configuration in which the brain activity visualization device receives photographed image data from an external device and then analyzes the received data.

(4-3) State Visualization Means 200

The state visualization means 200 visualizes the physiological state of the subject by displaying based on the brain activity of the subject estimated by the brain activity estimation means 30 and/or the brain activity estimation means 130. For example, the state visualization means 200 may include an analysis means 201 that analyzes the physiological state of the subject through the analysis of changes in the amount of brain activity of the subject. Specifically, the analysis means 201 determines the physiological state of the subject by analyzing a change in the amount of brain activity with respect to a stimulus given to the subject (visual stimulus, auditory stimulus, tactile stimulus, odor stimulus, taste stimulus, and the like). The type and level of the physiological state may be determined based on an increased amount of the brain activity and/or duration of the brain activity amount. Then, based on the determined physiological state, the analysis means 201 may be set as appropriate in accordance with applications of the brain activity visualization devices 10 and 110. The physiological state of the subject analyzed by the analysis means 201 is output from a display means 202 of the state visualization means 200 to an administrator, so that the administrator can know the physiological state of the subject. The display means 202 can be any display device, such as a display device for displaying an image or a message, which can visualize information on the physiological state of an analyzed subject to the administrator.

In addition, when various data are acquired in time series by the facial skin temperature acquisition means 20 and/or the image data acquisition means 120 after the components reflecting the brain activity are identified in the analysis units 32 and 134, the brain activity visualization device 10 and 110 decompose various acquired data into a plurality of components by the singular value decomposition, and then analyze the identified components only, thereby making it possible to know the physiological state of the subject in real time.

Furthermore, there has been a conventional technique for acquiring heart rate information, biological information, and the like of the test subject from the facial skin temperature of the test subject and a photographed image thereof. Owing to this, various data acquired from the facial skin temperature acquisition means 20 and/or the image data acquisition means 120 are decomposed into components by the singular value decomposition or the like. Then, the above conventional technique is applied to the component obtained by the singular value decomposition, thereby making it possible to accurately acquire the heart rate information and biological information. Therefore, the analysis unit 32 and/or analysis unit 134 may have the function of acquiring the heart rate information and biological information by analyzing the plurality of components decomposed by the singular value decomposition, whereas the estimation units 33 and 135 of the present embodiment may have the function of estimating the activity of the sympathetic nerve/parasympathetic nerve based on the acquired heart rate information or biological information.

(5) Features (5-1)

In the present embodiment, the human brain activity can be estimated based on the time-series facial skin temperature data and/or facial blood-circulation-amount data acquired by the facial skin temperature acquisition means 20 and/or the image data acquisition means 120, respectively. Thus, the human brain activity can be estimated even when a sensor, such as a brain wave electrode, requiring any processing before attachment is not attached. Therefore, the human brain activity can be easily estimated, and thereby the physiological state of the subject can be visualized based on the estimated brain activity.

(5-2)

Here, when the time-series facial skin temperature data and/or image data are acquired, the human brain is activated or not activated by actually giving the brain function activation task to the human or not. In such a case, a component having a correlation between its component waveform and each of the brain activation time and the brain non-activation time is said to be highly likely to exhibit changes in the skin temperature and/or blood circulation amount reflecting the brain activity.

In the present embodiment, the brain function activation task is given to the individual for a certain period of time while the time-series facial skin temperature data and/or image data is acquired by the facial skin temperature acquisition means 20 and/or image data acquisition means 120, respectively. That is, in the present embodiment, the human brain is activated or not activated by actually giving the brain function activation task to the individual or not. Then, various data acquired in time series in this way is decomposed into a plurality of components by the singular value decomposition. Then, the correlation between the component waveform of each component and each of the brain activation time and brain non-activation time is evaluated, and consequently, the component evaluated to have the correlation is extracted from the plurality of components as the determination component. Thus, for example, the possibility that the component less related to the human brain activity is extracted from the plurality of components as the extraction component can be reduced, as compared with when a predetermined component specified by experiments or the like in advance is extracted from the plurality of components as the extraction component.

(5-3)

Here, the brain has a mechanism called selective brain cooling system, which cools the brain independently of the body temperature. The selective brain cooling mechanism is known to discharge heat generated by the brain activity through the forehead and the paranasal sinus peripheral region. As such, the changes in the facial skin temperature and in the facial blood circulation amount correlated with the facial skin temperature appear in the forehead and/or paranasal sinus peripheral region.

In the present embodiment, various data acquired from the forehead and/or the paranasal sinus peripheral region are analyzed to extract the determination component. Thus, the component related to the human brain activity can be extracted with high accuracy.

(6) Application Examples of Brain Activity Visualization Device (Determination Result Output Device. Determination Result Provision Device, System)

Next, a description will be given on the determination result output device and system to which the brain activity visualization device according to the present invention is applied.

(6-1) First Embodiment (6-1-1) Configuration of Determination Result Output Device 800

Figure 23:
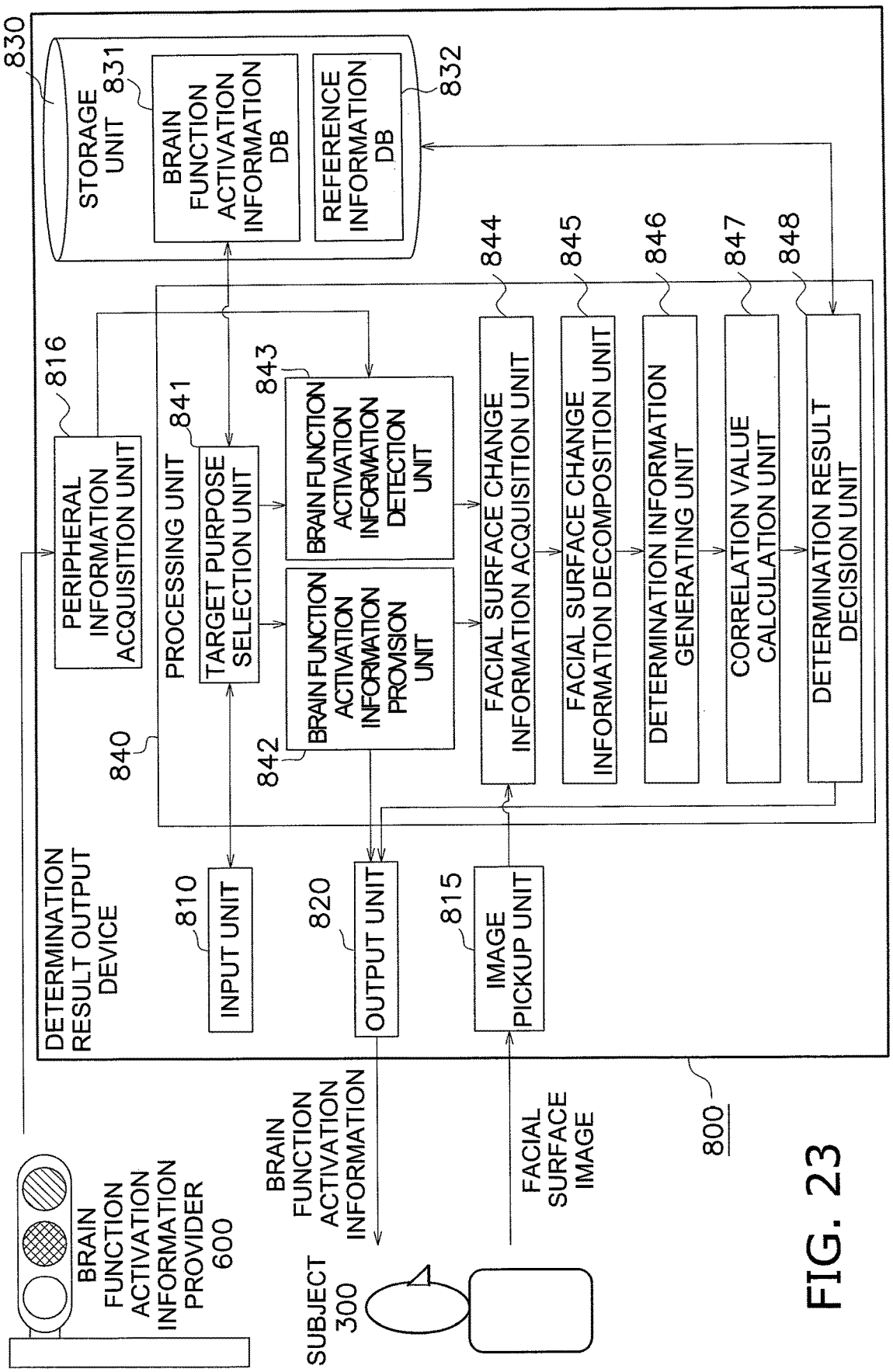
FIG. 23 is a schematic diagram showing a configuration of a determination result output device 800 according to a first embodiment.

FIG. 23 is a schematic diagram showing a configuration of a determination result output device 800 according to a first embodiment.

The determination result output device 800 includes an input unit 810, an image pickup unit 815, a peripheral information acquisition unit 816, an output unit 820, a storage unit 830, and a processing unit 840. A brain-function activation information provision unit 600 exists in the peripheral area of the determination result output device 800. As used herein, the term "brain-function activation information provision unit 600" refers to a member that provides "brain-function activation information" for stimulating the human brain function. The brain-function activation information provision unit 600 is, for example, a traffic light. The brain-function activation information will be described later.

The input unit 810 inputs various types of information into the determination result output device 800. For example, the input unit 810 may include a keyboard, a mouse, and/or a touch screen. Various commands are input to the determination result output device 800 via the input unit 810, and processing corresponding to the input command is executed in the processing unit 840.

The image pickup unit 815 captures a "facial surface image" including an image of the facial surface of a subject 300. For example, the image pickup unit 815 includes solid-state imaging devices, such as a Charge Coupled Device (CCD) and a Complementary Metal-Oxide-Semiconductor (CMOS), for acquiring RGB images, an infrared camera for acquiring thermograms, and the like. An infrared camera is used as the image pickup unit 815, thereby enabling the determination of the subject's state without being influenced by the ambient brightness. In particular, accidents or the like due to fatigue tend to occur at night. Also, in such a case, by mounting an infrared camera in the determination result output device 800 according to the first embodiment, the state of the subject can be monitored at night. Desirably, the infrared camera or the like is one capable of detecting the temperatures of 29.0° C. to 37.0° C. with high sensitivity in a normal room temperature condition. The image pickup unit 815 is capable of continuously capturing images at predetermined intervals. In the case of capturing a facial surface image, capturing an image from the front and capturing an image with constant illumination are desirable. When the front image cannot be obtained due to variations in the subject's posture, the three-dimensional shape of the face is estimated for the posture variation image by using a perturbation space method, and referring to the estimated shape, the front image is rendered, thereby producing a facial surface image. As for the illumination variation image, a facial surface image under the constant illumination condition is produced using an illumination basis model of a face configured based on a diffuse reflection model. Then, the facial surface image continuously captured by the image pickup unit 815 is sent to the processing unit 840.

The peripheral information acquisition unit 816 detects brain-function activation information provided from the brain-function activation information provision unit 600 that exists in the peripheral area of the determination result output device 800. For example, when the "display of a red signal" is adopted as the brain-function activation information, the peripheral information acquisition unit 816 acquires a "peripheral image" of the determination result output device 800. The information acquired by the peripheral information acquisition unit 816 is sent to a brain-function activation information detection unit 843 of the processing unit 840.

The output unit 820 outputs various types of information from the determination result output device 800. For example, the output unit 820 includes a display, a speaker, and the like. Here, the brain-function activation information to be described later is provided to the subject 300 via the output unit 820. The determination result is output via the output unit 820.

The storage unit 830 stores information input to the determination result output device 800, information calculated by the determination result output device 800, and the like. For example, the storage unit 830 includes a memory, a hard disk device, and the like. The storage unit 830 stores a program for achieving each function of the processing unit 840 as described later. Here, the storage unit 830 includes a brain-function activation information database 831 and a reference information database 832.

Figure 24:
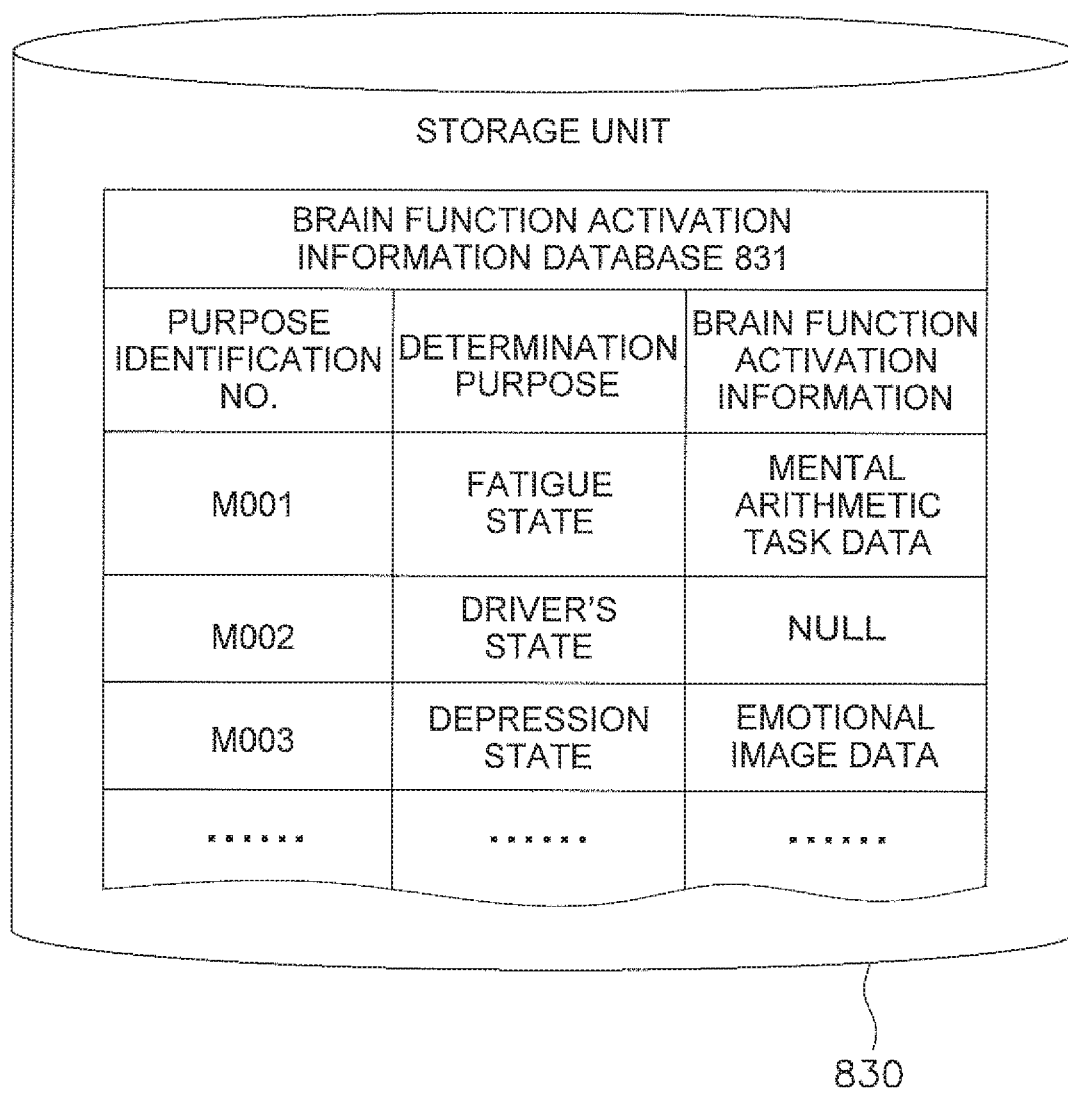
FIG. 24 is a schematic diagram showing a configuration of a brain-function activation information database 831 according to the first embodiment.

As shown in FIG. 24, the brain-function activation information database 831 stores therein the "brain-function activation information" for stimulating the human brain function for each determination purpose. Here, as the purpose of determination, for example, "fatigue state determination", "depression state determination", "driver's state determination", or the like can be selected. In the fatigue state determination, a mental arithmetic task or the like can be adopted as the brain-function activation information. In the depression state determination, emotional images classified into a negative image or a positive image can be adopted as the brain-function activation information. In the driver's state determination of the subject who operates a device, information obtained from arbitrary events and times regarding the operations of automobiles, railway vehicles, airplanes, nuclear power generation equipment, and other automatic machines, such as various plants, can be used as the brain-function activation information. For example, when the subject 300 is a driver of a traffic equipment, such as an automobile, a railway vehicle, or an airplane, alarm or the like can be adopted as the brain-function activation information. When the subject 300 is a driver of an automobile, the "display of red signal" or the like can be used as the brain-function activation information. In this case, the brain-function activation information is provided from a traffic light which is the brain-function activation information provision unit 600. The term "driver's state" as used herein represents the mental state and the physical state of the subject who drives the device. For example, the mental state is represented by an index corresponding to mental fatigue, mental stress, a disorientation state, a concentration state, or the like. The physical condition is represented by an index corresponding to body fatigue, physical stress, or the like.

Figure 25:
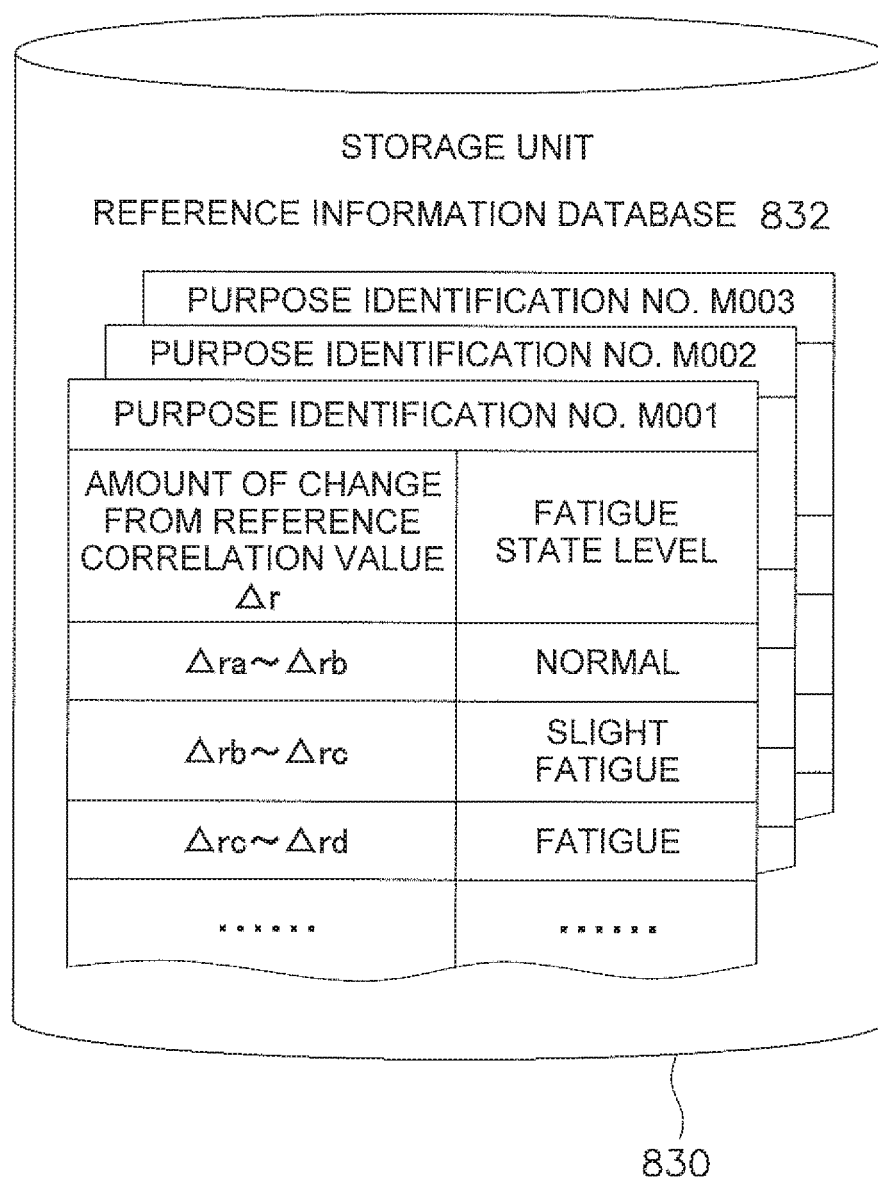
FIG. 25 is a schematic diagram showing a configuration of a reference information database 832 according to the first embodiment.

The reference information database 832 stores reference information for each of a plurality of determination purposes. Specifically, as shown in FIG. 25, for each of a plurality of determination purposes, the reference information database 832 previously stores, as "reference information" in relation to the "state level", an amount of change $\Delta r$ (=r1−r2) within a predetermined range, from a "reference correlation value r1" of the reference determination component to a correlation value r2 of the determination component, where r2 is the correlation value of the determination component extracted by a determination information generating unit 846, to be described later, with respect to the brain-function activation information, whereas r1 is the correlation value of the reference determination component with respect to the brain-function activation information. The "reference determination component" is set by data on the determination component extracted at a predetermined timing, data for the determination component previously extracted, data on the determination component provided from the outside. Here, FIG. 25 illustrates the concept of the reference information when the determination purpose is the "fatigue state determination". That is, the reference information database 832 stores the reference information therein corresponding to the range of the amount of change $\Delta r$, specifically, $\Delta r = \Delta ra$ to $\Delta rb$ as "normal"; $\Delta rb$ to $\Delta rc$ as "slight fatigue"; and $\Delta rc$ to $\Delta rd$ as "fatigue". Here, $\Delta ra$, $\Delta rb$, $\Delta rc$, and $\Delta rd$ are arranged in ascending order. Note that data on the reference determination component are also stored in the reference information database 832.

The processing unit 840 executes information processing in the determination result output device 800. Specifically, the processing unit 840 includes a CPU, a cash memory, and the like. The processing unit 840 executes programs stored in the storage unit 830 to function as a target purpose selection unit 841, a brain-function activation information provision unit 842, a brain-function activation information detection unit 843, a facial-surface change information acquisition unit 844, a facial-surface change information decomposition unit 845, a determination information generating unit 846, a correlation value calculation unit 847, and a determination result decision unit 848.

The target purpose selection unit 841 selects one of a plurality of determination purposes as a "target purpose". Specifically, the target purpose selection unit 841 reads out a target purpose stored in the brain-function activation information database 831, and outputs it to the output unit 820. Then, a selection command for the target purpose is input through the operation of the input unit 810 by the subject 300, and the target purpose is selected in accordance with the command.

The brain-function activation information provision unit 842 refers to a member that provides the brain-function activation information corresponding to the target purpose. More specifically, when the target purpose is selected by the target purpose selection unit 841, the brain-function activation information provision unit 842 reads the brain-function activation information from the brain-function activation information database 831, and sends the read brain-function activation information to the output unit 820.

The brain-function activation information detection unit 843 refers to a member that detects the brain-function activation information corresponding to the target purpose. Specifically, the brain-function activation information detection unit 843 detects the brain-function activation information from the information transmitted from the peripheral information acquisition unit 816. For example, when the "driver's state determination" is selected as the target purpose, the brain-function activation information detection unit 843 requests the peripheral information acquisition unit 816 to transmit a peripheral image. When acquiring the peripheral image transmitted from the peripheral information acquisition unit 816 in response to the transmission request, the brain-function activation information detection unit 843 detects whether or not a red signal is displayed in the peripheral image.

The facial-surface change information acquisition unit 844 acquires "facial surface data" and "facial-surface change information" indicative of time-series changes in the facial surface data from the facial surface image captured by the image pickup unit 815. Specifically, the facial-surface change information acquisition unit 844 acquires facial surface data via the image pickup unit 815 in synchronization with the timing at which the brain-function activation information provision unit 842 provides the brain-function activation information as well as the timing at which the brain-function activation information detection unit 843 detects the brain-function activation information, or the like. The facial-surface change information acquisition unit 844 acquires the facial-surface change information indicative of the time-series changes in the facial surface data regarding the subject 300, from the facial surface images continuously acquired. For example, facial surface data of 240×320 pixels are acquired from 60 points at predetermined intervals to produce the facial-surface change information composed of a collection of 4,608,000 pieces of data. The acquired facial-surface change information is sent to the facial-surface change information decomposition unit 845. When the image pickup unit 815 is an infrared camera, the facial-surface change information acquisition unit 844 acquires facial skin temperature data indicative of the facial skin temperature of the subject 300 as the facial surface data. When the image pickup unit 815 is a solid-state imaging device, such as a CCD and a CMOS, the facial-surface change information acquisition unit 844 acquires facial blood-circulation-amount data based on the RGB data regarding the facial surface of the subject 300 as the facial surface data. It should be noted that the facial-surface change information acquisition unit 844 may acquire the data only about the paranasal sinus peripheral region and/or the forehead of the subject 300 as the facial surface data.

The facial-surface change information decomposition unit 845 decomposes the facial-surface change information, which is the collection of a number of data, into a plurality of components 1, 2, 3, . . . by the singular value decomposition, the principal component analysis, or the independent component analysis. The information on the decomposed respective components is sent to the determination information generating unit 846. Here, when the facial-surface change information is subjected to the singular value decomposition or the like, the components 1, 2, 3, . . . are set in descending order of the singular value. In addition, the component with the higher singular value is more likely to be influenced by a factor that varies largely. Thus, the component 1 is often influenced by noise or the like of the external environment rather than by the provision of the brain-function activation information.

The determination information generating unit 846 generates determination information from the facial-surface change information. Specifically, the determination information generating unit 846 extracts a component related to the brain-function activation information from the plurality of components 1, 2, 3, . . . as a "determination component", and generates the determination information from the determination component.

The correlation value calculation unit 847 calculates a correlation value r between the brain-function activation information corresponding to the target purpose and the determination component.

The determination result decision unit 848 decides the determination result indicative of the subject's state based on the correlation value r between the brain-function activation information and the determination component. Specifically, the determination result decision unit 848 calculates a difference Δr between the reference correlation value r1 of the reference determination component extracted at a predetermined timing with respect to the brain-function activation information and the correlation value r2 of the determination component extracted thereafter with respect to the brain-function activation information. Then, the determination result decision unit 848 decides a state level corresponding to the difference Δr between the reference correlation value r1 and the present correlation value r2 based on the reference information stored in the reference information database 832. The decided state level is output to the display device or the like via the output unit 820.

(6-1-2) Operation of Determination Result Output Device

Figure 26:
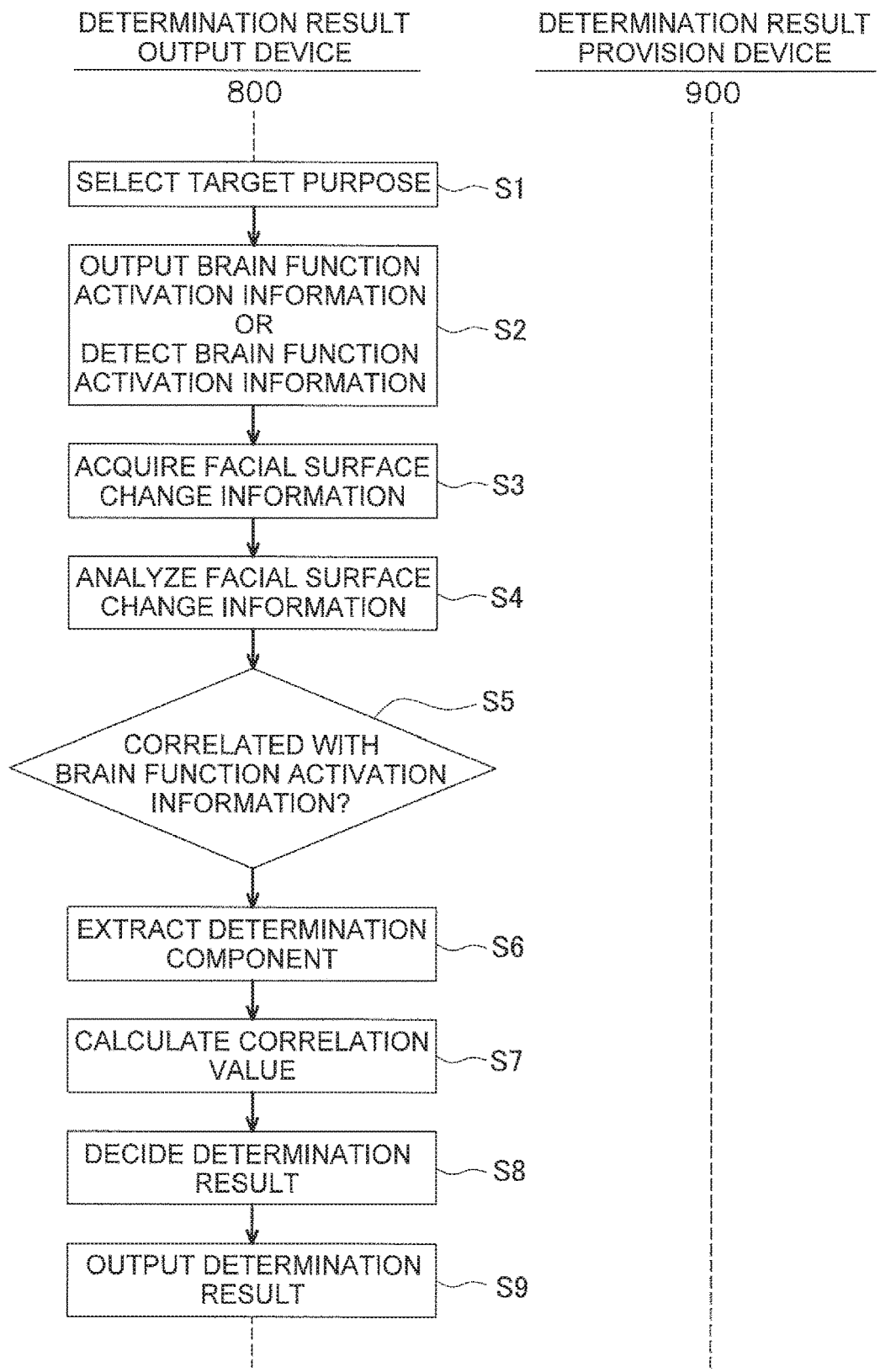
FIG. 26 is a sequence diagram for explaining the operation of a determination result output device 800 according to the first embodiment.

FIG. 26 is a sequence diagram for explaining the operation of the determination result output device 800 according to the first embodiment. In the first embodiment, unlike the second and third embodiments described later, the determination result output device 800 does not need to communicate with a determination result provision device 900. Note that the determination result output device 800 according to the first embodiment does not exclude a configuration in which the respective functions of the determination result output device 800 are constituted of other devices and communicate with each other via a network.

First, the target purpose is selected (S1). Specifically, the target purpose selection unit 841 reads out a plurality of target purposes stored in the brain-function activation information database 831 in response to an operation of the input unit 810 by the subject 300, and then outputs the read determination purposes to the output unit 820. Subsequently, among the plurality of determination purposes, one determination purpose is selected as the target purpose through the operation of the input unit 810 by the subject 300. For example, here, it is assumed that the "fatigue state determination", "depression state determination", and "driver's state determination" are displayed as the determination purposes, and then the "fatigue state determination" is selected via the input unit 810.

Here, when the brain-function activation information corresponding to the target purpose is stored in the brain-function activation information database 831, the brain-function activation information provision unit 842 reads out the brain-function activation information from the brain-function activation information database 831, and then sends the read information to the output unit 820 (S2). On the other hand, when the brain-function activation information corresponding to the target purpose is not stored in the brain-function activation information database 831, the brain-function activation information detection unit 843 detects the brain-function activation information via the peripheral information acquisition unit 816. For example, when the "fatigue state determination" is selected, a mental arithmetic task is extracted from the brain-function activation information database 831 and then provided to the subject 300 via the output unit 820 (S2). On the other hand, when the "driver's state determination" is selected as the target purpose, since the corresponding brain-function activation information is not stored in the brain-function activation information database 831, the brain-function activation information is acquired from the external environment via the peripheral information acquisition unit 816.

Then, at a predetermined timing, a facial surface image of the subject 300 existing in front of the output unit 820 is captured by the image pickup unit 815 at predetermined intervals (S3). The captured facial surface image is sent to the facial-surface change information acquisition unit 844.

Subsequently, the facial-surface change information acquisition unit 844 acquires, from the captured facial surface image, facial-surface change information indicative of the time-series changes in the facial surface data regarding the subject 300. Then, the facial-surface change information decomposition unit 845 decomposes the facial-surface change information into a plurality of components 1, 2, 3, . . . by the singular value decomposition, the principal component analysis, or the independent component analysis (S4).

Then, the determination information generating unit 846 extracts, as the determination component, a component related to the brain-function activation information from the plurality of components 1, 2, 3, . . . decomposed by the facial-surface change information decomposition unit 845 (S5, S6). If the determination component is not extracted, the determination processing is stopped.

Subsequently, the correlation value calculation unit 847 calculates a correlation value r2 between the brain-function activation information and the determination component (S7).

Then, the determination result decision unit 848 calculates a difference between the predetermined reference correlation value r1 and the above-mentioned correlation value r2 as the amount of change $\Delta r$ (S8). Subsequently, the determination result decision unit 848 decides the state level corresponding to a value of the amount of change $\Delta r$. For example, in a case where the "fatigue state determination" is selected as the target purpose, based on the reference information database 832 shown in FIG. 25, the subject is determined to be normal if the amount of change $\Delta r$ is within the above range of $\Delta ra$ to $\Delta rb$. On the other hand, the subject is determined to be in a fatigue state if the amount of change $\Delta r$ exceeds $\Delta rb$. Finally, these determination results are output on the display device or the like via the output unit 820 (S9).

(6-1-3) Features of Determination Result Output Device 800

(6-1-3-1)

As described above, the determination result output device 800 according to the first embodiment includes the target purpose selection unit 841, the brain-function activation information provision unit 842 or the brain-function activation information detection unit 843, the facial-surface change information acquisition unit 844, the determination information generating unit 846, the correlation value calculation unit 847, the determination result decision unit 848, and the output unit (determination result output unit) 820. The target purpose selection unit 841 selects one of the plurality of determination purposes as the "target purpose". The brain-function activation information provision unit 842 provides the "brain-function activation information" corresponding to the target purpose. The brain-function activation information detection unit 843 detects the "brain-function activation information" corresponding to the target purpose. The facial-surface change information acquisition unit 844 acquires the "facial-surface change information" indicative of the time-series changes in the facial surface data regarding the subject 300. The determination information generating unit (determination component extraction unit) 846 extracts the "determination component" related to the brain-function activation information corresponding to the target purpose, from the facial-surface change information by the singular value decomposition, the principal component analysis, or the independent component analysis. The correlation value calculation unit 847 calculates the "correlation value" between the brain-function activation information corresponding to the target purpose and the determination component. The determination result decision unit 848 decides the "determination result" indicative of the subject's state based on the correlation value. The output unit 820 outputs the determination result.

Therefore, the determination result output device 800 according to the first embodiment extracts the determination component related to the brain-function activation information corresponding to the selected target purpose, from the facial-surface change information by the singular value decomposition, the principal component analysis, or the independent component analysis, thereby making it possible to estimate the presence or absence of the brain activity of the subject without using any electrode or the like that requires any preprocessing before attachment. Then, the determination result indicative of various states of the subject 300 according to the target purpose can be output based on the correlation value of the determination component corresponding to the brain function of the subject.

(6-1-3-2)

The determination result output device 800 according to the first embodiment further includes the reference information database 832. Specifically, for each of a plurality of determination purposes, the reference information database 832 stores, as the reference information in relation to the state level, the amount of change Δr from the reference correlation value r1 of the reference determination component of the facial-surface change information with respect to the brain-function activation information. The determination result decision unit 848 decides the state level of the subject 300 based on the correlation value r2 as well as the reference correlation value r1. With such a configuration, the determination result indicative of various states of the subject 300 for the target purpose can be output by using the reference correlation value r1 obtained at a predetermined timing.

(6-1-3-3)

In the determination result output device 800 according to the first embodiment, the facial-surface change information acquisition unit 844 acquires the data on the paranasal sinus peripheral region and/or the forehead of the subject 300 as the facial surface data, thereby making it possible to extract the determination component related to the brain activity with high accuracy. Here, the brain has a mechanism called "selective brain cooling system", which cools the brain independently of body temperature. The selective brain cooling system is known to discharge heat generated by the brain activity through the forehead and the paranasal sinus peripheral region. Thus, by analyzing data on these parts, the component related to the brain activity can be extracted with high accuracy. As a result, the determination result output device 800 according to the first embodiment can execute the determination of the state of the subject 300 with high accuracy.

(6-1-3-4)

In the determination result output device 800 according to the first embodiment, the facial-surface change information acquisition unit 844 acquires the facial skin temperature data indicative of the facial skin temperature of the subject 300 as the facial surface data. In other words, the determination result output device 800 can execute the state determination of the subject 300 using the infrared camera or the like.

(6-1-3-5)

In the determination result output device 800 according to the first embodiment, the facial-surface change information acquisition unit 844 acquires the facial blood-circulation-amount data based on the RGB data regarding the facial surface of the subject 300, as the facial surface data. That is, the determination result output device 800 can execute the state determination of the subject 300 using the solid-state imaging device (CCD, CMOS). Thus, various types of state determination can be executed with a simple configuration.

(6-1-3-6)

In the determination result output device 800 according to the first embodiment, the determination information generating unit 846 extracts the determination component based on a value of the significance level. The determination result output device 800 extracts the determination component related to the brain-function activation information based on the value of the significance level, thereby making it possible to enhance the reliability of the state determination.

(6-1-3-7)

In the above description, the facial-surface change information is subjected to the singular value decomposition and the like, thereby extracting the determination component related to the brain-function activation information corresponding to the target purpose, from the facial-surface change information. However, the determination result output device 800 according to the first embodiment is not limited to such a configuration. For example, in the determination result output device 800 according to the first embodiment, the subject's state may be determined using any determination information, other than the determination components, which is generated based on the facial-surface change information. In order to generate such determination information, any method other than the singular value decomposition or the like may be applied to the facial-surface change information.

(6-2) Second Embodiment (6-2-1) Configuration of Determination Result Output System 700A

Hereinafter, the same portions as those already described above are denoted by substantially the same reference characters, and a repetitive description thereof is omitted. To distinguish from other embodiments, the present embodiment may have a suffix A added to a different configuration.

Figure 27:
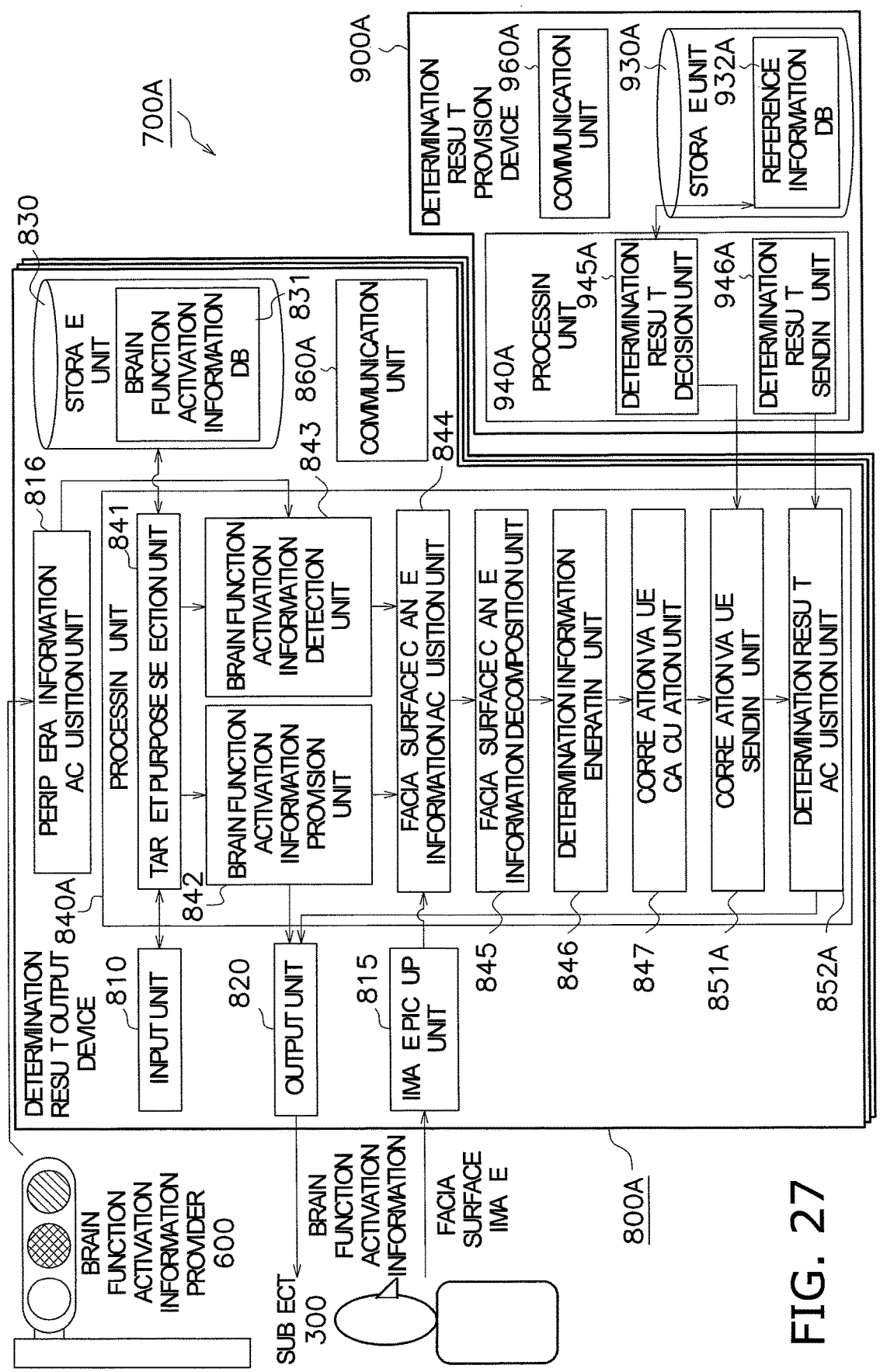
FIG. 27 is a schematic diagram showing a configuration of a determination result output system 700A according to a second embodiment.

FIG. 27 is a schematic diagram showing a configuration of a determination result output system 700A according to a second embodiment.

The determination result output system 700A according to the second embodiment includes a determination result output device 800A that outputs a determination result indicating the state of the subject 300, and a determination result provision device 900A that provides a determination result.

The determination result output device 800A includes a communication unit 860A, in addition to the input unit 810, the image pickup unit 815, the peripheral information acquisition unit 816, the output unit 820, the storage unit 830, and a processing unit 840A.

The processing unit 840A executes programs incorporated in the storage unit 830 to function as the target purpose selection unit 841, the brain-function activation information provision unit 842, the brain-function activation information detection unit 843, the facial-surface change information acquisition unit 844, the facial-surface change information decomposition unit 845, the determination information generating unit 846, the correlation value calculation unit 847, a correlation value sending unit 851A, and a determination result acquisition unit 852A.

The correlation value sending unit 851A is to relate a correlation value calculated in the correlation value calculation unit 847 to the target purpose and to send the correlation value related to the target purpose, to the determination result provision device 900A.

The determination result acquisition unit 852A acquires the determination result from the determination result provision device 900A in response to sending of the correlation value and the target purpose.

The communication unit 860A is a device capable of communicating with an external network in a wired or wireless manner. The determination result output device 800A can communicate with the determination result provision device 900A via the communication unit 860A.

The determination result provision device 900A acquires the correlation value of the determination component with respect to the brain-function activation information related to the target purpose, from the determination result output device 800A, and provides the determination result for the target purpose to the determination result output device 800A. The determination result provision device 900A includes a storage unit 930A, a processing unit 940A, and a communication unit 960A.

The storage unit 930A includes a reference information database 932A. The reference information database 932A has substantially the same configuration as the reference information database 832 of the first embodiment. That is, for each of a plurality of determination purposes, the reference information database 932A stores, as the reference information, the amount of change Δr from the reference correlation value r1 of the reference determination component of the facial-surface change information with respect to the brain-function activation information, in relation to the state level.

The processing unit 940A executes information processing in the determination result provision device 900A. Specifically, the processing unit 940A includes a CPU, a cash memory, and the like. The processing unit 940A executes a program incorporated in the storage unit 930A and thereby functions as a determination result decision unit 945A and determination result sending unit 946A.

When acquiring the correlation value r2 of the determination component with respect to the brain-function activation information related to the target purpose from the determination result output device 800A, the determination result decision unit 945A decides the determination result including the state level of the subject 300 based on the correlation value r2 and the reference information.

The determination result sending unit 946A sends the determination result to the determination result output device 800A.

The communication unit 960A is a device capable of communicating with an external network in a wired or wireless manner. The determination result provision device 900A can simultaneously communicate with a plurality of determination result output devices 800A via the communication unit 960A.

(6-2-2) Operation of Determination Result Output System 700A

Figure 28:
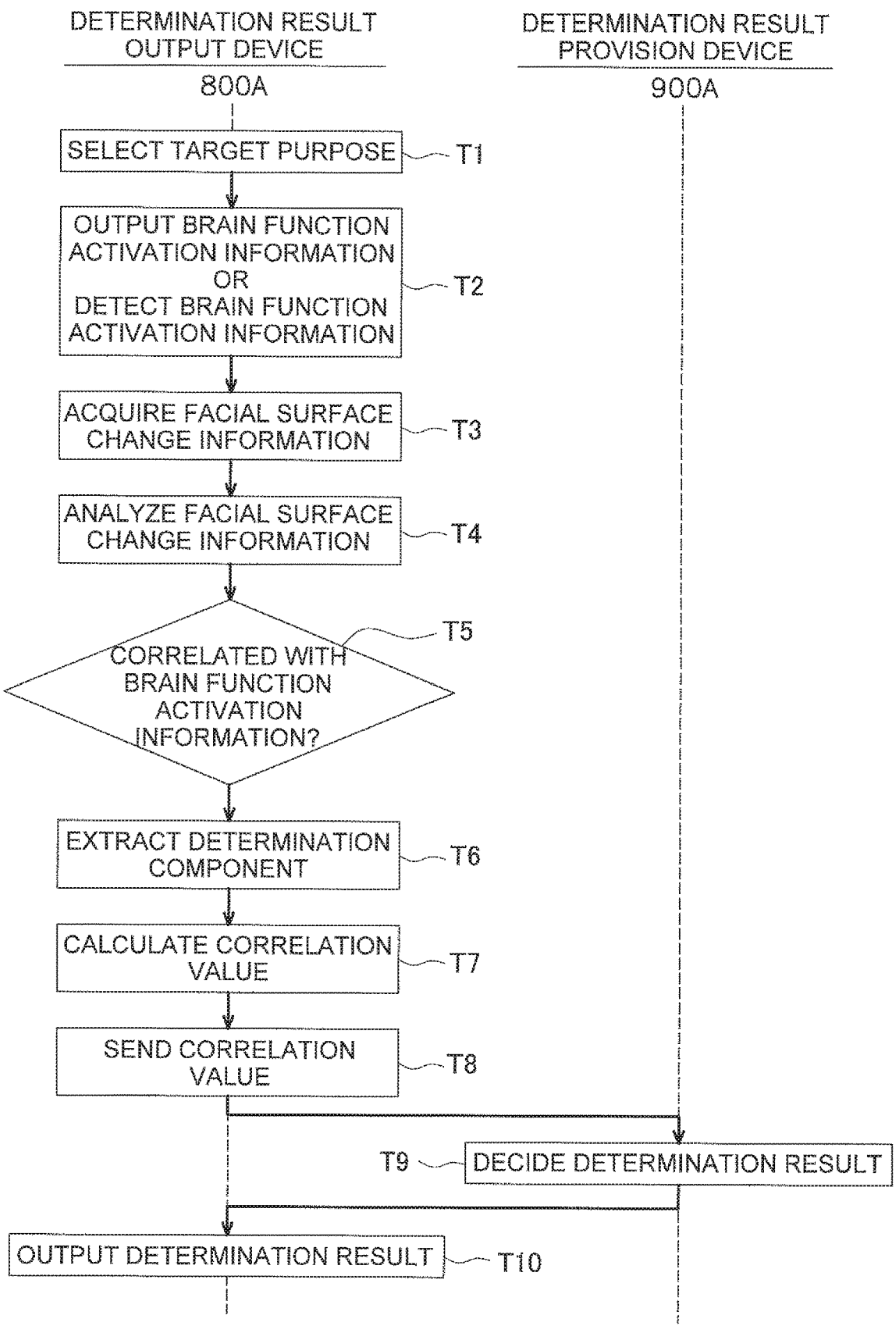
FIG. 28 is a sequence diagram for explaining the operation of the determination result output system 700A according to the second embodiment.

FIG. 28 is a sequence diagram for explaining the operation of the determination result output system 700A according to the second embodiment.

First, the determination result output device 800A selects one of the plurality of determination purposes as the "target purpose" (T1). Thus, the determination result output device 800A outputs the brain-function activation information or detects the brain-function activation information (T2).

Then, at a predetermined timing, the determination result output device 800A captures a facial surface image of the subject 300 (T3). Subsequently, the determination result output device 800A conducts the singular value decomposition or the like on the facial-surface change information (T4), and then extracts the determination component correlated with the brain-function activation information and calculates the correlation value r2 thereof (T5 to T7).

Thereafter, the determination result output device 800A sends the correlation value to the determination result provision device 900A in relation to the target purpose (T8).

Accordingly, the determination result provision device 900A acquires the correlation value related to the target purpose, from the determination result output device 800A. Then, the determination result provision device 900A decides the determination result based on the correlation value and the reference information in a reference information database 942 (T9). The decided determination result is sent to the determination result output device 800A.

Subsequently, the determination result output device 800A acquires the determination result from the determination result provision device 900. Ultimately, the determination result is output to the output unit 820 of the determination result output device 800A (T10).

(6-2-3) Features of Determination Result Output System 700A (6-2-3-1)

As described above, the determination result output system 700A according to the second embodiment includes the determination result output device 800A that outputs the determination result indicating the state of the subject 300, and the determination result provision device 900A providing the determination result. With this configuration, the determination result output system 700A according to the second embodiment can output the determination result indicative of various states of the subject 300 for the target purpose based on the determination component corresponding to the brain function of the subject 300.

(6-2-3-2)

The determination result output device 800A according to the second embodiment includes the target purpose selection unit 841, the brain-function activation information provision unit 842 or the brain-function activation information detection unit 843, the facial-surface change information acquisition unit 844, the determination information generating unit 846, the correlation value calculation unit 847, a correlation value sending unit 851A, a determination result acquisition unit 852A, and the output unit 820. The target purpose selection unit 841 selects one of the plurality of determination purposes as the target purpose. The brain-function activation information provision unit 842 provides the brain-function activation information corresponding to the target purpose. The brain-function activation information detection unit 843 detects the brain-function activation information corresponding to the target purpose. The facial-surface change information acquisition unit 844 acquires the facial-surface change information indicative of the time-series changes in the facial surface data on the subject 300. The determination information generating unit 846 extracts the determination component related to the brain-function activation information corresponding to the target purpose, from the facial-surface change information by the singular value decomposition, the principal component analysis, or the independent component analysis. The correlation value calculation unit 847 calculates the correlation value r2 between the brain-function activation information and the determination component. The correlation value sending unit 851A relates the correlation value r2 to the target purpose and sends the correlation value r2 to the determination result provision device 900A. The determination result acquisition unit 852A acquires the determination result from the determination result provision device 900A in response to sending of the correlation value r2 and the target purpose. The output unit 820 outputs the determination result.

Therefore, the determination result output device 800A according to the second embodiment extracts the determination component related to the brain-function activation information corresponding to the selected target purpose from the facial-surface change information, by the singular value decomposition, the principal component analysis, or the independent component analysis. This makes it possible to estimate the presence or absence of the brain activity of the subject 300 without using any electrode or the like that requires preprocessing before attachment. Furthermore, the determination result indicative of various states of the subject 300 for the target purpose can be output based on the component corresponding to the brain function of the subject 300. In addition, the determination result output device 800A causes the determination result provision device 900A to exert a part of the calculation function, which can reduce a calculation load on the determination result output device 800A itself. The determination result output device 800A according to the second embodiment stores only the brain-function activation information database 831 in the storage unit 830 and thereby can reduce a capacity used for an application. The determination result output device 800A can be realized by an any terminal which exerts its function by installing a program.

The determination result output device 800A may be configured by a dedicated chip. The determination result output device 800A may calculate a correlation value with heart rate information before and after the provision of the brain-function activation information. Depending on the determination purpose, the heart rate information may be used for determination of the state level.

A determination result output device 800B can select a fatigue state, a sleepy state, a concentrated state, a depressed state, and an inattentive driving state as target purposes. The brain-function activation information may include video, calculation, games, music, motion, acceleration, temperature change, and the like.

(6-2-3-3)

The determination result provision device 900A according to the present embodiment includes the reference information database 932A, a determination result decision unit 951A, and a determination result sending unit 952A. That is, for each of a plurality of determination purposes, the reference information database 932A stores, as the reference information in relation to the state level, the amount of change Δr from the reference correlation value r1 of the reference determination component of the facial-surface change information with respect to the brain-function activation information. When acquiring the correlation value r2 related to the target purpose from the determination result output device 800A, the determination result decision unit 951A decides the determination result including the state level of the subject 300 based on this correlation value r2 and the reference information. The determination result sending unit 952A sends the determination result to the determination result output device 800A.

Thus, the determination result provision device 900A according to the second embodiment can provide, to any determination result output device 800A, the determination result indicative of various states of the subject 300 corresponding to the target purpose by using the reference correlation value r1 previously set. The determination result provision device 900A can simultaneously provide the individual determination results to a plurality of determination result output devices 800A via the communication unit 960A.

(6-2-3-4)

Regarding other configurations, the second embodiment also has the same features as those described in the paragraph (6-1-3) of the first embodiment.

In the above description, the facial-surface change information is subjected to the singular value decomposition and the like, thereby extracting the determination component related to the brain-function activation information corresponding to the target purpose from the facial-surface change information. However, the determination result output system 700A according to the second embodiment is not limited to such a configuration. For example, in the determination result output device 700A according to the second embodiment, the subject's state may be determined using any determination information, other than the determination components, which is generated based on the facial-surface change information. In order to generate such determination information, any method other than the singular value decomposition or the like may be applied to the facial-surface change information.

(6-3) Third Embodiment (6-3-1) Configuration of Determination Result Output System 700B

Hereinafter, the same portions as those already described above are denoted by substantially the same reference characters, and a repetitive description thereof is omitted. To distinguish from other embodiments, the present embodiment may have a suffix B added to a different configuration.

Figure 29:
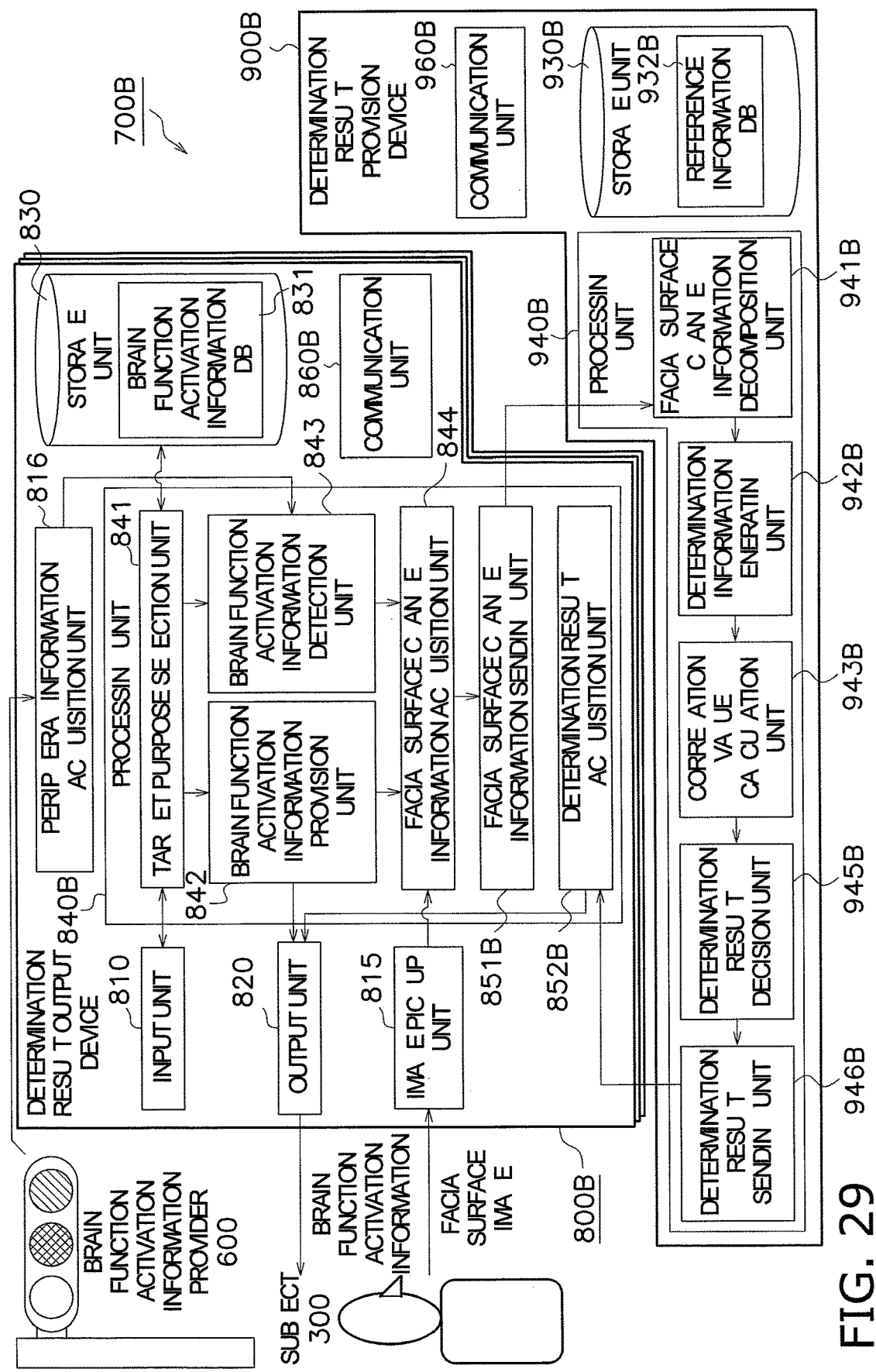
FIG. 29 is a schematic diagram showing a configuration of a determination result output system 700B according to a third embodiment.

FIG. 29 is a schematic diagram showing a configuration of a determination result output system 700B according to a third embodiment.

The determination result output system 700B according to the third embodiment includes a determination result output device 800B that outputs a determination result indicating the state of the subject 300, and a determination result provision device 900B that provides a determination result.

The determination result output device 800B includes a communication unit 860B, in addition to the input unit 810, the image pickup unit 815, the peripheral information acquisition unit 816, the output unit 820, the storage unit 830, and a processing unit 840B.

The processing unit 840B of the third embodiment executes programs incorporated in the storage unit 830 to function as the target purpose selection unit 841, the brain-function activation information provision unit 842 or the brain-function activation information detection unit 843, the facial-surface change information acquisition unit 844, a facial-surface change information sending unit 851B, and a determination result acquisition unit 852B.

The facial-surface change information sending unit 851B sends the facial-surface change information to the determination result provision device 900B in relation to the target purpose.

The determination result acquisition unit 852B acquires the determination result from the determination result provision device 900B in response to sending of the facial-surface change information and the target purpose.

The communication unit 860B is a device capable of communicating with an external network in a wired or wireless manner. The determination result output device 800B can communicate with the determination result provision device 900B via the communication unit 860.

The determination result provision device 900B acquires the facial-surface change information for the target purpose, from the determination result output device 800B and provides the determination result for the target purpose to the determination result output device 800B. The determination result provision device 900B includes a storage unit 930B, a processing unit 940B, and a communication unit 960B.

The storage unit 930B includes a reference information database 932B. The reference information database 932B has substantially the same configuration as the reference information database 832 of the first embodiment. That is, for each of a plurality of determination purposes, the reference information database 932B stores, as the reference information in relation to the state level, the amount of change Δr from the reference correlation value r1 of the reference determination component of the facial-surface change information with respect to the brain-function activation information.

The processing unit 940B executes information processing in the determination result provision device 900B.

Specifically, the processing unit 940B includes a CPU, a cash memory, and the like. The processing unit 940B executes a program incorporated in the storage unit 930B and thereby functions as a facial-surface change information decomposition unit 941B, a determination information generating unit 942B, a correlation value calculation unit 943B, a determination result decision unit 945B, and a determination result sending unit 946B.

The facial-surface change information decomposition unit 941B decomposes the facial-surface change information, which is the collection of a number of data, into a plurality of components 1, 2, 3, . . . by the singular value decomposition, the principal component analysis, or the independent component analysis. The information on the respective decomposed components is sent to the determination information generating unit 942B.

The determination information generating unit 942B extracts the determination component related to the brain-function activation information corresponding to the target purpose, from the facial-surface change information by the singular value decomposition, the principal component analysis, or the independent component analysis.

The correlation value calculation unit 943B calculates the correlation value between the brain-function activation information and the determination component.

The determination result decision unit 945B decides the determination result including the state level of the subject 300 based on the correlation value and the reference information.

The determination result sending unit 946B sends the determination result to the determination result output device 800B.

(6-3-2) Operation of Determination Result Output System 700B

Figure 30:
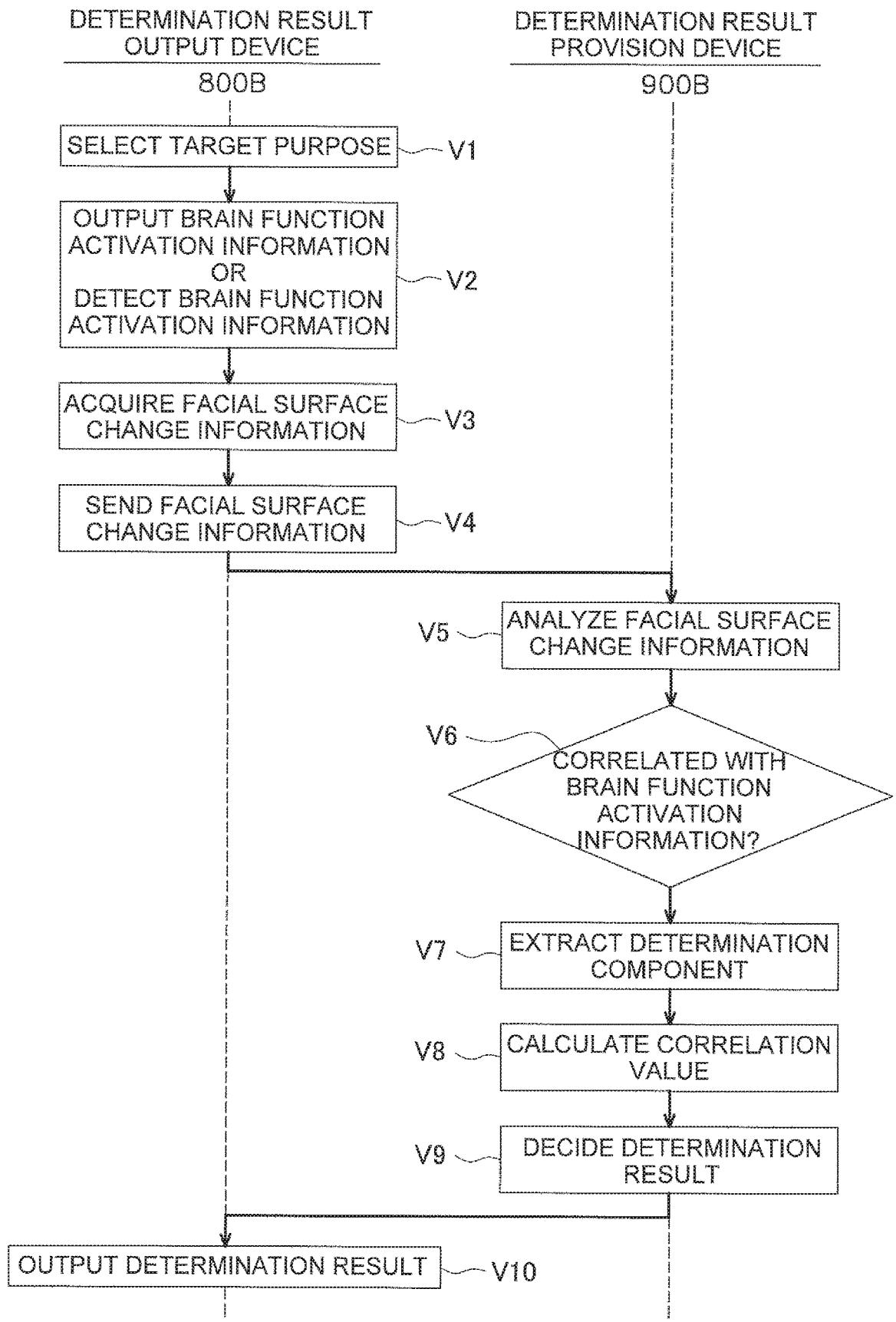
FIG. 30 is a sequence diagram for explaining the operation of the determination result output system 700B according to the third embodiment.

FIG. 30 is a sequence diagram for explaining the operation of the determination result output system 700B according to a third embodiment.

First, the determination result output device 800B selects one of the plurality of determination purposes as the "target purpose" (V1). Thus, the determination result output device 800V outputs the brain-function activation information or detects the brain-function activation information (V2).

Then, at a predetermined timing, the determination result output device 800B captures a facial surface image of the subject 300 (V3). Subsequently, the time-series data on the captured facial surface image is related to the target purpose and sent to the determination result provision device 900B (V4).

Then, the determination result provision device 900B acquires the facial-surface change information related to the target purpose. Subsequently, the determination result provision device 900B conducts the singular value decomposition or the like on the facial-surface change information (V5), and then extracts the determination component correlated with the brain-function activation information and calculates a correlation value therebetween (V6 to V8). Then, the determination result provision device 900A decides the determination result based on the reference information and the correlation value in the reference information database 942 (V9). The decided determination result is sent to the determination result output device 800B.

Subsequently, the determination result output device 800B acquires the determination result from the determination result provision device 900. Then, the determination result is output to the output unit 820 of the determination result output device 800B (V10).

(6-3-3) Features of Determination Result Output System 700B

(6-3-3-1)

As described above, the determination result output system 700B according to the third embodiment includes a determination result output device 800B that outputs the determination result indicating the state of the subject 300, and a determination result provision device 900B providing the determination result. With this configuration, the determination result output system 700B according to the third embodiment can output the determination result indicative of various states of the subject based on the determination component corresponding to the brain function of the subject 300.

(6-3-3-2)

The determination result output device 800B according to the third embodiment includes the target purpose selection unit 841, the brain-function activation information provision unit 842 or the brain-function activation information detection unit 843, the facial-surface change information acquisition unit 844, a facial-surface change information sending unit 851B, a determination result acquisition unit 852B, and the output unit 820. The target purpose selection unit 841 selects one of the plurality of determination purposes as the target purpose. The brain-function activation information provision unit 842 provides the brain-function activation information corresponding to the target purpose. The brain-function activation information detection unit 843 detects the brain-function activation information corresponding to the target purpose. The facial-surface change information acquisition unit 844 acquires the facial-surface change information indicative of the time-series changes in the facial surface data on the subject 300. The facial-surface change information sending unit 851B sends the facial-surface change information to the determination result provision device 900B in relation to the target purpose. The determination result acquisition unit 852B acquires the determination result from the determination result provision device 900B in response to sending of the facial-surface change information and the target purpose. The output unit 820 outputs the determination result.

With the above-mentioned configuration, the determination result output device 800B according to the third embodiment selects one of the plurality of determination purposes as the target purpose, thereby making it possible to output the determination result corresponding to the target purpose. In addition, the determination result output device 800B causes the determination result provision device 900B to execute a part of the calculation function, which can reduce a calculation load on the determination result output device 800B itself. The determination result output device 800B according to the third embodiment stores only the brain-function activation information database 831 in the storage unit 830 and thereby can reduce a capacity used for an application. Note that the determination result output device 800B can be realized by an any terminal which exerts its function by installing a program.

Note that the determination result output device 800B can select a fatigue state, a sleepy state, a concentrated state, a depressed state, and an inattentive driving state as the target purposes. The brain-function activation information may include video, calculation, games, music, motion, acceleration, temperature change, and the like.

(6-3-3-3)

The determination result provision device 900B according to the third embodiment includes a reference information database 932B, a determination information generating unit 942B, a correlation value calculation unit 943B, a determination result decision unit 945B, and a determination result sending unit 946B. For each of a plurality of determination purposes, the reference information database 932 stores, as the reference information in relation to the state level, the amount of change Δr from the reference correlation value r1 of the reference determination component of the facial-surface change information with respect to the brain-function activation information. When acquiring the facial-surface change information related to the target purpose from the determination result output device 800B, the determination information generating unit 942B extracts the determination component related to the brain-function activation information corresponding to the target purpose, from the facial-surface change information by the singular value decomposition, the principal component analysis, or the independent component analysis. The correlation value calculation unit 943B calculates the correlation value between the brain-function activation information and the determination component. The determination result decision unit 945B decides the determination result including the state level of the subject based on the correlation value and the reference information. The determination result sending unit 946B sends the determination result to the determination result output device 800B.

Thus, the determination result provision device 900B according to the third embodiment extracts the determination component related to the brain-function activation information corresponding to the selected target purpose from the facial-surface change information by the singular value decomposition, the principal component analysis, or the independent component analysis, thereby making it possible to estimate the presence or absence of the brain activity of the subject without using any electrode or the like that requires preprocessing before attachment. Then, the determination result indicative of various states of the subject 300 corresponding to the target purpose can be provided to any of the determination result output devices 800B based on the determination component corresponding to the brain function of the subject. The determination result provision device 900B can simultaneously provide the individual determination results to a plurality of determination result output devices 800B via the communication unit 960B.

Note that the determination result provision device 900B may calculate a correlation value with heart rate information before and after the provision of the brain-function activation information. According to the determination purpose, the heart rate information may be used for determination of the state level.

(6-3-3-4)

In addition, the third embodiment also has the same features as those described in the paragraph (6-1-3) of the first embodiment.

In the above description, the facial-surface change information is subjected to the singular value decomposition and the like, thereby extracting the determination component related to the brain-function activation information corresponding to the target purpose. However, the determination result output system 700B according to the third embodiment is not limited to such a configuration. For example, in the determination result output system 700B according to the third embodiment, the state of the subject may be determined using any determination information, other than the determination components, which is generated based on the facial-surface change information. In order to generate such determination information, any method other than the singular value decomposition or the like may be applied to the facial-surface change information.

FIGS. 4 and 5 are diagrams showing the relationships between the amplitudes of the component waveforms and brain waves. FIG. 4 is a diagram showing the amplitude of a component waveform of the component 2 exhibited by the test subject 1 and the amplitude of β waves among measured brain waves. FIG. 5 is a diagram showing the amplitude of a component waveform exhibited by the component 3 of the test subject 1 and the amplitude of β waves of the measured brain waves. The lower graph in each of FIGS. 4 and 5 is a diagram showing the amplitude of the β waves. The measured brain waves for each of the lower graphs in FIGS. 4 and 5 indicate a power of the beta band wave measured during an electroencephalogram (EEG) of a brain of the test subject.

INDUSTRIAL APPLICABILITY

According to the present invention, the human brain activity can be easily estimated. Therefore, the present invention can be effectively applied to brain activity visualization devices that visualize the physiological state of a subject based on the estimated brain activity.

What is claimed is:
1. A determination result output device, comprising:
a storage unit including a memory that includes a brain-function activation information database that stores a first brain-function activation information for stimulating a brain function of a subject;
a peripheral information acquisition unit that acquires a second brain-function activation information provided from a peripheral brain-function activation information provision unit that exists in the peripheral area;
a processor including
a target purpose selection unit that selects one of a plurality of determination purposes as a target purpose;
a brain-function activation information provision unit that provides the first brain-function activation information corresponding to the target purpose, the first brain-function activation information being stored in the brain-function activation information database;
a brain-function activation information detection unit that detects the second brain-function activation information corresponding to the target purpose, the second brain-function activation information being acquired via the peripheral information acquisition unit; and
a facial-surface change information acquisition unit that acquires facial-surface change information indicative of a time-series change in facial surface data of the subject when the first brain-function activation information is provided, or when the second brain-function activation information is detected; and
a determination result output notifier that outputs a determination result indicative of a state of the subject based on the first brain-function activation information provided when the facial-surface change information is acquired or the second brain-function activation information detected when the facial-surface change information is acquired and based on the facial-surface change information.

2. The determination result output device according to claim 1, wherein
the processor further includes
a determination information generating unit that generates determination information from the facial-surface change information; and
a correlation value calculation unit that calculates a correlation value between (1) the determination information and (2) the first brain-function activation information provided when the facial-surface change information is acquired or the second brain-function activation information detected when the facial-surface change information is acquired; and
the determination result output device further comprising a second processor that includes
a determination result decision unit that decides a determination result indicative of a state of the subject based on the correlation value.

3. The determination result output device according to claim 2, wherein
the determination information generating unit is configured to
extract a determination component related to the first brain-function activation information provided when the facial-surface change information is acquired or the second brain-function activation information detected when the facial-surface change information is acquired using singular value decomposition, principal component analysis, or independent component analysis on the facial-surface change information, and
generate the determination information from the determination component.

4. The determination result output device according to claim 3, further comprising:
a reference information storage memory that stores, as reference information in relation to a state level, an amount of change from a reference correlation value of a reference determination component of the facial-surface change information with respect to the first brain-function activation information provided when the facial-surface change information is acquired or the second brain-function activation information detected when the facial-surface change information is acquired for each of the plurality of determination purposes,
the determination result decision unit determining the state level of the subject based on the correlation value and the reference correlation value.

5. A determination result output system, comprising:
a determination result output device and
a determination result provision device,
the determination result output device comprising:
a storage unit including a memory that includes a brain-function activation information database that stores a first brain-function activation information for stimulating a brain function of a subject;
a peripheral information acquisition unit that acquires a second brain-function activation information provided from a peripheral brain-function activation information provision unit that exists in the peripheral area;
a first processer including
a brain-function activation information provision unit that provides the first brain-function activation information corresponding to a target purpose;
a brain-function activation information detection unit that detects the second brain-function activation information corresponding to the target purpose; and
a facial-surface change information acquisition unit that acquires facial-surface change information indicative of a time-series change in facial surface data of the subject when the first brain-function activation information is provided, or when the second brain-function activation information is detected;
a determination result acquisition unit that acquires a determination result indicative of a state of the subject being output based on the first brain-function activation information provided when the facial-surface change information is acquired or the second brain-function activation information detected when the facial-surface change information is acquired and based on the facial-surface change information;
the determination result provision device comprising
a second processor including
a determination information generating unit that generates determination information from the facial-surface change information;
a correlation value calculation unit that calculates a correlation value between (1) the determination information and (2) the first brain-function activation information provided when the facial-surface change information is acquired or the second brain-function activation information detected when the facial-surface change information is acquired, and provides the determination result to the determination result output device;
a reference information storage unit that stores an amount of change from a reference correlation value with respect to the first brain-function activation information provided when the facial-surface change information is acquired or the second brain-function activation information detected when the facial-surface change information is acquired for each of a plurality of determination purposes, as reference information in relation to a state level;
a determination result decision unit that decides a determination result including the state level of a subject based on the reference information and a correlation value of determination information with respect to the first brain-function activation information provided when the facial-surface change information is acquired or the second brain-function activation information detected when the facial-surface change information is acquired related to the target purpose when acquiring the correlation value from the determination result output device; and
a determination result sending unit that sends the determination result to the determination result output device.

6. A determination result output system, comprising:
a determination result output device, comprising
a storage unit including a first memory that includes a brain-function activation information database that stores a first brain-function activation information for stimulating a brain function of a subject;

a peripheral information acquisition unit that acquires a second brain-function activation information provided from a peripheral brain-function activation information provision unit that exists in the peripheral area;
a first processor including
    a target purpose selection unit that selects one of a plurality of determination purposes as a target purpose,
    a brain-function activation information provision unit that provides a first brain-function activation information corresponding to the target purpose,
    a brain-function activation information detection unit that detects a second brain-function activation information corresponding to the target purpose,
    a facial-surface change information acquisition unit that acquires facial-surface change information indicative of a time-series change in facial surface data of the subject when the first brain-function activation information is provided, or when the second brain-function activation information is detected,
    a determination information generating unit that generates determination information from the facial-surface change information,
    a correlation value calculation unit that calculates a correlation value between (1) the determination information and (2) the first brain-function activation information provided when the facial-surface change information is acquired or the second brain-function activation information detected when the facial-surface change information is acquired,
    a correlation value sending unit that sends the correlation value in relation to the target purpose to the determination result provision device,
    a determination result acquisition unit that acquires a determination result from the determination result provision device in response to sending of the correlation value and the target purpose, the determination result being indicative of a state of the subject based on the first brain-function activation information provided when the facial-surface change information is acquired or the second brain-function activation information detected when the facial-surface change information is acquired and based on the facial-surface change information; and
    a determination result output unit that outputs the determination result indicative of a state of a subject; and
the determination result provision device: comprising
    a second processor including
        a reference information storage unit including a second memory that stores an amount of change from a reference correlation value with respect to the first brain-function activation information provided when the facial-surface change information is acquired or the second brain-function activation information detected when the facial-surface change information is acquired for each of the plurality of determination purposes, as reference information in relation to a state level,
        a determination result decision unit that decides the determination result including the state of the subject based on the reference information and a correlation related to the target purpose when acquiring the correlation value from the determination result output device, and
        a determination result sending unit that sends the determination result to the determination result output device.

7. The determination result output system according to claim 6, wherein the determination information generating unit extracts a determination component related to the first brain-function activation information provided when the facial-surface change information is acquired or the second brain-function activation information detected when the facial-surface change information is acquired corresponding to the target purpose using singular value decomposition, principal component analysis, or independent component analysis on the facial-surface change information, and generates the determination information from the determination component.

8. A determination result output device that sends facial-surface change information related to a target purpose to a determination result provision device and that acquires a determination result for the target purpose from the determination result provision device, the determination result output device comprising:
    a storage unit including a memory that includes a brain-function activation information database that stores a first brain-function activation information for stimulating a brain function of a subject;
    a peripheral information acquisition unit that acquires a second brain-function activation information provided from a peripheral brain-function activation information provision unit that exists in the peripheral area;
    a processor including
        a target purpose selection unit that selects one of a plurality of determination purposes as a target purpose;
        a brain-function activation information provision unit that provides the first brain-function activation information corresponding to the target purpose,
        a brain-function activation information detection unit that detects the second brain-function activation information corresponding to the target purpose,
        a facial-surface change information acquisition unit that acquires facial-surface change information indicative of a time-series change in facial surface data of the subject when the first brain-function activation information is provided, or when the second brain-function activation information is detected,
        a facial-surface change information sending unit that sends the facial-surface change information to the determination result provision device in relation to the target purpose,
        a determination result acquisition unit that acquires a determination result from the determination result provision device in response to sending of the facial-surface change information and the target purpose, the determination result being indicative of a state of the subject based on the first brain-function activation information provided when the facial-surface change information is acquired or the second brain-function activation information detected when the facial-surface change information is acquired and based on the facial-surface change information; and
        a determination result output unit that outputs the determination result.

9. A determination result output system, comprising:
a determination result output device, and
a determination result provision device, the determination result output device comprising:
- a storage unit including a first memory that includes a brain-function activation information database that stores a first brain-function activation information for stimulating a brain function of a subject,
- a peripheral information acquisition unit that acquires a second brain-function activation information provided from a peripheral brain-function activation information provision unit that exists in the peripheral area,
- a first processor including
  - a target purpose selection unit that selects one of a plurality of determination purposes as a target purpose,
  - a brain-function activation information provision unit that provides the first brain-function activation information corresponding to the target purpose,
  - a brain-function activation information detection unit that detects the second brain-function activation information corresponding to the target purpose,
  - a facial-surface change information acquisition unit that acquires facial-surface change information indicative of a time-series change in facial surface data of the subject when the first brain-function activation information is provided, or when the second brain-function activation information is detected,
  - a facial-surface change information sending unit that sends the facial-surface change information to the determination result provision device in relation to the target purpose,
  - a determination result acquisition unit that acquires a determination result from the determination result provision device in response to sending of the facial-surface change information and the target purpose, the determination result being indicative of a state of the subject based on the first brain-function activation information provided when the facial-surface change information is acquired or the second brain-function activation information detected when the facial-surface change information is acquired and based on the facial-surface change information, and
  - a determination result output unit that outputs the determination result,
- the determination result provision device comprising
  - a second processor including
    - a reference information storage unit including a second memory that stores an amount of change from a reference correlation value with respect to the first or the second brain-function activation information for each of the plurality of determination purposes, as reference information in relation to a state level,
    - a determination information generating unit that generates determination information from the facial-surface change information when acquiring the facial-surface change information related to the target purpose from the determination result output device,
    - a correlation value calculation unit that calculates a correlation value between (1) the determination information and (2) the first brain-function activation information provided when the facial-surface change information is acquired or the second brain-function activation information detected when the facial-surface change information is acquired,
    - a determination result decision unit that decides a determination result including a state level of the subject based on the correlation value and the reference information, and
    - a determination result sending unit that sends the determination result to the determination result output device.

10. The determination result output system according to claim 9, wherein the determination information generating unit extracts a determination component related to the first brain-function activation information provided when the facial-surface change information is acquired or the second brain-function activation information detected when the facial-surface change information is acquired corresponding to the target purpose using singular value decomposition, principal component analysis, or independent component analysis on the facial-surface change information, and generates the determination information from the determination component.

* * * * *